(12) United States Patent
Aissaoui et al.

(10) Patent No.: US 8,236,801 B2
(45) Date of Patent: Aug. 7, 2012

(54) 2-AZA-BICYCLO[2.2.1]HEPTANE DERIVATIVES

(75) Inventors: Hamed Aissaoui, Pulversheim (FR); Christoph Boss, Allschwil (CH); Ralf Koberstein, Lorrach (DE); Thierry Sifferlen, Wentzwiller (FR); Daniel Trachsel, Bern (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 164 days.

(21) Appl. No.: 12/867,630

(22) PCT Filed: Feb. 19, 2009

(86) PCT No.: PCT/IB2009/050689
§ 371 (c)(1),
(2), (4) Date: Aug. 13, 2010

(87) PCT Pub. No.: WO2009/104155
PCT Pub. Date: Aug. 27, 2009

(65) Prior Publication Data
US 2011/0009401 A1    Jan. 13, 2011

(30) Foreign Application Priority Data

Feb. 21, 2008    (WO) .................. PCT/IB2008/050622

(51) Int. Cl.
| A61K 31/49 | (2006.01) |
| A61K 31/4709 | (2006.01) |
| A61K 31/497 | (2006.01) |
| A61K 31/498 | (2006.01) |
| C07D 215/16 | (2006.01) |
| C07D 221/22 | (2006.01) |
| C07D 241/18 | (2006.01) |
| C07D 241/44 | (2006.01) |

(52) U.S. Cl. .................. 514/249; 514/255.05; 514/299; 514/314; 544/235; 544/405; 546/112; 546/169

(58) Field of Classification Search .................. None
See application file for complete search history.

(56) References Cited

U.S. PATENT DOCUMENTS

| 2003/0186964 A1 | 10/2003 | Branch et al. |
| 2009/0022670 A1 | 1/2009 | Alvaro et al. |
| 2009/0099228 A1 | 4/2009 | Aissaoui et al. |
| 2009/0163485 A1 | 6/2009 | Knust et al. |
| 2010/0016401 A1 | 1/2010 | Aissaoui et al. |
| 2010/0069418 A1 | 3/2010 | Aissaoui et al. |
| 2010/0113531 A1 | 5/2010 | Aissaoui et al. |
| 2010/0168134 A1 | 7/2010 | Breslin et al. |
| 2010/0184808 A1 | 7/2010 | Aissaoui et al. |
| 2010/0197733 A1 | 8/2010 | Aissaoui et al. |
| 2010/0204285 A1 | 8/2010 | Aissaoui et al. |
| 2010/0210667 A1 | 8/2010 | Alvaro et al. |
| 2010/0222328 A1 | 9/2010 | Aissaoui et al. |
| 2010/0222600 A1 | 9/2010 | Aissaoui et al. |
| 2011/0009461 A1 | 1/2011 | Aissaoui et al. |
| 2011/0039857 A1 | 2/2011 | Aissaoui et al. |
| 2011/0124636 A1 | 5/2011 | Aissaoui et al. |

FOREIGN PATENT DOCUMENTS

| WO | WO 01/96302 | 12/2001 |
| WO | WO 02/44172 | 6/2002 |
| WO | WO 02/089800 | 11/2002 |
| WO | WO 02/090355 | 11/2002 |
| WO | WO 03/002559 | 1/2003 |
| WO | WO 03/002561 | 1/2003 |
| WO | WO 03/032991 | 4/2003 |
| WO | WO 03/041711 | 5/2003 |
| WO | WO 03/051873 | 6/2003 |
| WO | WO 03051368 | 6/2003 |
| WO | WO 2004/026866 | 4/2004 |
| WO | WO 2004/041791 | 5/2004 |
| WO | WO 2004/041807 | 5/2004 |
| WO | WO 2004/041816 | 5/2004 |
| WO | WO 2006/011042 | 2/2006 |
| WO | WO 2007/122591 | 11/2007 |
| WO | WO 2008/150364 | 12/2008 |
| WO | WO 2009/143033 | 11/2009 |

OTHER PUBLICATIONS

Aissaoui et al; "N-Glycine-Sulfanamides as Potent Dual Orexin l/Orexin 2 Receptor Antagonists"; Bioorganic & Medicinal Chemistry Letters, vol. 18, pp. 5729-5733, 2008.

Bergman et al; "Proline Bis-Amides as Potein Dual Orexin Receptor Antagonists", Bioorganic & Medicinal Chemistry Letters, 2008. vol. 18, 1425-1430.

Bohm et al, "Scaffold Hopping"; Drug Disc. Today Tech. 2004, vol. 1, issue 3, pp. 217-224.

Boss et al; "Biomedical Application of Orexin/Hypocretin Receptor Ligands in Neuroscience"; Journal of Medicinal Chemistry, Vo;l. 52, No. 4, pp. 891-903; 2009.

Boss et al; "Orexin Receptor Antagonism: A New Principle in Neuroscience": CHIMIA; vol. 62, No. 12, pp. 974-979, 2008.

(Continued)

Primary Examiner — Rebecca Anderson
Assistant Examiner — Alicia L Otton
(74) Attorney, Agent, or Firm — Hoxie & Associates LLC

(57) ABSTRACT

The invention relates to novel 2-aza-bicyclo[2.2.1]heptane derivatives of formula (I),

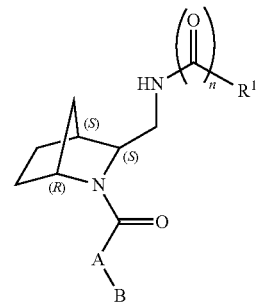

Formula (I)

wherein A, B, n and $R^1$ are as described in the description, and to the use of such compounds, or of pharmaceutically acceptable salts of such compounds, as medicaments, especially as orexin receptor antagonists.

22 Claims, No Drawings

OTHER PUBLICATIONS

Cox et al; "Conformational Analysis of N,N-distributed-, 4-diazepane Orexin Receptor Antagonists and Implications for Receptor Binding"; Bioorganic & Medicinal Chemistry Letters, 2009, vol. 19, 2997-3001.

Gatfield et al; "Orexin Receptor Antagonists: A New Concept in CNS Disorders"; ChemMedChem, vol. 5, pp. 1197-1214, 2010.

Langmead et al; "Characterisation of the Binding of [3H]-SB-674042, a Novel Nonpeptide Antagonist, to the Human Orexin-I Receptor"; British Journal of Pharmacology, vol. 141, pp. 340-346, 2004.

Roecker et al, "Orexin Receptor Antagonist: Medical Chemistry and Therapeutic Potential"; Current Topic Medicinal Chemistry, 2008, vol. 8, 977-987.

Sifferlen et al; "Novel Pyrazolo-Tetrahydropyridines as Potent Orexin Receptor Antagonists"; Bioorganic & Medicinal Chemistry Letters, vol. 20, pp. 1539-1542, 2010.

Whitman et al; "Discovery of a Potent, CNS-Penetrant Orexin Receptor Antagonist Based on N,N-Distributed-1,4-diazepane Scaffold that Promotes Sleep in Rats"; ChemMedChem, 2009, vol. 4, 1-6.

Berry, C.R., et al., "Cycloaddition Reactions of Thiazolium Azomethine Ylides: Application to Pyrrolo[2,1-*b*]thiazoles", Organic Letters, vol. 9, No. 21, pp. 4099-4102, (2007).

Chemelli, R.M., et al., "Narcolepsy in *orexin* Knockout Mice: Molecular Genetics of Sleep Regulation", Cell, vol. 98, pp. 437-451, (1999).

Eicher, T., et al., "The Chemistry of Heterocycles: Structure, Reactions, Synthesis, and Applications", 2$^{nd}$ Edition, Wiley, (2003).

Eissenstat, M.A., et al., "Aminoalkylindoles: Structure-Activity Relationships of Novel Cannabinoid Mimetics", J. Med. Chem., vol. 38, pp. 3094-3105, (1995).

Gould, P.L., "Salt Selection for Basic Drugs", International Journal of Pharmaceutics, vol. 33, pp. 201-217, (1986).

Hashimoto, N., et al., "Aza-Diels—Alder Reaction of Methyl 2-[(R)-1- Phenylethyl]iminoethanoate with Cyclopentadiene Using Practical and Environmentally Friendly Biphasic Solvent System", Organic Process Research & Development, vol. 9, pp. 105-109, (2005).

March, J., "Reduction of Carboxylic Acids, Esters, and Anhydrides to Aldehydes", Advanced Organic Chemistry, 4$^{th}$ edition, John Wiley & Sons, pp. 447-449 (2004).

March, J., "The Reduction of Nitriles to Aldehydes", Advanced Organic Chemistry, 4$^{th}$ edition, John Wiley & Sons, pp. 919-920 (2004).

March, J., "Oxidation or Dehydrogenation of Alcohols to Aldehydes and Ketones", Advanced Organic Chemistry, 4$^{th}$ edition, John Wiley & Sons, pp. 1167-1171(2004).

Monte, A.P., et al., "Dihydrobenzofuran Analogues of Hallucinogens. 3.[1] Models of 4-Substituted (2,5-Dimethoxyphenyl)alkylamine Derivatives with Rigidified Methoxy Groups[2]", J. Med. Chem., vol. 39, pp. 2953-2961, (1996).

Reisch, J., et al., "Natural Product Chemistry. Part 116 [1]. Synthesis of Daurine and Folidine: Two 2(1*H*)-Quinolinone Alkaloids from *Haplophyllum* Species", Monatshefte für Chemie, vol. 119, pp. 1169-1179, (1988).

Remington, "The Science and Practice of Pharmacy, 21$^{st}$ Edition (2005), Part 5, Pharmaceutical Manufacturing" [published by Lippincott Williams & Wilkins].

Sakurai, T., et al., "Orexins and Orexin Receptors: A Family of Hypothalamic Neuropeptides and G Protein-Coupled Receptors that Regulate Feeding Behavior", Cell, vol. 92, pp. 573-585, (1998).

Cai, J., et al. "Antagonists of the Orexin Receptors", Export Opinion on Therapeutic Patents, Informa Healthcare, GB, vol. 16, No. 5, pp. 631-646, May 1, 2006, XP002458093, ISSN: 1354-3776.

2-AZA-BICYCLO[2.2.1]HEPTANE DERIVATIVES

CROSS REFERENCE TO RELATED APPLICATIONS

This application is a United States Application under 35 U.S.C. 371 claiming benefit of PCT Application No. PCT/IB2009/050689, filed on Feb. 19, 2009, which claims the benefit of PCT Application No. PCT/IB2008/050622, filed on Feb. 21, 2008, the contents of each of which are incorporated herein by reference.

The present invention relates to 2-aza-bicyclo[2.2.1]heptane derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies as known from the literature.

The present invention provides 2-aza-bicyclo[2.2.1]heptane derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO01/096302. N-Aroyl cyclic amine derivatives are disclosed in WO02/090355.

The present invention describes for the first time 2-aza-bicyclo[2.2.1]heptane derivatives as orexin receptor antagonists.

1) A first aspect of the invention relates to compounds of formula (I) wherein the stereogenic centers are in absolute (1R,3S,4S)-configuration

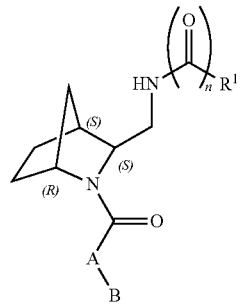

Formula (I)

wherein

A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen, $(C_{1-4})$alkoxy-$(C_{1-4})$alkoxy, and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine;

B represents an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, trifluoromethyl, trifluoromethoxy, —$NR^4R^5$, —$NHSO_2$—$(C_{1-4})$alkyl, —$N(R^4)C(O)R^5$ and halogen; or B represents a benzo[1,3]dioxolyl group.

n represents the integer 0 or 1;

$R^1$ represents heterocyclyl, wherein the heterocyclyl is unsubstituted or mono-, di-, or tri-substituted wherein the substituents are independently selected from the group consisting of $(C_{1-4})$alkyl, $(C_{1-4})$alkoxy, halogen, trifluoromethyl and —$NR^4R^5$; or $R^1$ represents a 1H-indenyl, a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl-, a chromanyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group; wherein said groups are unsubstituted, mono- or di-substituted wherein the substituents are independently selected from the group consisting of $(C_{1-4})$alkyl, $(C_{1-4})$alkoxy and halogen;

$R^2$ represents hydrogen or $(C_{1-4})$alkyl;

$R^3$ represents hydrogen or $(C_{1-4})$alkyl;

or $R^2$ and $R^3$ together with the nitrogen to which they are attached to form a pyrrolidine ring;

$R^4$ represents hydrogen or $(C_{1-4})$alkyl; and $R^5$ represents hydrogen or $(C_{1-4})$alkyl.

2) A second aspect of the invention relates to compounds of formula (I) according to embodiment 1), which compounds are also compounds of formula ($I_P$), wherein the stereogenic centers are in absolute (1R,3S,4S)-configuration:

Formula (Ip)

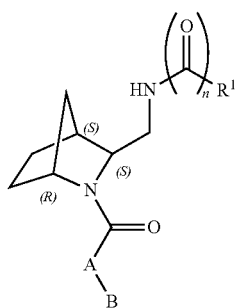

wherein

A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen, and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine;

B represents an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, trifluoromethyl, $-NR^4R^5$, $-NHSO_2-(C_{1-4})$alkyl, $-N(R^4)C(O)R^5$ and halogen;

n represents the integer 0 or 1;

$R^1$ represents heterocyclyl, wherein the heterocyclyl is unsubstituted or mono-, di-, or tri-substituted wherein the substituents are independently selected from the group consisting of $(C_{1-4})$alkyl, $(C_{1-4})$alkoxy, halogen, trifluoromethyl and $-NR^4R^5$; or $R^1$ represents a 1H-indenyl, a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl-, a chromanyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group; wherein said groups are unsubstituted, mono- or di-substituted wherein the substituents are independently selected from the group consisting of $(C_{1-4})$alkyl, $(C_{1-4})$alkoxy and halogen;

$R^2$ represents hydrogen or $(C_{1-4})$alkyl; and $R^3$ represents hydrogen or $(C_{1-4})$alkyl;

$R^4$ represents hydrogen or $(C_{1-4})$alkyl; and $R^5$ represents hydrogen or $(C_{1-4})$alkyl.

The invention also relates to salts, especially pharmaceutically acceptable salts, of the compounds of formula (I).

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

In this patent application, an arrow shows the point of attachment of the radical drawn. For example, the radical drawn below

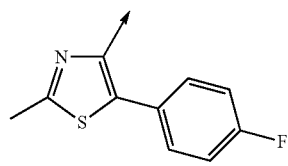

is the 5-(4-fluoro-phenyl)-2-methyl-thiazol-4-yl group.

The term "halogen" means fluorine, chlorine, bromine or iodine, preferably fluorine or chlorine, most preferably fluorine.

The term "$(C_{1-4})$alkyl", alone or in combination, means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl or tert.-butyl. Preferred are methyl and ethyl. Most preferred is methyl.

The term "$(C_{2-6})$alkinyl", alone or in combination, means a straight-chain or branched-chain alkinyl group with 2 to 6 carbon atoms. Examples of $(C_{2-6})$alkinyl groups are ethinyl, 1-propinyl, 1-butinyl, 3-methyl-1-butinyl, 1-pentinyl, 3,3-dimethyl-1-butinyl, 3-methyl-1-pentinyl, 4-methyl-1-pentinyl or 1-hexinyl. Preferred is ethinyl.

The term "$(C_{3-6})$cycloalkyl", alone or in combination, means a cycloalkyl group with 3 to 6 carbon atoms. Examples of $(C_{3-6})$cycloalkyl groups are cyclopropyl, cyclobutyl, cyclopentyl or cyclohexyl. Preferred is cyclopropyl.

The term "$(C_{1-4})$alkoxy", alone or in combination, means a group of the formula $(C_{1-4})$alkyl-O— in which the term "$(C_{1-4})$alkyl" has the previously given significance, such as methoxy, ethoxy, n-propoxy, isopropoxy, n-butoxy, isobutoxy, sec.-butoxy or tert.-butoxy. Preferred are methoxy and ethoxy. Most preferred is methoxy.

The term "aryl", alone or in combination, means a phenyl or a naphthyl group. Preferred is a phenyl group. The aryl group is unsubstituted or substituted as explicitly defined.

In case "A" represents "aryl" the term means the above-mentioned group which is unsubstituted (preferred) or mono- or di-substituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen, $(C_{1-4})$alkoxy-$(C_{1-4})$alkoxy, and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine. Notably, the substituents are independently selected from the group consisting of $(C_{1-4})$alkyl, $(C_{3-6})$cycloalkyl, $(C_{2-6})$alkinyl, $(C_{1-4})$alkoxy, $-NR^2R^3$, halogen, and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine. Preferably the substituents are independently selected from the group consisting of $(C_{1-4})$alkyl, $(C_{3-6})$cycloalkyl, $(C_{1-4})$alkoxy, and $-NR^2R^3$. A preferred example wherein "A" represents "aryl" is unsubstituted phenyl. In addition to the above-mentioned substituents, the substituent "A" is also substituted by the substituent "B", wherein B is preferably attached in ortho position to the point of attachment of the carbonyl group which links A to the 2-aza-bicyclo[2.2.1]heptane moiety.

In case "B" represents "aryl" the term means the above-mentioned group which is unsubstituted or mono-, di-, or tri-substituted, wherein the substituents are independently selected from the group consisting of $(C_{1-4})$alkyl, $(C_{1-4})$alkoxy, trifluoromethyl, trifluoromethoxy, $-NR^4R^5$, —NHSO$_2$—(C$_{1-4}$)alkyl, —N(R$^4$)C(O)R$^5$ and halogen. Notably, the substituents are independently selected from the group consisting of (C$_{1-4}$)alkyl, (C$_{1-4}$)alkoxy, trifluoromethyl, —NR$^4$R$^5$, —NHSO$_2$—(C$_{1-4}$)alkyl, —N(R$^4$)C(O)R$^5$ and halogen. Preferred examples wherein "B" represents "aryl" are unsubstituted or mono-, di-, or tri-substituted phenyl (preferred unsubstituted, mono- or di-substituted phenyl, especially preferred unsubstituted or mono-substituted phenyl), wherein the substituents are independently selected from the group consisting of (C$_{1-4}$)alkyl, (C$_{1-4}$)alkoxy, trifluoromethyl and halogen. In addition to the above-mentioned substituents, the substituent "B" is attached to the substituent "A".

Examples wherein "B" represents "aryl" are phenyl, 3-methylphenyl, 4-methylphenyl, 3,4-dimethylphenyl, 3,5-dimethylphenyl, 3-methoxyphenyl, 2-fluorophenyl, 3-fluorophenyl, 4-fluorophenyl, 3,4-difluorophenyl, 3-chlorophenyl, 2,3-dichlorophenyl, 3,4-dichlorophenyl, 3-trifluoromethylphenyl, 3-fluoro-2-methylphenyl, 3-fluoro-4-methylphenyl and 3-bromo-4-fluorophenyl. Preferred examples are phenyl, 3-methylphenyl, 4-methylphenyl, 3,4-dimethylphenyl, 3-methoxyphenyl, 3-fluorophenyl, 3-chlorophenyl and 3-bromo-4-fluorophenyl. In addition to the above-listed groups, further examples are 4-methoxyphenyl, 3,4-dimethoxyphenyl, and 3-trifluoromethoxyphenyl.

In case "A" and "B" both represent "aryl" the combination "A-B" preferably means a biphenyl group which is unsubstituted or mono- or di-substituted for "A" and unsubstituted or mono-, di- or tri-substituted for "B", wherein the substituents are independently selected from the group consisting of (C$_{1-4}$)alkyl, (C$_{1-4}$)alkoxy, trifluoromethyl and halogen. Preferred examples wherein "A" and "B" both represents "aryl" are biphenyl groups which are unsubstituted (preferred) or mono- or di-substituted for "A" and unsubstituted or mono-, di- or tri-substituted (preferred unsubstituted, mono- or di-substituted) for "B", wherein the substituents are independently selected from the group consisting of (C$_{1-4}$)alkyl and halogen. Especially preferred examples wherein "A" and "B" both represents "aryl" are biphenyl groups which are unsubstituted for "A" and mono-substituted for "B", wherein the substituent is halogen.

Examples of such a combination "A-B" are:

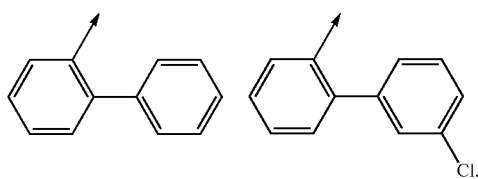

The term "heterocyclyl", alone or in combination, means a 5- to 10-membered monocyclic or bicyclic aromatic ring containing 1, 2 or 3 heteroatoms independently selected from oxygen, nitrogen and sulfur. Examples of such heterocyclyl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, pyrrolo[2,1-b]thiazolyl or imidazo[2,1-b]thiazolyl. The above-mentioned heterocyclyl groups are unsubstituted or mono-, di-, or tri-substituted as explicitly defined.

In case "A" represents "heterocyclyl" the term means the above-mentioned heterocyclyl groups which are unsubstituted or mono- or di-substituted (preferred unsubstituted or mono-substituted) wherein the substituents are independently selected from the group consisting of (C$_{1-4}$)alkyl, (C$_{3-6}$)cycloalkyl, (C$_{2-6}$)alkinyl, (C$_{1-4}$)alkoxy, NR$^2$R$^3$, halogen, (C$_{1-4}$)alkoxy-(C$_{1-4}$)alkoxy, and unsubstituted or independently mono- or di-substituted phenyl or pyridyl, wherein the substituents are independently selected from the group consisting of (C$_{1-4}$)alkyl, (C$_{1-4}$)alkoxy, trifluoromethyl, trifluoromethoxy, fluorine and chlorine. Notably, the substituents are independently selected from the group consisting of (C$_{1-4}$)alkyl, (C$_{3-6}$)cycloalkyl, (C$_{2-6}$)alkinyl, (C$_{1-4}$)alkoxy, NR$^2$R$^3$, halogen, and unsubstituted or independently mono- or di-substituted phenyl or pyridyl, wherein the substituents are independently selected from the group consisting of (C$_{1-4}$)alkyl, (C$_{1-4}$)alkoxy, trifluoromethyl, trifluoromethoxy, fluorine and chlorine. Preferably the substituents are independently selected from the group consisting of (C$_{1-4}$)alkyl, (C$_{3-6}$)cycloalkyl, (C$_{1-4}$)alkoxy, and —NR$^2$R$^3$. In a further preferred embodiment, in case "A" represents "heterocyclyl" the term means a 5- to 6-membered (preferably 5-membered) monocyclic heterocyclyl group as defined above (such as pyrimidinyl, pyrazinyl, oxazolyl, thiophenyl, or thiazolyl (notably pyrimidinyl, oxazolyl or thiazolyl); especially pyrimidinyl or thiazolyl; most preferred thiazolyl, especially thiazol-4-yl) which is unsubstituted or mono-substituted, wherein the substituent is selected from the group consisting of (C$_{1-4}$)alkyl, (C$_{3-6}$)cycloalkyl, (C$_{1-4}$)alkoxy and NR$^2$R$^3$. Preferred examples wherein "A" represents "heterocyclyl" are unsubstituted or mono-substituted heterocyclyl as mentioned above wherein the substituent is selected from (C$_{1-4}$) alkyl, (C$_{3-6}$)cycloalkyl and NR$^2$R$^3$. In a sub-embodiment, in case A represents a pyrazinyl- or a thiophenyl group, such group is preferably unsubstituted. In addition to the above-mentioned substituents, the substituent "A" is also substituted by the substituent "B", wherein B is preferably attached in ortho position to the point of attachment of the carbonyl group which links A to the 2-aza-bicyclo[2.2.1]heptane moiety.

Particular examples wherein "A" represents "heterocyclyl" are thiazol-4-yl, 2-methyl-thiazol-4-yl, 2-amino-thiazol-4-yl, 2-dimethylamino-thiazol-4-yl, 2-methyl-ethyl-amino-thiazole-4-yl, 2-diethylamino-thiazole-4-yl, 2-methylamino-thiazol-4-yl, 2-ethylamino-thiazol-4-yl, 2-(1-pyrrolidino)-thiazol-4-yl, 2-cyclopropyl-thiazol-4-yl, 2-methoxy-thiazol-4-yl, 2-ethoxy-thiazol-4-yl, and 2-(2-methoxy-ethoxy)-thiazole-4-yl, wherein B is attached in position 5 of the above thiazole-4-yl groups; 2-methyl-oxazol-4-yl, wherein B is attached in position 5 of the above oxazol-4-yl group; pyrazin-2-yl, wherein B is attached in position 3 to the pyrazin-2-yl group; 2-methyl-pyrimidin-5-yl, wherein B is attached in position 6 to the pyrimidin-5-yl group; and thiophen-2-yl, wherein B is attached in position 3 of the above thiophen-2-yl group. In a sub-embodiment, particular examples are thiazol-4-yl, 2-methyl-thiazol-4-yl, 2-amino-thiazol-4-yl, 2-dimethylamino-thiazol-4-yl, and 2-cyclopropyl-thiazol-4-yl, wherein B is attached in position 5 of the above thiazol-4-yl groups Preferred are 2-methyl-thiazol-4-yl, 2-dimethylamino-thiazol-4-yl and 2-cyclopropyl-thiazol-4-yl.

In one embodiment, particular examples of groups wherein "A" represents "heterocyclyl" and one of the substituents is represented by "B" are:

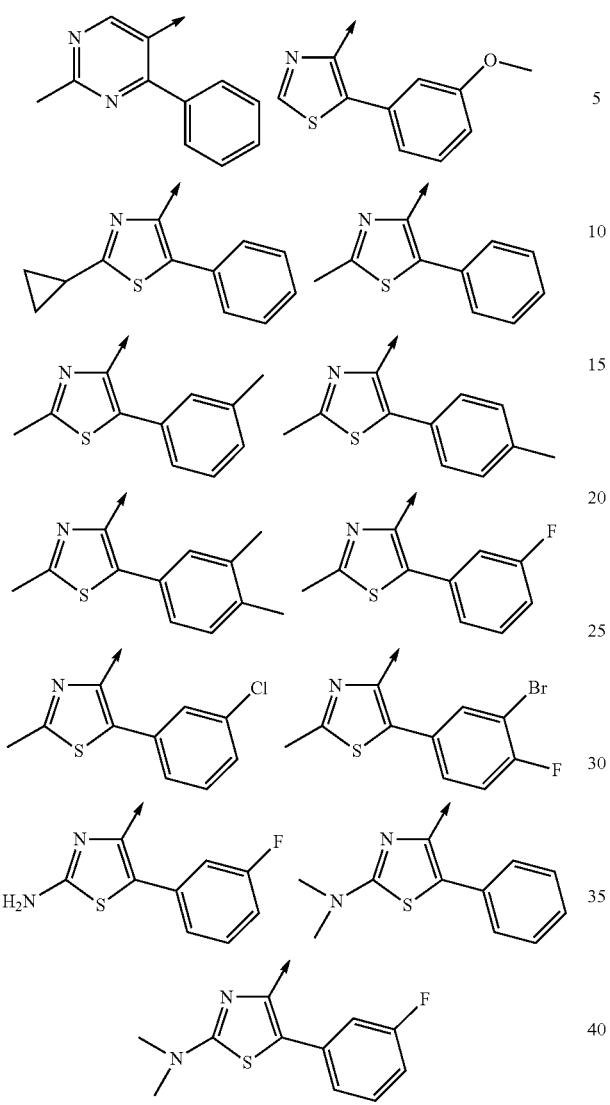
In a further embodiment and in addition to the above-listed groups, further examples of such groups are:
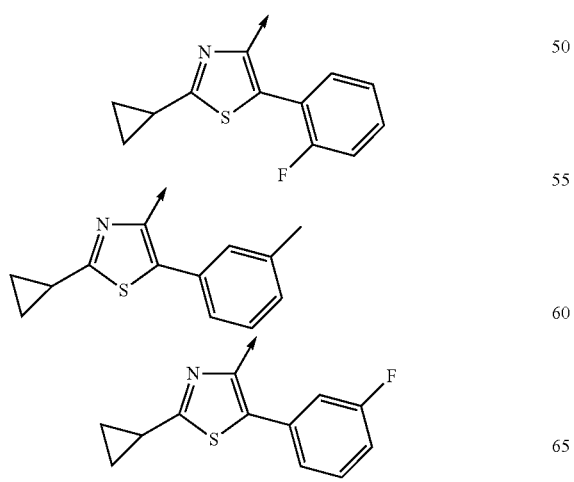
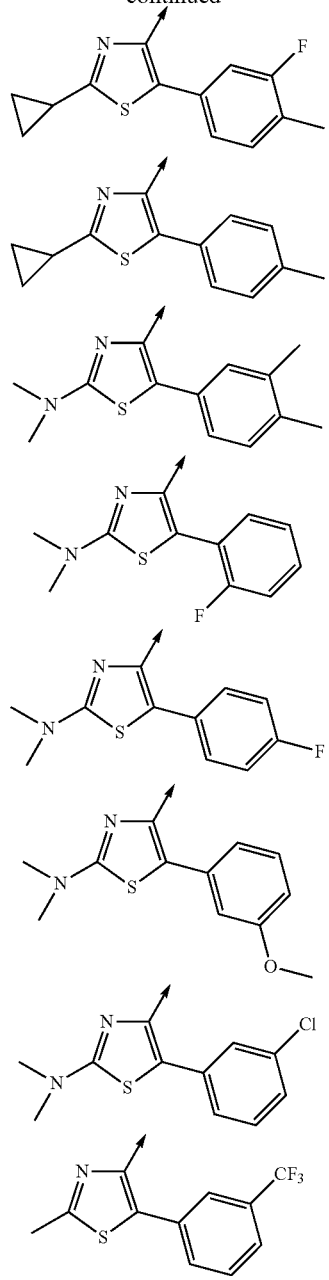
In a further embodiment and in addition to the above-listed groups, further examples of such groups are:
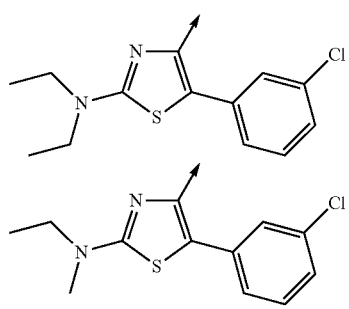

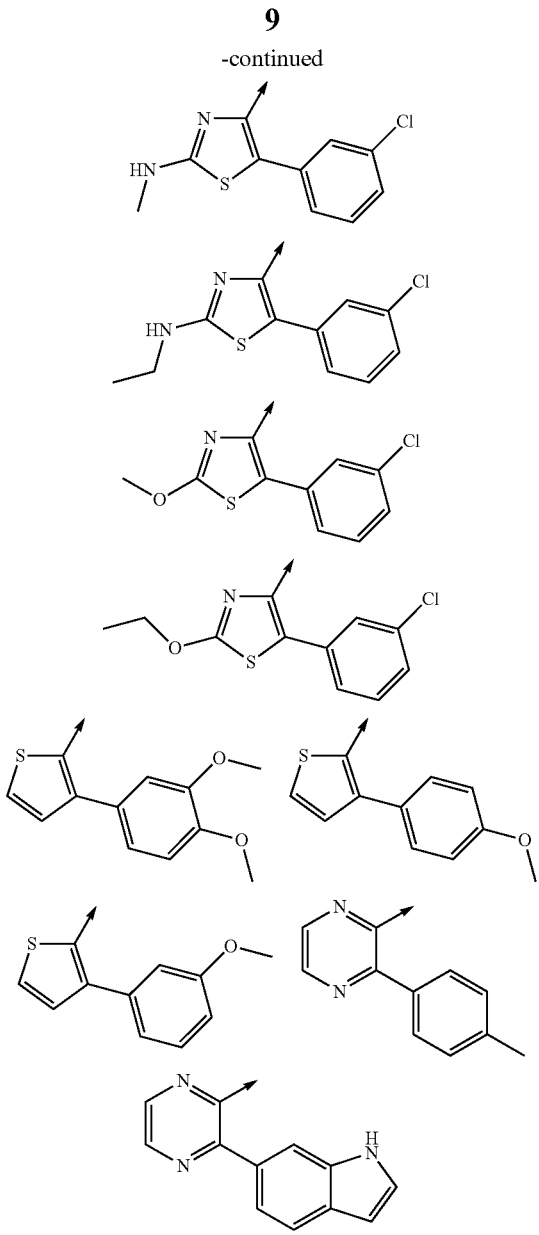

In a further embodiment and in addition to the above-listed groups, further examples of such groups are:

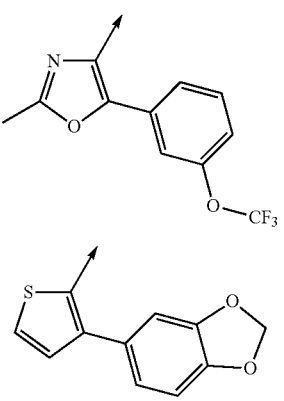

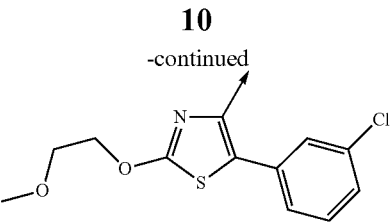

In case "B" represents "heterocyclyl" the term means the above-mentioned heterocyclyl groups which are unsubstituted (preferred) or mono-, di-, or tri-substituted wherein the substituents are independently selected from the group consisting of $(C_{1-4})$alkyl, $(C_{1-4})$alkoxy, trifluoromethyl, —$NR^4R^5$, —$NHSO_2$—$(C_{1-4})$alkyl, —$N(R^4)C(O)R^5$ and halogen. Especially, the substituents are independently selected from the group consisting of $(C_{1-4})$alkyl, $(C_{1-4})$alkoxy, trifluoromethyl, and halogen. Examples wherein "B" represents "heterocyclyl" are thienyl, thiazolyl, isothiazolyl, thiadiazolyl, pyrazolyl, pyridyl, pyrimidyl, pyridazinyl, and pyrazinyl. In addition to the above-listed examples, a particular example is indanyl (notably indan-6-yl). In addition to the above-mentioned substituents, the substituent "B" is attached to the substituent "A".

In case $R^1$ represents "heterocyclyl" the term means the above-mentioned heterocyclyl groups which are unsubstituted or mono-, di-, or tri-substituted (preferred unsubstituted or mono- or di-substituted, especially preferred unsubstituted or mono-substituted) wherein the substituents are independently selected from the group consisting of $(C_{1-4})$alkyl, $(C_{1-4})$alkoxy, halogen, trifluoromethyl and —$NR^4R^5$. In a further preferred embodiment, in case $R^1$ represents "heterocyclyl" the term means the above-mentioned heterocyclyl groups which are unsubstituted or mono-, di-, or tri-substituted (preferred unsubstituted or mono-substituted) wherein the substituents are independently selected from the group consisting of $(C_{1-4})$alkyl, $(C_{1-4})$alkoxy and halogen. In a further preferred embodiment, in case $R^1$ represents "heterocyclyl" the term means the above-mentioned heterocyclyl groups which are unsubstituted or mono-, di-, or tri-substituted (preferred unsubstituted or mono-substituted) wherein the substituents are independently selected from the group consisting of $(C_{1-4})$alkyl. In a further preferred embodiment, in case $R^1$ represents "heterocyclyl" the term means the above-mentioned heterocyclyl groups which are unsubstituted or mono-, di-, or tri-substituted (preferred unsubstituted or mono-substituted) wherein the substituent is methyl.

In another embodiment, in case n represents the integer 1, preferred examples wherein "$R^1$" represents "heterocyclyl" are unsubstituted or mono-, di-, or tri-substituted (preferred unsubstituted or mono-substituted) heterocyclyl; wherein the heterocyclyl is selected from the group consisting of isoxazolyl, thiazolyl, pyrazolyl, pyridyl, indolyl, benzofuranyl, benzothiophenyl, indazolyl, benzimidazolyl, benzoxazolyl, benzisoxazolyl, benzothiazolyl, benzoisothiazolyl, benzothiadiazolyl, quinoxalinyl, quinolinyl, isoquinolinyl, pyrrolo[2,1-b]thiazolyl, imidazo[1,2-a]pyridyl and imidazo[2,1-b]thiazolyl; notably, the heterocyclyl is selected from the group consisting of thiazolyl, pyrazolyl, pyridyl, indolyl, benzofuranyl, benzothiophenyl, indazolyl, benzimidazolyl, benzoxazolyl, benzisoxazolyl, benzothiazolyl, benzoisothiazolyl, benzothiadiazolyl, quinolinyl, isoquinolinyl, pyrrolo[2,1-b]thiazolyl, imidazo[1,2-a]pyridyl and (especially) imidazo[2,1-b]thiazolyl (especially the heterocyclyl is selected from thiazolyl, pyrazolyl, pyridyl, indolyl, benzofuranyl, indazolyl, benzimidazolyl, benzoxazolyl, benzisoxazolyl, benzothiazolyl, quinolinyl, pyrrolo[2,1-b]thiazolyl, imidazo

[1,2-a]pyridyl and (especially) imidazo[2,1-b]thiazolyl); wherein the substituents are independently selected from ($C_{1-4}$)alkyl, ($C_{1-4}$)alkoxy and halogen.

In another embodiment, in case n represents the integer 1, particular examples wherein "$R^1$" represents "heterocyclyl" are pyrazol-3-yl, indol-2-yl, indol-3-yl, benzofuran-4-yl, indazol-3-yl, benzimidazol-2-yl, benzimidazol-5-yl, benzoxazol-4-yl, benzisoxazol-3-yl, benzthiazol-7-yl, quinolin-8-yl, pyrrolo[2,1-b]thiazol-7-yl, imidazo[1,2-a]pyridine-3-yl and imidazo[2,1-b)]thiazol-5-yl (especially imidazo[2,1-b)] thiazol-5-yl). In addition to the above-listed examples, further examples are 5-ethyl-3-methyl-isoxazole-4-yl, 3-ethyl-5-methyl-isoxazole-4-yl, quinoxaline-5-yl, and benzo[d] isothiazol-3-yl. The above-mentioned heterocyclyl groups are unsubstituted, mono-, di-, or tri-substituted (preferred unsubstituted or mono-substituted), wherein the substituents are independently selected from the group consisting of ($C_{1-4}$)alkyl, ($C_{1-4}$)alkoxy and halogen.

In particular, the above mentioned "heterocyclyl" groups as used for the substituent "$R^1$" are preferably substituted as follows: pyrazolyl groups are di-substituted with ($C_{1-4}$)alkyl; indolyl groups are unsubstituted or di-substituted independently with ($C_{1-4}$)alkyl (especially methyl) or halogen; benzofuranyl groups are unsubstituted; indazolyl groups are unsubstituted or mono-substituted with ($C_{1-4}$)alkyl (especially methyl); benzimidazolyl groups are mono- or di-substituted with ($C_{1-4}$)alkyl (especially methyl); benzoxazolyl groups are mono-substituted with ($C_{1-4}$)alkyl (especially methyl); benzisoxazolyl groups are unsubstituted; benzthiazolyl groups are unsubstituted; quinolinyl groups are unsubstituted; pyrrolo[2,1-b]thiazolyl groups are mono-substituted with ($C_{1-4}$)alkyl (especially methyl); imidazo[1,2-a]pyridinyl groups are unsubstituted; and imidazo[2,1-b]thiazolyl groups are mono-substituted with ($C_{1-4}$)alkyl (especially methyl); further, benzoisothiazolyl groups are unsubstituted; quinoxalinyl groups are unsubstituted; and isoxazolyl groups are di-substituted with ($C_{1-4}$)alkyl.

Particular examples wherein $R^1$ represents "heterocyclyl" are:

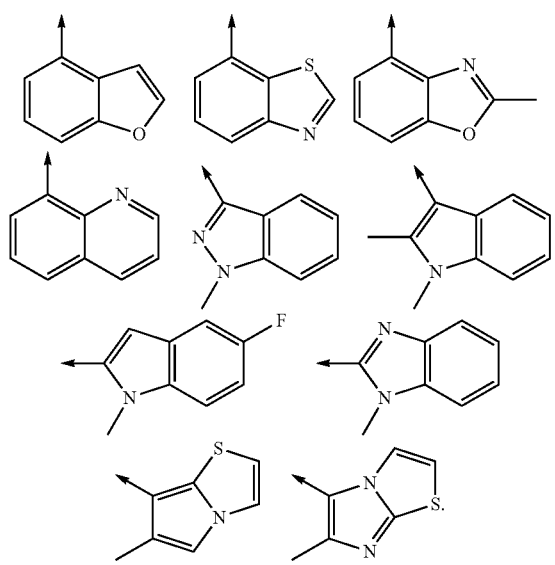

In a further embodiment, and in addition to the above-listed groups, further examples are:

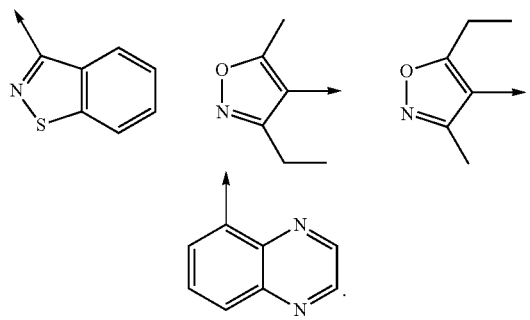

In another embodiment, in case n represents the integer 0, a preferred example wherein "$R^1$" represents "heterocyclyl" is mono- or di-substituted heterocyclyl; wherein the heterocyclyl is pyrimidyl (especially pyrimidin-2-yl); wherein the substituents are independently selected from ($C_{1-4}$)alkyl, ($C_{1-4}$)alkoxy, halogen, trifluoromethyl and —$NR^2R^3$. Especially, said pyrimidinyl is mono-substituted with halogen. A particular example is 5-bromo-pyrimidin-2-yl.

In case $R^1$ is different from "heterocyclyl", it presents a 1H-indenyl, a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl-, a chromanyl-, a 2,3-dihydro-thieno[3,4-b][1,4]dioxinyl-, a 3,4-dihydro-2H-benzo[1,4] oxazinyl- or a 2,3,6,7-tetrahydro-benzo[1,2-b; 4,5-b'] difuranyl-group. Especially it presents a 2,3-dihydro-benzo [1,4]dioxinyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group. The above-mentioned groups as used for the substituent $R^1$ are unsubstituted or mono- or di-substituted wherein the substituents are independently selected from the group consisting of ($C_{1-4}$)alkyl, ($C_{1-4}$)alkoxy and halogen. Preferably the above-mentioned groups are unsubstituted or mono-substituted with ($C_{1-4}$) alkyl. In particular, in case $R^1$ is different from "heterocyclyl", the above mentioned groups as used for the substituent "$R^1$" are preferably substituted as follows: 4H-benzo[1,3] dioxinyl-groups (especially 4H-benzo[1,3]dioxin-8-yl or 4H-benzo[1,3]dioxin-5-yl) are preferably unsubstituted, or mono-substituted in position 6 with fluoro; 3,4-dihydro-2H-benzo[1,4]oxazinyl-groups (especially 3,4-dihydro-2H-benzo[1,4]oxazin-5-yl) are preferably unsubstituted, or mono-substituted on the nitrogen atom with methyl (especially preferred: unsubstituted); 2,3-dihydro-benzofuranyl-groups (especially 2,3-dihydro-benzofuran-4-yl (preferred) or 2,3-dihydro-benzofuran-7-yl), benzo[1,3]dioxolyl-groups (especially benzo[1,3]dioxol-4-yl), 2,3-dihydro-benzo[1,4] dioxinyl- (especially 2,3-dihydro-benzo[1,4]dioxin-5-yl), 2H-chromenyl (especially chromen-5-yl), chromanyl- (especially chroman-5-yl or chroman-8-yl), 2,3-dihydro-thieno[3, 4-b][1,4]dioxinyl- (especially 2,3-dihydro-thieno[3,4-b][1, 4]dioxin-5-yl), and 2,3,6,7-tetrahydro-benzo[1,2-b; 4,5-b'] difuranyl-groups (especially 2,3,6,7-tetrahydro-benzo[1,2-b; 4,5-b']difuran-4-yl) are preferably unsubstituted.

The term "$NR^2R^3$" as used for formula (I) means for example $NH_2$ and $N(CH_3)_2$, $NH(CH_3)$, $N(CH_2CH_3)_2$, $NH(CH_2CH_3)$, $N(CH_3)(CH_2CH_3)$, and 1-pyrrolidino (especially it means $NH_2$ and $N(CH_3)_2$).

The term "$NR^2R^3$" as used for formula ($I_P$) means for example $NH_2$ and $N(CH_3)_2$.

The term "$NR^4R^5$" means for example $NH_2$ and $N(CH_3)_2$.

The term "—$NHSO_2$—($C_{1-4}$)alkyl" means for example —$NHSO_2$—$CH_3$.

The term "—N(R⁴)C(O)R⁵" means for example the group —NHC(O)CH₃.

The term "$(C_{1-4})$alkoxy-$(C_{1-4})$alkoxy" means for example the group CH₃—O—CH₂—CH₂—O—.

Further embodiments of the invention are presented hereinafter:

3) A further embodiment of the invention relates to compounds according to embodiments 1) or 2), wherein n represents the integer 1.

4) A further embodiment of the invention relates to compounds according to any one of embodiments 1) to 3), wherein
A represents phenyl or 5- to 6-membered monocyclic heterocyclyl, wherein the phenyl or heterocyclyl is unsubstituted or independently mono- or di-substituted, wherein the substituents are independently selected from the group consisting of $(C_{1-4})$alkyl, $(C_{3-6})$cycloalkyl, $(C_{1-4})$alkoxy, NR²R³ and halogen.

5) A further embodiment of the invention relates to compounds according to any one of embodiments 1) to 4), wherein
B represents aryl, wherein the aryl is unsubstituted or mono-, di-, or tri-substituted, wherein the substituents are independently selected from the group consisting of $(C_{1-4})$alkyl, $(C_{1-4})$alkoxy, trifluoromethyl and halogen.

6) A further embodiment of the invention relates to compounds according to any one of embodiments 1) to 5), wherein
R¹ represents heterocyclyl, wherein the heterocyclyl is unsubstituted or mono-, di-, or tri-substituted, wherein the substituents are independently selected from the group consisting of $(C_{1-4})$alkyl, $(C_{1-4})$alkoxy and halogen; or
R¹ represents a 1H-indenyl, a 2,3-dihydro-benzo[1,4]dioxinyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group, wherein said groups are unsubstituted or mono- or di-substituted wherein the substituents are independently selected from the group consisting of $(C_{1-4})$alkyl, $(C_{1-4})$alkoxy and halogen.

7) A further embodiment of the invention relates to compounds according to any one of embodiments 1) to 6), wherein
R¹ represents heterocyclyl, wherein the heterocyclyl is unsubstituted or mono-, di-, or tri-substituted, wherein the substituents are independently selected from the group consisting of $(C_{1-4})$alkyl, $(C_{1-4})$alkoxy and halogen.

8) A further embodiment of the invention relates to compounds according to any one of embodiments 1) to 7), wherein
A represents 5- to 6-membered monocyclic heterocyclyl, wherein the heterocyclyl is unsubstituted or mono-substituted wherein the substituent is selected from the group consisting of $(C_{1-4})$alkyl, $(C_{3-6})$cycloalkyl and NR²R³.

9) A further embodiment of the invention relates to compounds according to any one of embodiments 1) to 7), wherein,
in case R¹ represents heterocyclyl, said heterocyclyl is selected from isoxazolyl, thiazolyl, pyrazolyl, pyridyl, indolyl, benzofuranyl, benzothiophenyl, indazolyl, benzimidazolyl, benzoxazolyl, benzisoxazolyl, benzothiazolyl, benzoisothiazolyl, benzothiadiazolyl, quinoxalinyl, quinolinyl, isoquinolinyl, pyrrolo[2,1-b]thiazolyl, imidazo[1,2-a]pyridyl and imidazo[2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy and halogen.

10) A further embodiment of the invention relates to compounds according to any one of embodiments 1) to 7), wherein,
in case R¹ represents heterocyclyl, said heterocyclyl is selected from thiazolyl, pyrazolyl, pyridyl, pyrimidyl, indolyl, benzofuranyl, indazolyl, benzimidazolyl, benzoxazolyl, benzisoxazolyl, benzothiazolyl, quinolinyl, pyrrolo[2,1-b]thiazolyl, imidazo[1,2-a]pyridyl and imidazo[2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy and halogen.

11) A further embodiment of the invention relates to compounds according to any one of embodiments 1) to 7) or 9) to 10), wherein
A represents an oxazolyl-, a thiazolyl-, a pyrimidinyl-, a thiophenyl-, a pyrimidinyl-, or a pyrazinyl-group (notably an oxazolyl-, a thiazolyl-, or a pyrimidinyl-group), wherein said group is unsubstituted or mono-substituted, wherein the substituent is selected from $(C_{1-4})$alkyl, $(C_{3-6})$cycloalkyl, $(C_{1-4})$alkoxy and NR²R³.

12) A further embodiment of the invention relates to compounds according to any one of embodiments 1) to 11), wherein
A represents a thiazolyl-group, wherein said group is unsubstituted or mono-substituted, wherein the substituent is selected from $(C_{1-4})$alkyl, $(C_{3-6})$cycloalkyl and NR²R³.

13) A further embodiment of the invention relates to compounds according to any one of embodiments 1) to 7), 9) or 10), wherein
A represents a phenyl-group, wherein said group is unsubstituted or mono-substituted with $(C_{1-4})$alkyl.

14) A further embodiment of the invention relates to compounds according to any one of embodiments 1) to 7), 9) or 10), wherein A represents an unsubstituted phenyl-group.

15) A further embodiment of the invention relates to compounds according to any one of embodiments 1) to 11), wherein A represents a pyrimidyl-group, wherein said group is mono-substituted with $(C_{1-4})$alkyl.

16) A further embodiment of the invention relates to compounds according to any one of embodiments 1) to 11), wherein A represents an unsubstituted pyrazinyl-group.

17) A further embodiment of the invention relates to compounds according to any one of embodiments 1) to 11), wherein A represents an unsubstituted thiophenyl-group.

18) A further embodiment of the invention relates to compounds according to any one of embodiments 1) to 11), wherein A represents an oxazolyl-group, wherein said group is mono-substituted with $(C_{1-4})$alkyl.

19) A further embodiment of the invention relates to compounds according to any one of embodiments 1), 3), 4), or 6) to 19), wherein
B represents phenyl, wherein the phenyl is unsubstituted or mono- or di-substituted, wherein the substituents are independently selected from the group consisting of $(C_{1-4})$alkyl, $(C_{1-4})$alkoxy, trifluoromethyl, trifluoromethoxy and halogen.

20) A further embodiment of the invention relates to compounds according to any one of embodiments 1) to 19), wherein
B represents phenyl, wherein the phenyl is unsubstituted or mono- or di-substituted, wherein the substituents are independently selected from the group consisting of $(C_{1-4})$alkyl, $(C_{1-4})$alkoxy, trifluoromethyl and halogen.

21) A further embodiment of the invention relates to compounds according to any one of embodiments 1) to 8) or 11) to 20), wherein $R^1$ represents a 1H-indenyl, a 2,3-dihydro-benzo[1,4]dioxinyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group wherein said groups are unsubstituted or mono- or di-substituted wherein the substituents are independently selected from the group consisting of $(C_{1-4})$ alkyl, $(C_{1-4})$alkoxy and halogen.

22) A further embodiment of the invention relates to compounds according to any one of embodiments 1) to 8) or 11) to 20), wherein
$R^1$ represents a 2,3-dihydro-benzo[1,4]dioxinyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5b']difuranyl-group wherein said groups are unsubstituted.

23) A further embodiment of the invention relates to compounds according to any one of embodiments 1) to 20), wherein,
in case $R^1$ represents heterocyclyl, said heterocyclyl is selected from pyrrolo[2,1-b]thiazolyl and imidazo[2,1-b]thiazolyl, wherein said heterocyclyl is unsubstituted or mono-substituted with $(C_{1-4})$alkyl.

24) A further embodiment of the invention relates to compounds according to any one of embodiments 1) to 20), wherein, in case $R^1$ represents heterocyclyl, said heterocyclyl is pyrimidyl, which is unsubstituted or mono- or di-substituted, wherein the substituents are independently selected from $(C_{1-4})$alkyl, $(C_{1-4})$alkoxy and halogen.

25) A further embodiment of the invention relates to compounds according to any one of embodiments 1) to 20) or 24), wherein, in case $R^1$ represents heterocyclyl, said heterocyclyl is pyrimidyl which is mono-substituted with halogen.

26) A further embodiment of the invention relates to compounds according to any one of embodiments 1), 2), 4) to 20), or 24) to 25), wherein n represents the integer 0.

27) In another embodiment of the invention examples of compounds according to embodiment 1) are selected from the group consisting of:

Quinoline-8-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide;

Quinoline-8-carboxylic acid [(1R,3S,4S)-2-(2-methyl-5-m-tolyl-thiazole-4-carbonyl)-2-aza-bicyclo[2.2.1]hept-3-ylmethyl]-amide; 0

2,3-Dihydro-benzo[1,4]dioxine-5-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide;

2,3-Dihydro-benzo[1,4]dioxine-5-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide;

Benzofuran-4-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide;

Benzofuran-4-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide;

Benzofuran-4-carboxylic acid [(1R,3S,4S)-2-(2-methyl-4-phenyl-pyrimidine-5-carbonyl)-2-aza-bicyclo[2.2.1]hept-3-ylmethyl]-amide;

6-Methyl-imidazo[2,1-b]thiazole-5-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide;

6-Methyl-imidazo[2,1-b]thiazole-5-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide;

6-Methyl-imidazo[2,1-b]thiazole-5-carboxylic acid {(1R,3S,4S)-2-(2-methyl-5-m-tolyl-thiazole-4-carbonyl)-2-aza-bicyclo[2.2.1]hept-3-ylmethyl}-amide;

6-Methyl-imidazo[2,1-b]thiazole-5-carboxylic acid [(1R,3S,4S)-2-(biphenyl-2-carbonyl)-2-aza-bicyclo[2.2.1]hept-3-ylmethyl]-amide;

6-Methyl-imidazo[2,1-b]thiazole-5-carboxylic acid {(1R,3S,4S)-2-[5-(3-fluoro-phenyl)-2-methyl-thiazole-4-carbonyl]-2-aza-bicyclo[2.2.1]hept-3-ylmethyl}-amide;

6-Methyl-imidazo[2,1-b]thiazole-5-carboxylic acid [(1R,3S,4S)-2-(2-methyl-5-p-tolyl-thiazole-4-carbonyl)-2-aza-bicyclo[2.2.1]hept-3-ylmethyl]-amide;

6-Methyl-imidazo[2,1-b]thiazole-5-carboxylic acid {(1R,3S,4S)-2-[5-(3-bromo-4-fluoro-phenyl)-2-methyl-thiazole-4-carbonyl]-2-aza-bicyclo[2.2.1]hept-3-ylmethyl}-amide;

6-Methyl-imidazo[2,1-b]thiazole-5-carboxylic acid {(1R,3S,4S)-2-[5-(3,4-dimethyl-phenyl)-2-methyl-thiazole-4-carbonyl]-2-aza-bicyclo[2.2.1]hept-3-ylmethyl}-amide;

6-Methyl-imidazo[2,1-b]thiazole-5-carboxylic acid [(1R,3S,4S)-2-(2-dimethylamino-5-phenyl-thiazole-4-carbonyl)-2-aza-bicyclo[2.2.1]hept-3-ylmethyl]-amide;

6-Methyl-imidazo[2,1-b]thiazole-5-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

6-Methyl-imidazo[2,1-b]thiazole-5-carboxylic acid [(1R,3S,4S)-2-(2-methyl-5-phenyl-thiazole-4-carbonyl)-2-aza-bicyclo[2.2.1]hept-3-ylmethyl]-amide;

6-Methyl-imidazo[2,1-b]thiazole-5-carboxylic acid [(1R,3S,4S)-2-(2-cyclopropyl-5-phenyl-thiazole-4-carbonyl)-2-aza-bicyclo[2.2.1]hept-3-ylmethyl]-amide;

6-Methyl-imidazo[2,1-b]thiazole-5-carboxylic acid {(1R,3S,4S)-2-[5-(3-methoxy-phenyl)-thiazole-4-carbonyl]-2-aza-bicyclo[2.2.1]hept-3-ylmethyl}-amide;

2,3,6,7-Tetrahydro-benzo[1,2-b; 4,5-b']difuran-4-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide;

1-Methyl-1H-benzoimidazole-2-carboxylic acid [(1R,3S,4S)-2-(2-dimethylamino-5-phenyl-thiazole-4-carbonyl)-2-aza-bicyclo[2.2.1]hept-3-ylmethyl]-amide;

1-Methyl-1H-indazole-3-carboxylic acid [(1R,3S,4S)-2-(2-dimethylamino-5-phenyl-thiazole-4-carbonyl)-2-aza-bicyclo[2.2.1]hept-3-ylmethyl]-amide;

2-Methyl-benzooxazole-4-carboxylic acid [(1R,3S,4S)-2-(2-dimethylamino-5-phenyl-thiazole-4-carbonyl)-2-aza-bicyclo[2.2.1]hept-3-ylmethyl]-amide;

Benzothiazole-7-carboxylic acid [(1R,3S,4S)-2-(2-dimethylamino-5-phenyl-thiazole-4-carbonyl)-2-aza-bicyclo[2.2.1]hept-3-ylmethyl]-amide;

6-Methyl-pyrrolo[2,1-b]thiazole-7-carboxylic acid [(1R,3S,4S)-2-(2-dimethylamino-5-phenyl-thiazole-4-carbonyl)-2-aza-bicyclo[2.2.1]hept-3-ylmethyl]-amide;

1-Methyl-1H-benzoimidazole-2-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

Benzothiazole-7-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

1,2-Dimethyl-1H-indole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

5-Fluoro-1-methyl-1H-indole-2-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide; and 2-Methyl-benzooxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide.

28) In another embodiment, in addition to the compounds listed in embodiment 27), further examples of compounds according to embodiment 1) are selected from the group consisting of:

Benzothiazole-7-carboxylic acid {(R,S,S)-2-[5-(3-chloro-phenyl)-2-methoxy-thiazole-4-carbonyl]-2-aza-bicyclo[2.2.1]hept-3-ylmethyl}-amide;

Benzothiazole-7-carboxylic acid {(R,S,S)-2-[5-(3-chloro-phenyl)-2-ethoxy-thiazole-4-carbonyl]-2-aza-bicyclo[2.2.1]hept-3-ylmethyl}-amide;

Benzothiazole-7-carboxylic acid {(R,S,S)-2-[5-(3-chloro-phenyl)-2-(2-methoxy-ethoxy)-thiazole-4-carbonyl]-2-aza-bicyclo[2.2.1]hept-3-ylmethyl}-amide;

Benzothiazole-7-carboxylic acid {(R,S,S)-[2-(2-cyclopropyl-5-phenyl-thiazole-4-carbonyl)-2-aza-bicyclo[2.2.1]hept-3-ylmethyl]}-amide;

Benzothiazole-7-carboxylic acid {(R,R,S)-2-[2-cyclopropyl-5-(3-fluoro-phenyl)-thiazole-4-carbonyl]-2-aza-bicyclo[2.2.1]hept-3-ylmethyl}-amide;

Benzothiazole-7-carboxylic acid {(R,R,S)-2-[2-methyl-5-(3-trifluoromethyl-phenyl)-thiazole-4-carbonyl]-2-aza-bicyclo[2.2.1]hept-3-ylmethyl}-amide;

Benzothiazole-7-carboxylic acid {(R,R,S)-2-[2-dimethylamino-5-(3,4-dimethyl-phenyl)-thiazole-4-carbonyl]-2-aza-bicyclo[2.2.1]hept-3-ylmethyl}-amide;

Benzothiazole-7-carboxylic acid {(R,R,S)-2-[5-(3-chloro-phenyl)-2-dimethylamino-thiazole-4-carbonyl]-2-aza-bicyclo[2.2.1]hept-3-ylmethyl}-amide;

Benzothiazole-7-carboxylic acid {(R,R,S)-2-[5-(3-chloro-phenyl)-2-(ethyl-methyl-amino)-thiazole-4-carbonyl]-2-aza-bicyclo[2.2.1]hept-3-ylmethyl}-amide;

Benzothiazole-7-carboxylic acid {(1R,3S,4S)-2-[5-(3-chloro-phenyl)-2-diethylamino-thiazole-4-carbonyl]-2-aza-bicyclo[2.2.1]hept-3-ylmethyl}-amide;

Benzothiazole-7-carboxylic acid [(1R,3S,4S)-2-(3-p-tolyl-pyrazine-2-carbonyl)-2-aza-bicyclo[2.2.1]hept-3-ylmethyl]-amide;

Benzothiazole-7-carboxylic acid {(1R,3S,4S)-2-[3-(4-methoxy-phenyl)-thiophene-2-carbonyl]-2-aza-bicyclo[2.2.1]hept-3-ylmethyl}-amide;

Benzothiazole-7-carboxylic acid {(1R,3S,4S)-2-[3-(3-methoxy-phenyl)-thiophene-2-carbonyl]-2-aza-bicyclo[2.2.1]hept-3-ylmethyl}-amide;

Benzothiazole-7-carboxylic acid {(1R,3S,4S)-2-[3-(3,4-dimethoxy-phenyl)-thiophene-2-carbonyl]-2-aza-bicyclo[2.2.1]hept-3-ylmethyl}-amide;

Benzothiazole-7-carboxylic acid [(1R,3S,4S)-2-(3-benzo[1,3]dioxol-5-yl-thiophene-2-carbonyl)-2-aza-bicyclo[2.2.1]hept-3-ylmethyl]-amide;

Benzothiazole-7-carboxylic acid {(1R,3S,4S)-2-[2-dimethylamino-5-(2-fluoro-phenyl)-thiazole-4-carbonyl]-2-aza-bicyclo[2.2.1]hept-3-ylmethyl}-amide;

Benzothiazole-7-carboxylic acid {(1R,3S,4S)-2-[2-dimethylamino-5-(4-fluoro-phenyl)-thiazole-4-carbonyl]-2-aza-bicyclo[2.2.1]hept-3-ylmethyl}-amide;

Benzothiazole-7-carboxylic acid {(1R,3S,4S)-2-[2-dimethylamino-5-(3-methoxy-phenyl)-thiazole-4-carbonyl]-2-aza-bicyclo[2.2.1]hept-3-ylmethyl}-amide;

Benzothiazole-7-carboxylic acid [(1R,3S,4S)-2-(2-cyclopropyl-5-p-tolyl-thiazole-4-carbonyl)-2-aza-bicyclo[2.2.1]hept-3-ylmethyl]-amide;

Benzothiazole-7-carboxylic acid {(1R,3S,4S)-2-[2-cyclopropyl-5-(2-fluoro-phenyl)-thiazole-4-carbonyl]-2-aza-bicyclo[2.2.1]hept-3-ylmethyl}-amide;

Benzothiazole-7-carboxylic acid [(1R,3S,4S)-2-(2-cyclopropyl-5-m-tolyl-thiazole-4-carbonyl)-2-aza-bicyclo[2.2.1]hept-3-ylmethyl]-amide;

Benzothiazole-7-carboxylic acid {(1R,3S,4S)-2-[2-cyclopropyl-5-(3-fluoro-4-methyl-phenyl)-thiazole-4-carbonyl]-2-aza-bicyclo[2.2.1]hept-3-ylmethyl}-amide;

Benzothiazole-7-carboxylic acid {(1R,3S,4S)-2-[5-(3-chloro-phenyl)-2-methylamino-thiazole-4-carbonyl]-2-aza-bicyclo[2.2.1]hept-3-ylmethyl}-amide;

Benzothiazole-7-carboxylic acid {(1R,3S,4S)-2-[5-(3-chloro-phenyl)-2-ethylamino-thiazole-4-carbonyl]-2-aza-bicyclo[2.2.1]hept-3-ylmethyl}-amide;

Benzothiazole-7-carboxylic acid {(1R,3S,4S)-2-[2-methyl-5-(3-trifluoromethoxy-phenyl)-oxazole-4-carbonyl]-2-aza-bicyclo[2.2.1]hept-3-ylmethyl}-amide;

Benzo[d]isothiazole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

5-Ethyl-3-methyl-isoxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

3-Ethyl-5-methyl-isoxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

Quinoxaline-5-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

Benzothiazole-7-carboxylic acid {(1R,3S,4S)-2-[3-(1H-indol-6-yl)-pyrazine-2-carbonyl]-2-aza-bicyclo[2.2.1]hept-3-ylmethyl}-amide;

Benzothiazole-7-carboxylic acid {(1S,3R,4R)-2-[5-(2-fluoro-phenyl)-2-pyrrolidin-1-yl-thiazole-4-carbonyl]-2-aza-bicyclo[2.2.1]hept-3-ylmethyl}-amide;

Benzothiazole-7-carboxylic acid [(1S,3R,4R)-2-(2-dimethylamino-5-m-tolyl-thiazole-4-carbonyl)-2-aza-bicyclo[2.2.1]hept-3-ylmethyl]-amide;

Benzothiazole-7-carboxylic acid {(1S,3R,4R)-2-[2-(ethyl-methyl-amino)-5-(3-methoxy-phenyl)-thiazole-4-carbonyl]-2-aza-bicyclo[2.2.1]hept-3-ylmethyl}-amide;

Benzothiazole-7-carboxylic acid {(1S,3R,4R)-2-[5-(3-bromo-4-fluoro-phenyl)-2-dimethylamino-thiazole-4-carbonyl]-2-aza-bicyclo[2.2.1]hept-3-ylmethyl}-amide;

Benzothiazole-7-carboxylic acid {(1S,3R,4R)-2-[5-(4-fluoro-phenyl)-2-pyrrolidin-1-yl-thiazole-4-carbonyl]-2-aza-bicyclo[2.2.1]hept-3-ylmethyl}-amide;

Benzothiazole-7-carboxylic acid {(1S,3R,4R)-2-[2-dimethylamino-5-(4-fluoro-phenyl)-thiazole-4-carbonyl]-2-aza-bicyclo[2.2.1]hept-3-ylmethyl}-amide;

Benzothiazole-7-carboxylic acid {(1S,3R,4R)-2-[2-diethylamino-5-(2-fluoro-phenyl)-thiazole-4-carbonyl]-2-aza-bicyclo[2.2.1]hept-3-ylmethyl}-amide;

Benzothiazole-7-carboxylic acid {(1S,3R,4R)-2-[2-dimethylamino-5-(3-fluoro-4-methyl-phenyl)-thiazole-4-carbonyl]-2-aza-bicyclo[2.2.1]hept-3-ylmethyl}-amide;

Benzothiazole-7-carboxylic acid {(1S,3R,4R)-2-[2-(ethyl-methyl-amino)-5-(4-fluoro-phenyl)-thiazole-4-carbonyl]-2-aza-bicyclo[2.2.1]hept-3-ylmethyl}-amide;

Benzothiazole-7-carboxylic acid [(1S,3R,4R)-2-(2-dimethylamino-5-p-tolyl-thiazole-4-carbonyl)-2-aza-bicyclo[2.2.1]hept-3-ylmethyl]-amide;

Benzothiazole-7-carboxylic acid {(1S,3R,4R)-2-[2-dimethylamino-5-(3-trifluoromethyl-phenyl)-thiazole-4-carbonyl]-2-aza-bicyclo[2.2.1]hept-3-ylmethyl}-amide; and Benzothiazole-7-carboxylic acid {(1S,3R,4R)-2-[2-diethylamino-5-(4-fluoro-phenyl)-thiazole-4-carbonyl]-2-aza-bicyclo[2.2.1]hept-3-ylmethyl}-amide.

Also part of the invention are compounds of formula (I) and pharmaceutically acceptable salts thereof.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Where the plural form is used for compounds, salts, pharmaceutical compositions, diseases or the like, this is intended to mean also a single compound, salt, disease or the like.

The compounds of formula (I) and their pharmaceutically acceptable salts can be used as medicaments, e.g. in the form of pharmaceutical compositions for enteral or parenteral administration.

A further aspect of the invention is a pharmaceutical composition containing at least one compound according to formula (I), or a pharmaceutically acceptable salt thereof, and a pharmaceutically acceptable carrier material.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I).

The compounds according to formula (I) may be used for the preparation of a medicament and are suitable for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

Compounds of formula (I) are particularly suitable for use in the treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds of formula (I) are particularly suitable for use in the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of formula (I) are particularly suitable for use in the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of formula (I) are particularly suitable for use in the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of formula (I) are particularly suitable for use in the treatment of diseases or disorders selected from the group consisting of psychoactive substance use and abuse that comprise all types of psychological or physical addictions and their related tolerance and dependence components.

Besides, any preferences indicated for the compounds of formula (I) (whether for the compounds themselves, salts thereof, compositions containing the compounds or salts thereof, uses of the compounds or salts thereof, etc.) apply mutatis mutandis to compounds of formula ($I_P$).

A further aspect of the invention is a process for the preparation of compounds of formula (I). Compounds according to formula (I) of the present invention can be prepared according to the general sequence of reactions outlined in the schemes below, wherein A, B, n and $R^1$ are as defined for formula (I). The compounds obtained may also be converted into pharmaceutically acceptable salts thereof in a manner known per se.

In general, all chemical transformations can be performed according to well-known standard methodologies as described in the literature or as described in the procedures below.

PREPARATION OF COMPOUNDS OF FORMULA (I)

(1S,3S,4R)-2-((R)-1-Phenyl-ethyl)-2-aza-bicyclo[2.2.1] hept-5-ene-3-carboxylic acid methyl ester (1) can be synthesized according to a literature procedure (N. Hashimoto, H. Yasuda, M. Hayashi, Y. Tanabe Org. Proc. Res. Dev., 2005, 9, 105-109); the configuration of the stereocenters is assigned in accordance with this reference as well. The exchange of the protecting group to tert.-butoxy-carbonyl can be done by removal of the phenethyl-moiety of (1) under hydrogenation conditions (e.g. $H_2$ and catalytic amounts of Pd/C) in the presence of $Boc_2O$. By reduction of the ester-functionality of (2) with, for instance, DIBAL at low temperatures the respective alcohol (3) can be obtained which can be oxidized to aldehyde (4) by Swern- or Dess-Martin-oxidation. After reductive amination of (4) with benzylamine in the presence of a reducing agent like sodium triacetoxyborohydride the benzyl group of (5) can be removed by hydrogenolysis to yield the primary amine (6). The acylation of (6) with a carboxylic acid $R^1COOH$ in the presence of a coupling reagent like TBTU resulted in the formation of amides (7) which after removal of the Boc-group under acidic conditions (e.g. HCl in dioxane) can be transferred to compounds of formula (I) by amide coupling (e.g. B-A-COOH, TBTU or B-A-COCl).

Scheme 1: Synthesis of compounds of formula (I)

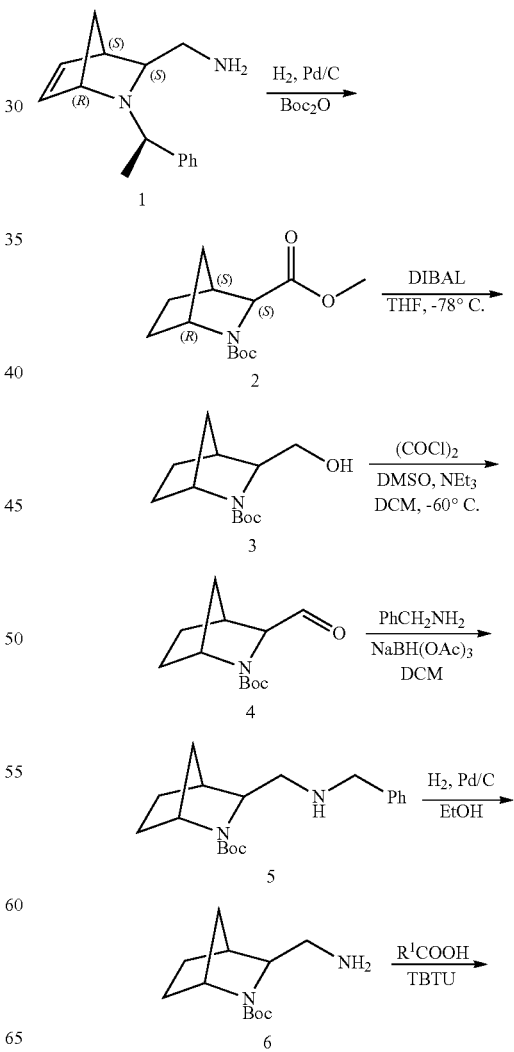

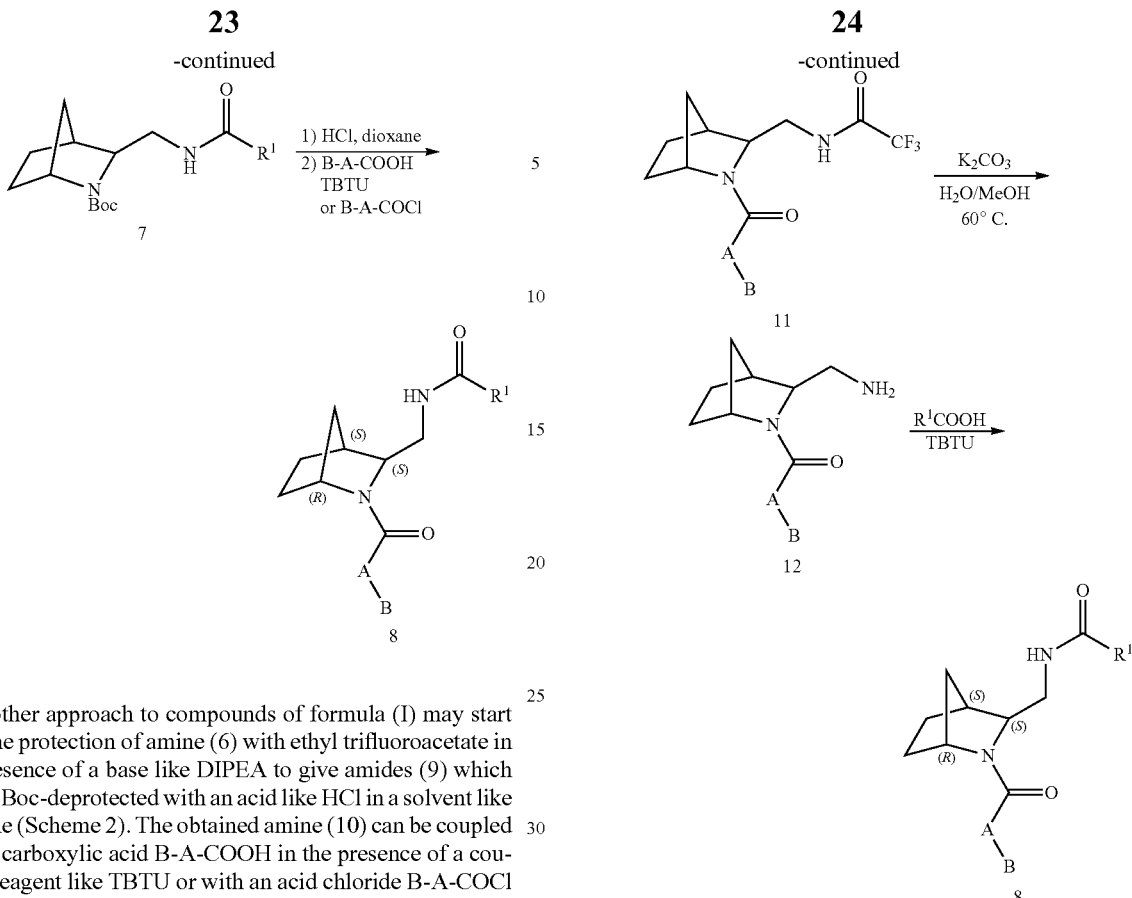

Another approach to compounds of formula (I) may start with the protection of amine (6) with ethyl trifluoroacetate in the presence of a base like DIPEA to give amides (9) which can be Boc-deprotected with an acid like HCl in a solvent like dioxane (Scheme 2). The obtained amine (10) can be coupled with a carboxylic acid B-A-COOH in the presence of a coupling reagent like TBTU or with an acid chloride B-A-COCl to an amide (11). After deprotection with for instance $K_2CO_3$ or NaOH in alcohol/water mixtures amines (12) can be obtained which can be coupled with a carboxylic acid $R^1$COOH in the presence of a coupling reagent like TBTU to compounds (8) of formula (I).

Scheme 2: Alternative synthesis of compounds of formula (I)

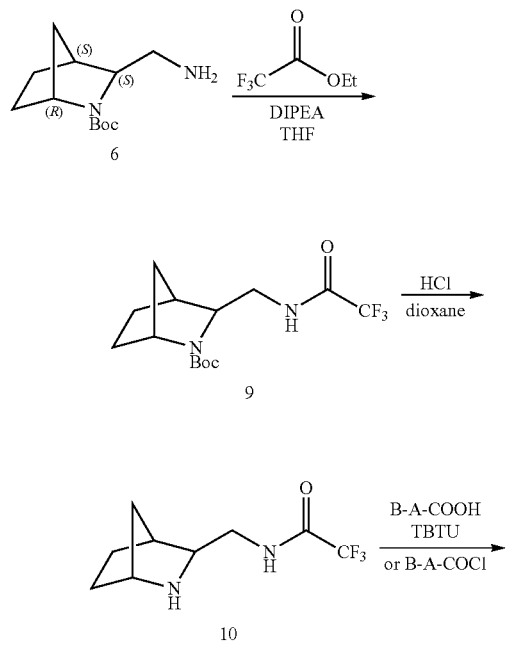

Scheme 3: Alternative synthesis of compounds of formula (I), wherein n equals 0; X represents chlorine or bromine

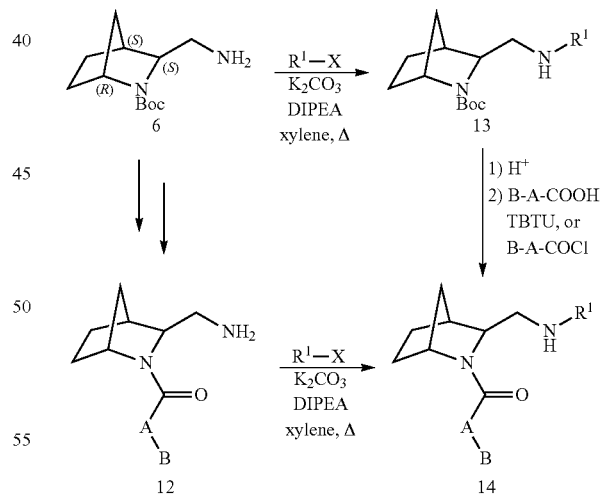

Compounds of formula (I) in which n equals 0 can be synthesized according to one of the pathways described in scheme 3. Starting from the Boc-protected compound (6) heterocyclyl-substituted compounds (13) may be obtained in a substitution reaction with for instance heterocyclyl chlorides or bromides in the presence of a base like $K_2CO_3$ and/or DIPEA at elevated temperatures. After acid catalyzed removal of the Boc-protecting group compounds (14) of formula (I) can be obtained by amide coupling with the respective carboxylic acid B-A-COOH in the presence of a coupling reagent like for instance TBTU or by reaction with an acid chloride like B-A-COCl in the presence of a base like DIPEA. Alternatively compounds (12) may be transferred to compounds (14) of formula (I) by substitution reaction with for instance heterocyclyl chlorides or bromides in the presence of a base like $K_2CO_3$ and/or DIPEA at elevated temperatures.

Thiazole-4-carboxylic acid derivatives of formula B-A-COOH can for instance be synthesised according to scheme 4.

reaction of (19) with amines $HNR^2R^3$ and subsequent saponification. They may also be transferred to 2-alkoxy substituted analogues (21) by reaction with sodium alkoxide and subsequent saponification with NaOH solution. In addition compounds (23) which are unsubstituted in 2-position can be synthesized by hydrogenation of (19) in the presence of palladium on charcoal and subsequent saponification of the intermediate ester (22).

Aldehydes B—CHO are commercially available or may be synthesized by procedures known from the literature like for Scheme 4: Synthesis of thiazole-4-carboxylic acid derivatives, wherein R is $(C_{1-4})$alkyl, $(C_{3-6})$cycloalkyl or $NR^2R^3$ and R' is $(C_{1-4})$alkyl

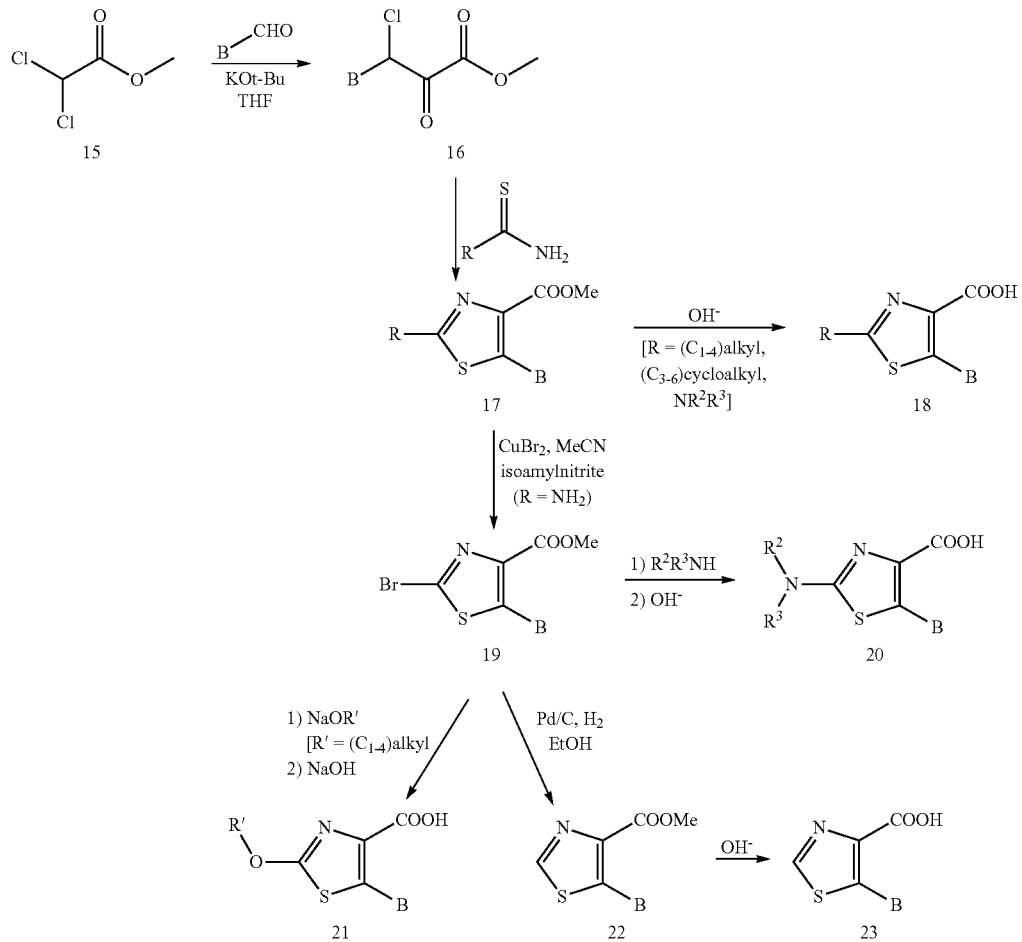

By reaction of methyl dichloroacetate (15; commercially available) with an aldehyde in the presence of a base like potassium tert.-butoxide the 3-chloro-2-oxo-propionic ester derivatives (16) can be obtained which can be transformed in a reaction with thioamides [R=$(C_{1-4})$alkyl or $(C_{3-6})$cycloalkyl] to 2-alkyl- or 2-cycloalkyl-substituted thiazole derivatives (17) or in a reaction with thioureas (R=$NR^2R^3$) to 2-amino-substituted thiazole derivatives (17). Saponification of the ester function with an aq. solution of e.g. NaOH in a solvent like MeOH results in formation of the desired carboxylic acids (18, R=$(C_{1-4})$alkyl, $(C_{3-6})$cycloalkyl or $NR^2R^3$). 2-Bromo-thiazole derivatives (19) can for instance be obtained by reaction of the respective 2-amino-thiazole derivative (17, R=$NH_2$) with isoamylnitrite in the presence of copper(II)bromide. The ester derivatives (19) can be transferred to 2-amino-substituted thiazole derivatives (20) by instance reduction of the respective carboxylic acid or their different derivatives with a reducing agent, by reduction of the respective nitrile or by oxidation of benzylic alcohols and their heterocyclic analogues with oxidating agents (e.g.: J. March, *Advanced Organic Chemistry*, 4$^{th}$ edition, John Wiley & Sons, p. 447-449, 919-920 and 1167-1171).

$(C_{3-6})$Cycloalkyl-thioamides may be synthesized by treatment of $(C_{3-6})$cycloalkyl-carboxamides with Lawesson's reagent.

Carboxylic acids of formula $R^1$—COOH are commercially available or well known in the art (Lit. e.g. WO2001/96302; T. Eicher, S. Hauptmann "The chemistry of Heterocycles: Structure, Reactions, Syntheses, and Applications", 2nd Edition 2003, Wiley, ISBN 978-3-527-30720-3).

Derivatives of formula $R^1$—COOH wherein $R^1$ is benzo[1,4]oxazine can be synthesised according to scheme 5.

By hydrogenation of methyl 3-nitrosalicylate (commercially available) in MeOH 3-amino-2-hydroxy-benzoic acid methyl ester (26, $R^a$=COOMe, $R^b$=H) may be obtained. The regioisomer (26, $R^a$=H, $R^b$=COOMe) may be synthesized by esterification of commercially available 3-hydroxy-anthranilic acid with (trimethylsilyl)diazomethane. Cyclization of one or the other amino-hydroxy-benzoic acid (26) with chloroacetyl chloride in the presence of a base like $K_2CO_3$ may lead to 3-oxo-3,4-dihydro-2H-benzo[1,4]oxazine derivatives (27) which may be reduced to 3,4-dihydro-2H-benzo[1,4]oxazine derivatives (28) with $NaBH_4$ in the presence of boron trifluoride diethyl etherate. Compounds (28) may be alkylated at the nitrogen atom with methyl iodide in the presence of a base like $K_2CO_3$ in a solvent like DMF to give the respective analogues (29). By saponification of the respective ester derivatives (28 or 29) with NaOH in a solvent mixture like water/EtOH the desired acids (30, 31, 32 or 33) may be obtained.

Ester Cleavage:

Scheme 5: Synthesis of benzo[1,4]oxazine-carboxylic acid derivatives

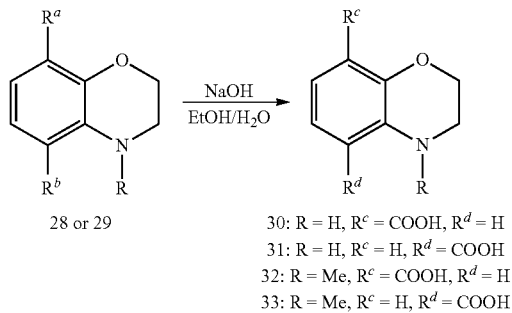

30: R = H, $R^c$ = COOH, $R^d$ = H
31: R = H, $R^c$ = H, $R^d$ = COOH
32: R = Me, $R^c$ = COOH, $R^d$ = H
33: R = Me, $R^c$ = H, $R^d$ = COOH

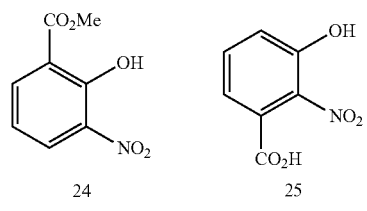

24          25

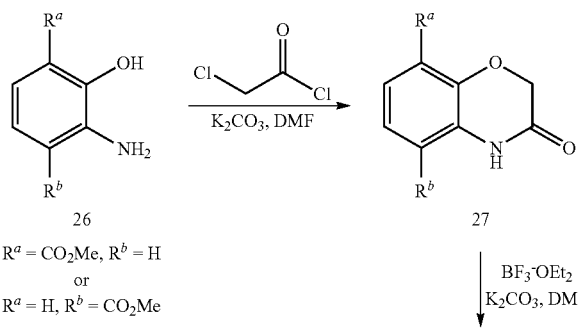

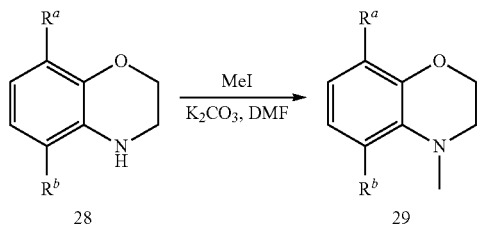

Derivatives of formula R¹—COOH wherein R¹ is chroman may be for instance synthesised according to scheme 6.

The synthesis of chroman-5-carboxylic acid derivatives may be started with the alkylation of 3-hydroxy-benzoic acid methyl ester (34; commercially available) with propargyl bromide in the presence of $K_2CO_3$ to give phenylether (35) which may be cyclised to the chromen derivative (36) by heating to reflux in N,N-diethylaniline. The carboxylic ester may be saponified by treatment of (36) with NaOH in MeOH and water and the obtained chromen derivative (37) may be hydrogenated to give the desired acid (38). The corresponding chroman-8-carboxylic acid derivatives may be synthesized by reduction of 4-chromanone (39; commercially available) with zinc in acetic acid and subsequent ortho-metalation of the intermediate chroman derivative (40) with n-BuLi and trapping with carbon dioxide to give the desired acid (41).

3-oxo-butyric acid methyl ester (42; commercially available) by reaction with thiourea in a solvent like EtOH at elevated temperatures. The obtained amino-thiazole (43) may be converted to the imidazo[2,1-b]thiazole derivative (44) by alkylation and subsequent cyclization with bromoacetaldehyde diethyl acetal in the presence of an acid like concentrated hydrochloric acid. By saponification of (44) with for instance NaOH in solvents like THF and MeOH the desired acids (45) may be obtained.

Scheme 7: Synthesis of imidazo [2,1-b] thiazole-carboxylic acid derivatives wherein R is methyl or ethyl, $R^a$ is hydrogen or methyl, $R^b$ is hydrogen or methyl Scheme 6: Synthesis of chroman-carboxylic acid derivatives

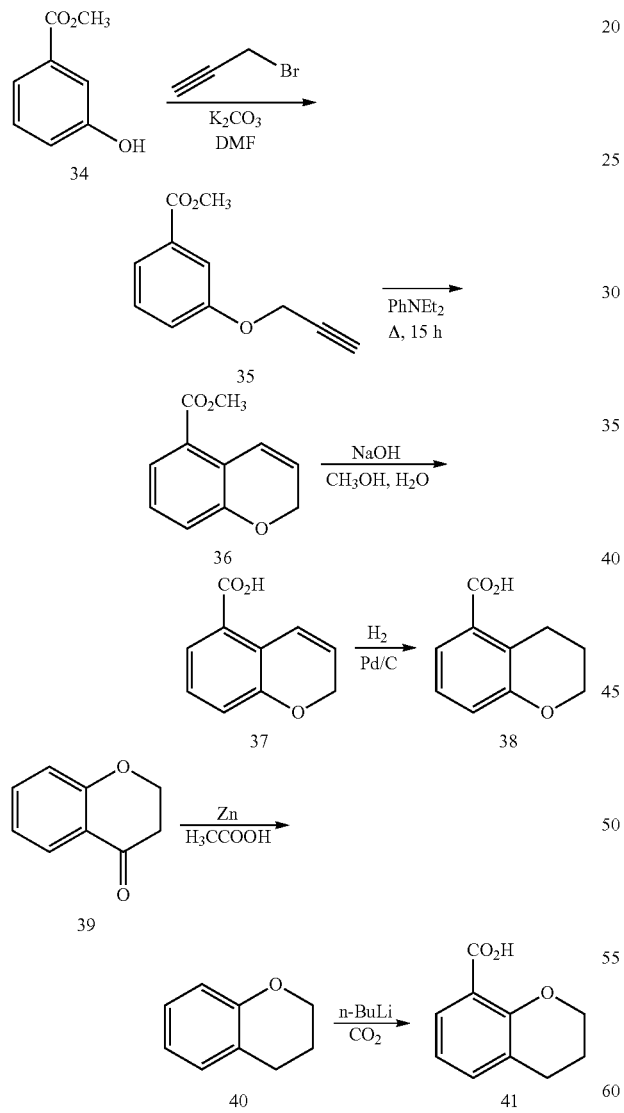

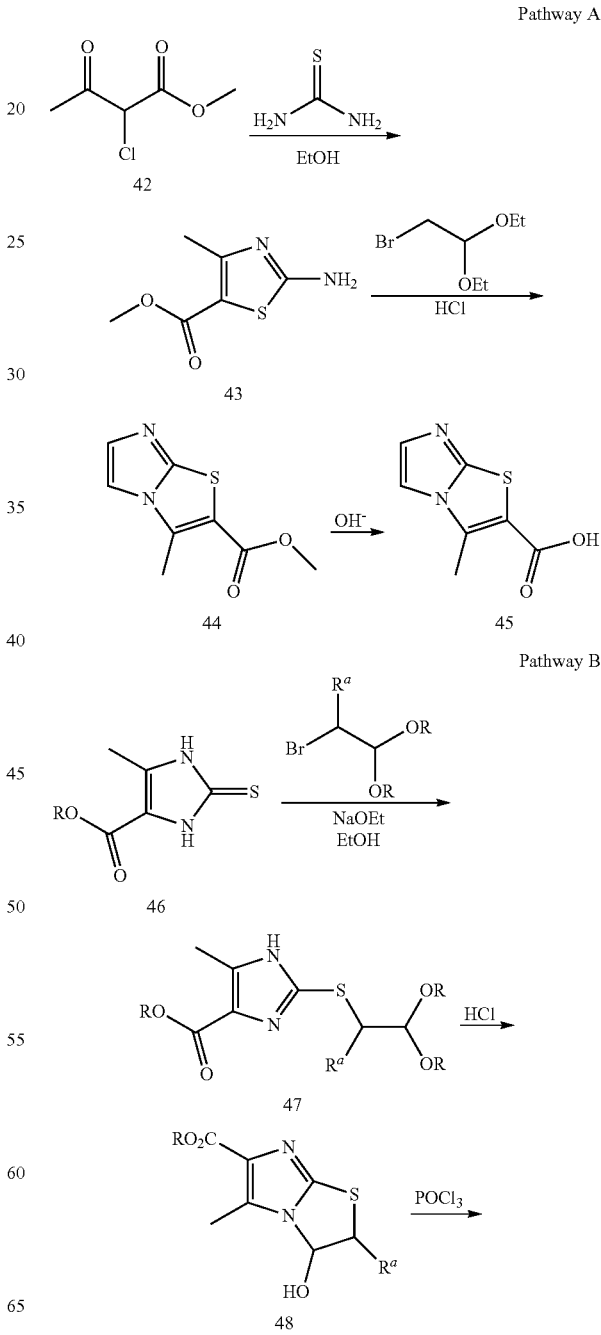

Derivatives of formula R¹—COOH wherein R¹ is imidazo [2,1-b]thiazole may be for instance synthesised according to one of the different pathways shown in scheme 7.

Following pathway A imidazo[2,1-b]thiazole-carboxylic acid derivatives may be synthesized starting from 2-chloro-

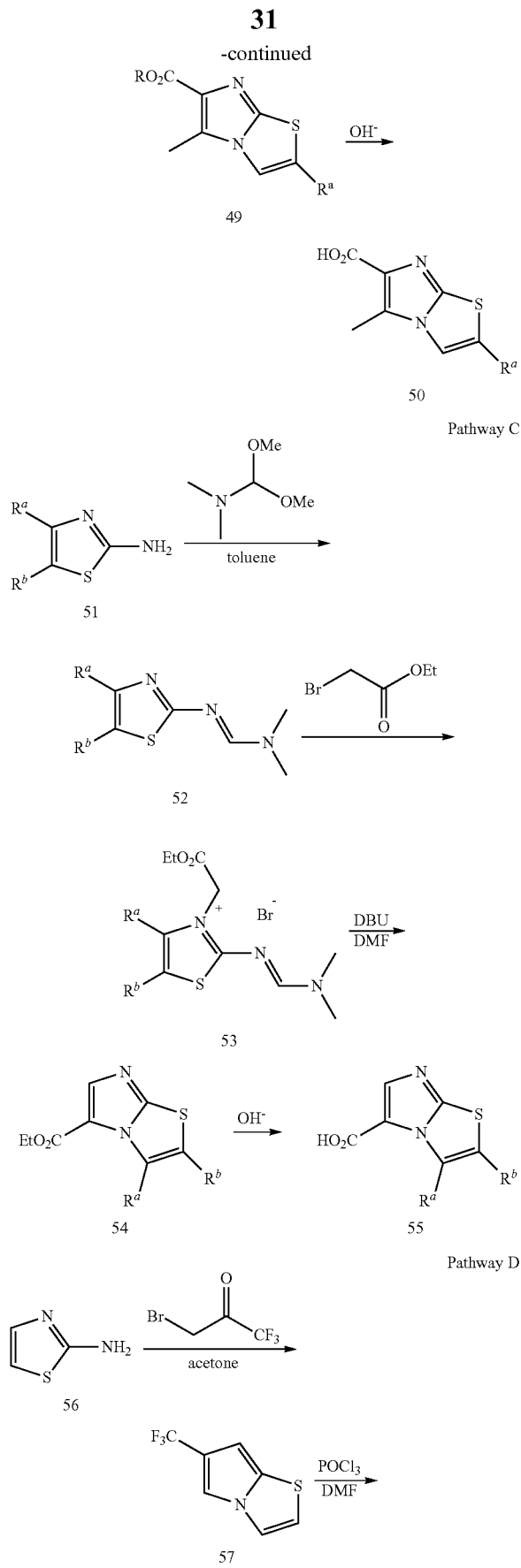

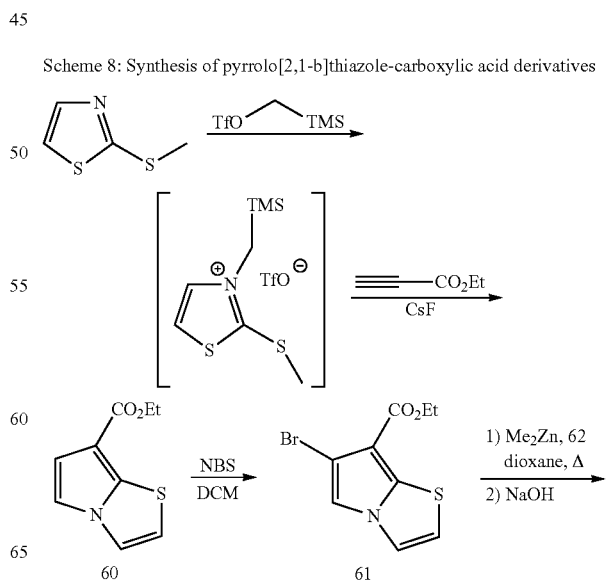

Alternatively (pathway B) the imidazole derivative (46) may be transferred to the acetal (47) by alkylation with a bromoacetaldehyde dialkyl acetal derivative in the presence of a base like sodium ethoxide. Cyclization under acidic conditions (e.g. aq. hydrochloric acid) and dehydration of the intermediate (48) with for instance phosphorus oxychloride may lead to ester (49) which may be transformed to the desired acid (50) by saponification with for instance NaOH in solvents like THF and MeOH.

In still an alternative procedure (pathway C) the respective amino-thiazole (51; commercially available) may be converted to the formamidine derivative (52) by heating (51) with N,N-dimethylformamide dimethylacetale in a solvent like toluene. After alkylation with ethyl bromoacetate the respective thiazolium bromide (53) may be cyclised with DBU to yield the ester (54) which may be saponified to the desired acid (55) with for instance NaOH in solvents like THF and MeOH.

Finally pathway D may start with the alkylation of 2-amino-thiazole with 3-bromo-1,1,1-trifluoroacetone to yield the trifluoromethyl-substituted imidazo[2,1-b]thiazole derivative (57) which may be formylated to the aldehyde (58) by reaction with phosphorus oxychloride in a solvent like DMF. By oxidation of aldehyde (58) with sodium chlorite the desired imidazo[2,1-b]thiazole-carboxylic acid (59) may be obtained. In analogy, the commercially available chlorinated aldehyde (58, being substituted with Cl instead of $CF_3$) may be oxidized to the corresponding acid.

Derivatives of formula $R^1$—COOH wherein $R^1$ is pyrrolo[2,1-b]thiazole were for instance synthesised according to the pathway shown in scheme 8.

Scheme 8: Synthesis of pyrrolo[2,1-b]thiazole-carboxylic acid derivatives

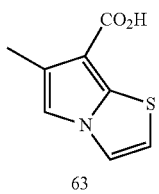

By reaction of 2-methylsulfanylthiazole with trimethylsilylmethyl trifluoromethanesulfonate followed by cyclisation of the resulting thiazolinium salt by reaction with ethyl propiolate in the presence of CsF, the pyrrolo[2,1-b]thiazole (60) can be obtained (Berry C. R. et al., *Organic Letters*, 2007, 9, 21, 4099-4102). Ester (61) was obtained by bromination of pyrrolo[2,1-b]thiazole-7-carboxylic acid ethyl ester (60) with NBS. In a Negishi-type coupling of (61) with dimethylzinc in the presence of catalytic amounts of [1,1'-Bis(diphenylphosphino)ferrocene]dichloropalladium(II) (62) the bromine atom was replaced by a methyl group to give after saponification with a base like NaOH in a solvent mixture like EtOH/water the acid derivative (63).

Derivatives of formula $R^1$—COOH wherein $R^1$ is benzothiazole were for instance synthesised according to the pathway shown in scheme 9.

is obtained which can be cyclised by treatment with an oxidizing reagent like bromine in an acid like acetic acid to 2-amino-benzothiazole derivatives (66). The amino group can be removed with, for instance, isoamyl nitrite to give ester derivatives (67) which can be saponified to acid derivatives (68) with a base like NaOH in solvents or mixtures of solvents like water, MeOH and THF.

Derivatives of formula $R^1$—COOH wherein $R^1$ is benzoxazole can be synthesised according to one of the pathways shown in scheme 10.

By reaction of 3-aminosalicylic acid (69) with the respective ortho-ester derivative the desired benzoxazole-7-carboxylic acid derivatives (70) can be obtained. The reaction may be catalyzed by addition of an acid like PTSA. The respective benzoxazole-4-carboxylic acid derivatives (72) can be synthesized by reaction of 2-amino-3-hydroxy-benzoic acid ethyl ester [(71), J. Reisch, G. M. K. B. Gunaherath *Monatshefte für Chemie*, 1988, 119, 1169-1178] with acetyl chloride in the presence of TEA and PPTS at elevated temperatures and subsequent saponification of the obtained ester with a base like potassium hydroxide in a solvent mixture like MeOH/water.

Scheme 9: Synthesis of benzothiazole-carboxylic acid derivatives

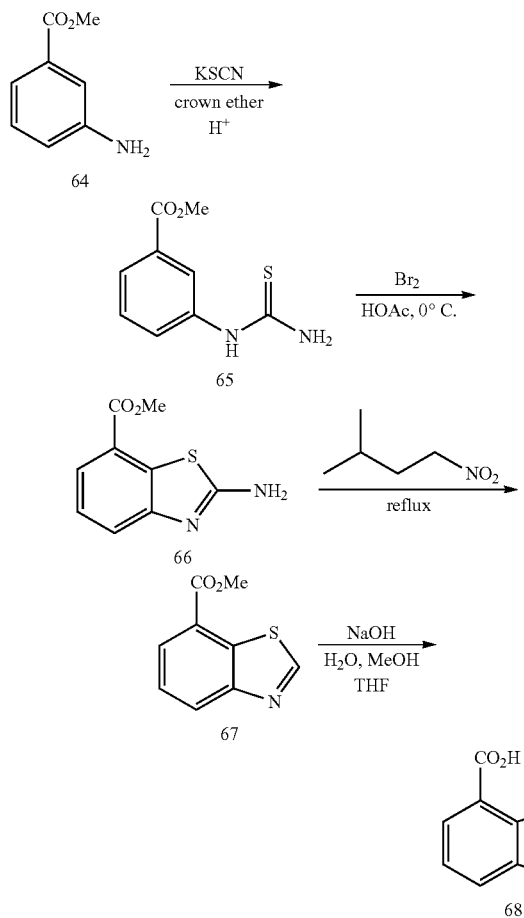

By reaction of 3-amino-benzoic acid methyl ester (64) with potassium thiocyanate the respective thiourea derivative (65)

Scheme 10: Synthesis of benzothiazole-carboxylic acid derivatives wherein R is methyl or ethyl and $R^a$ is hydrogen or methyl

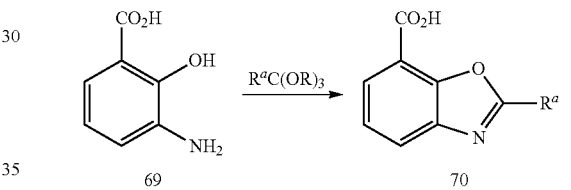

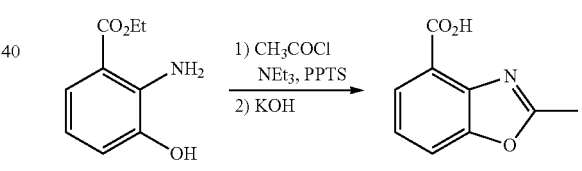

Scheme 11: Synthesis of oxazole-4-carboxylic acid derivatives, wherein R is methyl.

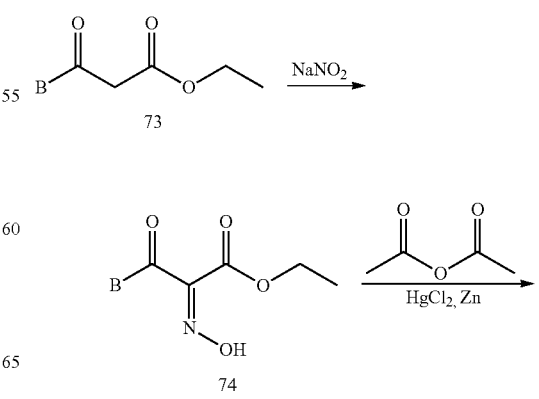

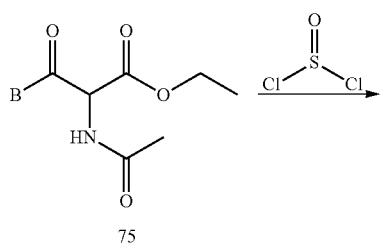

75

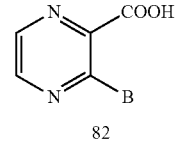

82

Suzuki-reaction under standard conditions of commercially available 3-chloro-pyrazine-2-carbonitrile (80) with commercially available aryl-boronic acids provides the corresponding 3-aryl-pyrazine-2-carbonitrile derivative 81 which is transformed to the desired carboxylic acid derivative 82 by hydrolysis of the nitrile under basic conditions in a solvent like MeOH.

Scheme 14: Alternative synthesis of final compounds with monoalkyl-amino-substituents in position 2 of the 5-arylthiazole substituent.

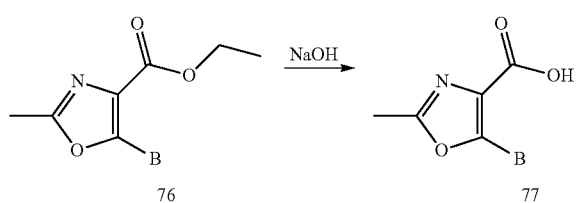

76 77

By reaction of a commercially available 3-oxo-propionic acid ester derivative 73 with an aq. solution sodium nitrite in presence of an acid such as glacial acetic acid the corresponding oxime derivative 74 can be obtained. The 2-acetamido-3-oxo-propionic acid ester derivative 75 can be synthesized from compounds of structure 74 using acetic anhydride in presence of an acid such as glacial acetic acid and catalytic amounts of metal chlorides such as mercury chloride and zinc powder. Cyclization to the corresponding corresponding oxazole-4 carboxylic acid ester derivative 76 can be achieved under dehydrating conditions such as SOCl$_2$ in CHCl$_3$. Saponification of the ester function using methods known in the art such as treatment with a base such as NaOH in solvent mixtures such as EtOH/water provides the corresponding oxazole-4 carboxylic acid derivative 77.

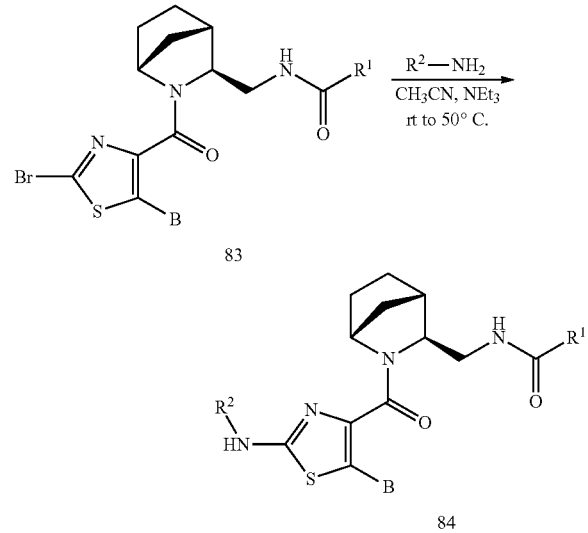

83

84

The 2-bromo-5-arylthiazole containing precursor 83 (prepared according to procedures given within this application) can be treated in a solvent like acetonitrile with an aq. solution of the respective primary amine to yield compounds 84.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA, diethylamine) and eluent B (hexane), at a flow rate of 0.8 to 150 mL/min.

Scheme 12: Synthesis of thiophene-2-carboxylic acid derivatives.

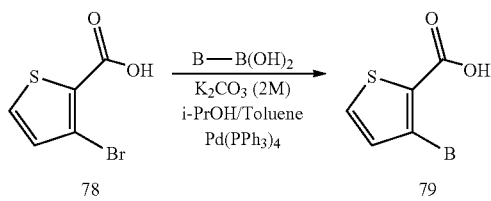

78 79

Suzuki-reaction under standard conditions of commercially available 3-bromo-thiophene-2-carboxylic acid (78) with commercially available aryl-boronic acids provides the corresponding 3-aryl-thiophene-2-carboxylic acid derivative 79.

Scheme 13: Synthesis of 3-aryl-pyrazine-2-carboxylic acid derivatives.

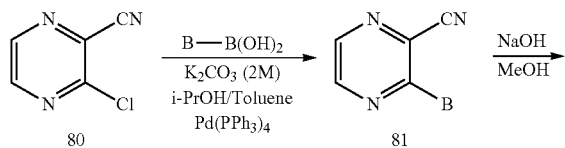

80 81

EXPERIMENTAL SECTION

Abbreviations (as used herein and in the decription before):

| | |
|---|---|
| aq | aqueous |
| Boc | tert-Butoxycarbonyl |
| BSA | Bovine serum albumine |

| | |
|---|---|
| CHO | Chinese hamster ovary |
| conc. | Concentrated |
| d | Day(s) |
| DBU | 1,8-Diazabicyclo[5.4.0]undec-7-ene |
| DCM | Dichloromethane |
| DIBAL | Diisobutylaluminium hydride |
| DIPEA | Diisopropylethylamine |
| DMAP | 4-Dimethylaminopyridine |
| DMF | N,N-Dimethylformamide |
| DMSO | Dimethylsulfoxide |
| eq | Equivalent(s) |
| ES | Electron spray |
| ether | Diethylether |
| EtOAc | Ethyl acetate |
| EtOH | ethanol |
| FCS | Foatal calf serum |
| FLIPR | Fluorescent imaging plate reader |
| h | Hour(s) |
| HBSS | Hank's balanced salt solution |
| HEPES | 4-(2-hydroxyethyl)-piperazine-l-ethanesulfonic acid |
| HPLC | High performance liquid chromatography |
| LC | Liquid chromatography |
| M | Molar(ity) |
| MeCN | Acetonitrile |
| MeOH | Methanol |
| min | Minute(s) |
| MS | Mass spectroscopy |
| NBS | N-Bromosuccinimide |
| PPTS | Pyridinium para-toluenesulfonate |
| prep. | Preparative |
| PTSA | para-Toluenesulfonic acid monohydrate |
| rt | Room temperature |
| sat | Saturated |
| $t_R$ | Retention time |
| TBME | tert-Butyl methyl ether |
| TBTU | O-Benzotriazol-1-yl-N,N,N',N'-tetramethyluronium tetrafluoroborate |
| TEA | Triethylamine |
| TFA | Trifluoroacetic acid |
| TFAA | Trifluoroacetic anhydride |
| THF | Tetrahydrofuran |

I—Chemistry

The following examples illustrate the preparation of pharmacologically active compounds of the invention but do not at all limit the scope thereof.

All temperatures are stated in ° C.

Compounds are characterized by:

$^1$H-NMR: 300 MHz Varian Oxford or 400 MHz Bruker Avance; chemical shifts are given in ppm relative to the solvent used; multiplicities: s=singlet, d=doublet, t=triplet, q=quartet, m=multiplet, b=broad, coupling constants are given in Hz;

LC-MS: Agilent 1100 series with DAD and MS detection (MS: Finnigan single quadrupole);

columns (4.6×50 mm, 5 µm): Zorbax SB-AQ, Zorbax Extend C18 or Waters XBridge C18;

conditions (if not otherwise stated the acidic gradient is used):

basic: eluent A: MeCN, eluent B: conc. NH$_3$ in water (1.0 mL/L), 5% to 95% CH$_3$CN, flow rate 4.5 mL/min;

acidic: eluent A: MeCN, eluent B: TFA in water (0.4 mL/L), 5% to 95% CH$_3$CN, flow rate 4.5 mL/min;

$t_R$ is given in min;

In case of a partial separation of rotamers, as seen for several examples of compounds of formula (I), two retention times are given.

Compounds are purified by column chromatography on silica gel or by preparative HPLC using RP-C$_{18}$ based columns with MeCN/water gradients and formic acid or ammonia additives.

A. PREPARATION OF BUILDING BLOCKS

A.1 Synthesis of thiazole-4-carboxylic acid derivatives

A.1.1 Synthesis of 3-chloro-2-oxo-propionic ester derivatives (general procedure)

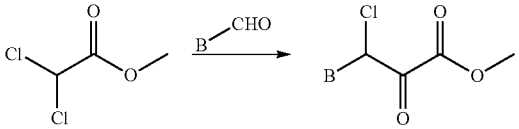

A solution of the respective aldehyde (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach rt, stirred over night and concentrated in vacuo. DCM and ice-cold water are added, the layers are separated and the aq. layer is extracted twice with DCM. The combined organic layers are washed with ice-cold water and brine, dried over MgSO$_4$ and concentrated in vacuo to give the desired 3-chloro-2-oxo-propionic ester derivative which is used without further purification.

3-Chloro-2-oxo-3-m-tolyl-propionic acid methyl ester
prepared by reaction of 3-methyl-benzaldehyde with methyl dichloroacetate.

3-Chloro-2-oxo-3-p-tolyl-propionic acid methyl ester
prepared by reaction of 4-methyl-benzaldehyde with methyl dichloroacetate.

3-Chloro-3-(3-methoxy-phenyl)-2-oxo-propionic acid methyl ester
prepared by reaction of 3-methoxy-benzaldehyde with methyl dichloro-acetate.

3-Chloro-3-(2-fluoro-phenyl)-2-oxo-propionic acid methyl ester
prepared by reaction of 2-fluoro-benzaldehyde with methyl dichloro-acetate.

3-Chloro-3-(3-fluoro-phenyl)-2-oxo-propionic acid methyl ester
prepared by reaction of 3-fluoro-benzaldehyde with methyl dichloroacetate.

3-Chloro-3-(4-fluoro-phenyl)-2-oxo-propionic acid methyl ester
prepared by reaction of 4-fluoro-benzaldehyde with methyl dichloroacetate.

3-Chloro-3-(3-chloro-phenyl)-2-oxo-propionic acid methyl ester
prepared by reaction of 3-chloro-benzaldehyde with methyl dichloro-acetate.

3-Chloro-2-oxo-3-(3-trifluoromethyl-phenyl)-propionic acid methyl ester
prepared by reaction of 3-trifluoromethyl-benzaldehyde with methyl dichloro-acetate.

3-Chloro-3-(3,4-dimethyl-phenyl)-2-oxo-propionic acid methyl ester
prepared by reaction of 3,4-dimethyl-benzaldehyde with methyl dichloro-acetate.

3-Chloro-3-(3,5-dimethyl-phenyl)-2-oxo-propionic acid methyl ester
prepared by reaction of 3,5-dimethyl-benzaldehyde with methyl dichloro-acetate.
3-(3-Bromo-4-fluoro-phenyl)-3-chloro-2-oxo-propionic acid methyl ester
prepared by reaction of 3-bromo-4-fluoro-benzaldehyde with methyl dichloro-acetate.
3-Chloro-3-(3,4-dichloro-phenyl)-2-oxo-propionic acid methyl ester
prepared by reaction of 3,4-dichloro-benzaldehyde with methyl dichloro-acetate.
3-Chloro-3-(3,4-difluoro-phenyl)-2-oxo-propionic acid methyl ester
prepared by reaction of 3,4-difluoro-benzaldehyde with methyl dichloro-acetate.
3-Chloro-3-(3-fluoro-4-methyl-phenyl)-2-oxo-propionic acid methyl ester
prepared by reaction of 3-fluoro-4-methyl-benzaldehyde with methyl dichloro-acetate.
3-Chloro-3-(3-fluoro-2-methyl-phenyl)-2-oxo-propionic acid methyl ester
prepared by reaction of 3-fluoro-2-methyl-benzaldehyde with methyl dichloro-acetate.
3-Chloro-2-oxo-3-phenyl-propionic acid methyl ester
prepared by reaction of benzaldehyde with methyl dichloro-acetate.
3-Chloro-3-(2,3-dichloro-phenyl)-2-oxo-propionic acid methyl ester
prepared by reaction of 2,3-dichloro-benzaldehyde with methyl dichloro-acetate.

A.1.2 Synthesis of thiazole-4-carboxylic acid methyl ester derivatives (general procedure)

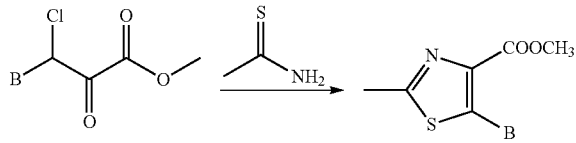

A solution of thioacetamide (132 mmol, 1.0 eq) in MeCN (250 mL) is added to a mixture of the respective 3-chloro-2-oxo-propionic ester derivative (132 mmol, 1.0 eq) and molecular sieves (4 Å, 12 g) in MeCN (60 mL). After stirring for 5 h the mixture is cooled in an ice-bath and the obtained precipitate is filtered off. The residue is washed with cold MeCN, dried, dissolved in MeOH (280 mL) and stirred at 50° C. for 6 h. The solvents are removed in vacuo to give the desired thiazole derivatives as a white solid.

2-methyl-5-m-tolyl-thiazole-4-carboxylic acid methyl ester
prepared by reaction of 3-chloro-2-oxo-3-m-tolyl-propionic acid methyl ester with thioacetamide. LC-MS: $t_R$=0.94 min; $[M+H]^+$=248.0.
2-methyl-5-p-tolyl-thiazole-4-carboxylic acid methyl ester
prepared by reaction of 3-chloro-2-oxo-3-p-tolyl-propionic acid methyl ester with thioacetamide. LC-MS: $t_R$=0.92 min; $[M+H]^+$=248.2.
5-(3-fluoro-phenyl)-2-methyl-thiazole-4-carboxylic acid methyl ester
prepared by reaction of 3-chloro-3-(3-fluoro-phenyl)-2-oxo-propionic acid methyl ester with thioacetamide. LC-MS: $t_R$=0.91 min; $[M+H]^+$=252.1.
5-(4-fluoro-phenyl)-2-methyl-thiazole-4-carboxylic acid methyl ester
prepared by reaction of 3-chloro-3-(4-fluoro-phenyl)-2-oxo-propionic acid methyl ester with thioacetamide. $^1$H-NMR (CDCl$_3$): δ=2.75 (s, 3H); 3.84 (s, 3H); 7.10 (m, 2H); 7.47 (m, 2H).
5-(3-chloro-phenyl)-2-methyl-thiazole-4-carboxylic acid methyl ester
prepared by reaction of 3-chloro-3-(3-chloro-phenyl)-2-oxo-propionic acid methyl ester with thioacetamide. LC-MS: $t_R$=0.95 min; $[M+H]^+$=268.0.
5-(3,4-dimethyl-phenyl)-2-methyl-thiazole-4-carboxylic acid methyl ester
prepared by reaction of 3-chloro-3-(3,4-dimethyl-phenyl)-2-oxo-propionic acid methyl ester with thioacetamide. LC-MS: $t_R$=0.96 min; $[M+H]^+$=262.3.
2-Methyl-5-phenyl-thiazole-4-carboxylic acid methyl ester
prepared by reaction of 3-chloro-2-oxo-3-phenyl-propionic acid methyl ester with thioacetamide. LC-MS: $t_R$=0.87 min; $[M+H]^+$=234.3.
5-(2,3-Dichloro-phenyl)-2-methyl-thiazole-4-carboxylic acid methyl ester
prepared by reaction of 3-chloro-3-(2,3-dichloro-phenyl)-2-oxo-propionic acid methyl ester with thioacetamide. LC-MS: $t_R$=0.97 min; $[M+H]^+$=302.2.
5-(3-Fluoro-2-methyl-phenyl)-2-methyl-thiazole-4-carboxylic acid methyl ester
prepared by reaction of 3-chloro-3-(3-fluoro-2-methyl-phenyl)-2-oxo-propionic acid methyl ester with thioacetamide. LC-MS: $t_R$=0.93 min; $[M+H]^+$=266.3.
5-(3-Bromo-4-fluoro-phenyl)-2-methyl-thiazole-4-carboxylic acid methyl ester
prepared by reaction of 3-(3-bromo-4-fluoro-phenyl)-3-chloro-2-oxo-propionic acid methyl ester with thioacetamide. LC-MS: $t_R$=0.95 min; $[M+H]^+$=330.2.
5-(3,4-Dichloro-phenyl)-2-methyl-thiazole-4-carboxylic acid methyl ester
prepared by reaction of 3-chloro-3-(3,4-dichloro-phenyl)-2-oxo-propionic acid methyl ester with thioacetamide. LC-MS: $t_R$=0.99 min; $[M+H]^+$=302.2.
5-(3,4-Difluoro-phenyl)-2-methyl-thiazole-4-carboxylic acid methyl ester
prepared by reaction of 3-chloro-3-(3,4-difluoro-phenyl)-2-oxo-propionic acid methyl ester with thioacetamide. LC-MS: $t_R$=0.92 min; $[M+H]^+$=270.3.
5-(3-Fluoro-4-methyl-phenyl)-2-methyl-thiazole-4-carboxylic acid methyl ester
prepared by reaction of 3-chloro-3-(3-fluoro-4-methyl-phenyl)-2-oxo-propionic acid methyl ester with thioacetamide. LC-MS: $t_R$=1.00 min; $[M+H]^+$=266.0.
5-(3,5-Dimethyl-phenyl)-2-methyl-thiazole-4-carboxylic acid methyl ester
prepared by reaction of 3-chloro-3-(3,5-dimethyl-phenyl)-2-oxo-propionic acid methyl ester with thioacetamide. LC-MS: $t_R$=0.97 min; $[M+H]^+$=262.3.

A.1.3 Synthesis of 2-cyclopropyl-thiazole-4-carboxylic acid methyl ester derivatives Synthesis of cyclopropanecarbothioic acid amide 2,4-Bis-(4-methoxyphenyl)-1,3-dithia-2,4-diphosphetane 2,4-disulfide (Lawesson reagent, 173 mmol) is added to a mixture of cyclopropanecarboxamide (173 mmol) and Na$_2$CO$_3$ (173 mmol) in THF (750 mL). The reaction mixture is stirred at reflux for 3 h, concentrated in vacuo and diluted with ether (500 mL) and water (500 mL). The layers are separated and the aq. layer is extracted with ether (250 mL). The combined organic layers are washed with brine (100 mL), dried over MgSO$_4$ and concentrated in vacuo to give a crude product which is used without further purification. $^1$H-NMR (DMSO-d$_6$): δ=0.81-0.88 (m, 2H); 0.96-1.00 (m, 2H); 2.00 (tt, J=8.0 Hz, J=4.3 Hz, 1H); 9.23 (bs, 1H); 9.33 (bs, 1H).

Synthesis of 2-cyclopropyl-thiazole-4-carboxylic acid methyl ester derivatives (general procedure)

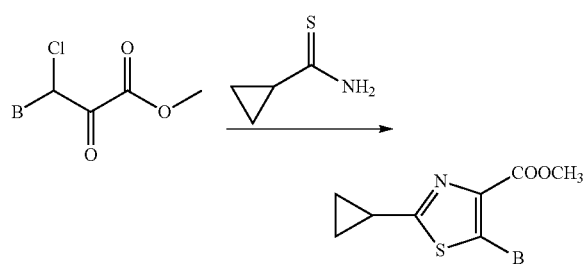

A solution of cyclopropanecarbothioic acid amide (33.9 mmol, 1.0 eq) in MeCN (45 mL) is added to a mixture of the respective 3-chloro-2-oxo-propionic ester derivative (33.9 mmol, 1.0 eq) and NaHCO$_3$ (102 mmol, 3.0 eq) in MeCN (45 mL). After stirring for 2 d at rt the mixture is concentrated in vacuo and the residue is diluted with EtOAc (150 mL) and water (150 mL). The layers are separated and the aq. layer is extracted with EtOAc (100 mL). The combined organic layers are washed with brine (100 mL), dried over MgSO$_4$ and concentrated in vacuo. The residue is dissolved in MeOH (70 mL) and treated with concentrated H$_2$SO$_4$ (0.18 mL). The mixture is stirred at 60° C. for 16 h and concentrated in vacuo to give the respective crude product which is used without further purification.
2-Cyclopropyl-5-phenyl-thiazole-4-carboxylic acid methyl ester
prepared by reaction of 3-chloro-2-oxo-3-phenyl-propionic acid methyl ester with cyclopropanecarbothioic acid amide. LC-MS: t$_R$=0.99 min; [M+H]$^+$=260.5.
2-Cyclopropyl-5-(4-methyl-phenyl)-thiazole-4-carboxylic acid methyl ester
prepared by reaction of 3-chloro-2-oxo-3-(4-methyl-phenyl)-propionic acid methyl ester with cyclopropanecarbothioic acid amide. LC-MS: t$_R$=0.99 min; [M+H]$^+$=260.5.

A.1.4 Synthesis of 2-amino-thiazole-4-carboxylic acid methyl ester derivatives (general procedure)

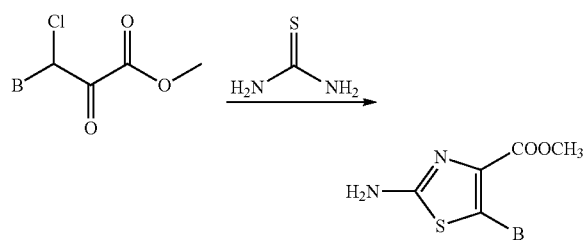

A solution of the respective 3-chloro-2-oxo-propionic ester derivative (22.1 mmol, 1.0 eq) in acetone (25 mL) is added to a suspension of thiourea (22.1 mmol, 1.0 eq) in acetone (45 mL). The mixture is heated to 57° C. (bath temperature), stirred for 24 h and concentrated to half of the volume. The obtained suspension is filtered and the residue is washed with acetone. After drying the desired amino-thiazole derivative is obtained as a solid.
2-Amino-5-(3-fluoro-phenyl)-thiazole-4-carboxylic acid methyl ester
prepared by reaction of 3-chloro-3-(3-fluoro-phenyl)-2-oxo-propionic acid methyl ester with thiourea. LC-MS: t$_R$=0.78 min; [M+H]$^+$=252.9.
2-Amino-5-(2-fluoro-phenyl)-thiazole-4-carboxylic acid methyl ester
prepared by reaction of 3-chloro-3-(2-fluoro-phenyl)-2-oxo-propionic acid methyl ester with thiourea. LC-MS: t$_R$=0.76 min; [M+H]$^+$=253.2.
2-Amino-5-(4-fluoro-phenyl)-thiazole-4-carboxylic acid methyl ester
prepared by reaction of 3-chloro-3-(4-fluoro-phenyl)-2-oxo-propionic acid methyl ester with thiourea. LC-MS: t$_R$=0.75 min; [M+H]$^+$=253.2.
2-Amino-5-(3-methoxy-phenyl)-thiazole-4-carboxylic acid methyl ester
prepared by reaction of 3-chloro-3-(3-methoxy-phenyl)-2-oxo-propionic acid methyl ester with thiourea. LC-MS: t$_R$=0.75 min; [M+H]$^+$=265.3.
2-Amino-5-(3-chloro-phenyl)-thiazole-4-carboxylic acid methyl ester
prepared by reaction of 3-chloro-3-(3-chloro-phenyl)-2-oxo-propionic acid methyl ester with thiourea. LC-MS: t$_R$=0.82 min; [M+H]$^+$=269.2.
2-Amino-5-(3-trifluoromethyl-phenyl)-thiazole-4-carboxylic acid methyl ester
prepared by reaction of 3-chloro-3-(3-trifluoromethyl-phenyl)-2-oxo-propionic acid methyl ester with thiourea. LC-MS: t$_R$=0.86 min; [M+H]$^+$=303.3.
2-Amino-5-phenyl-thiazole-4-carboxylic acid methyl ester
prepared by reaction of 3-chloro-2-oxo-3-phenyl-propionic acid methyl ester with thiourea. LC-MS: t$_R$=0.77 min; [M+H]$^+$=235.1.

A.1.5 Synthesis of 2-bromo-thiazole-4-carboxylic acid methyl ester derivatives (general procedure)

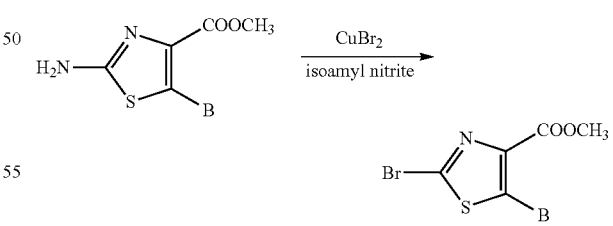

At 15° C. under an atmosphere of nitrogen the respective 2-amino-thiazole-4-carboxylic acid methyl ester (7.10 mmol) is added portionwise to a mixture of CuBr$_2$ (7.10 mmol) and isoamyl nitrite (10.6 mmol) in MeCN (30 mL). The mixture is stirred for 20 min at 15° C., for 30 min at 40° C. and for 90 min at 65° C. The solvents are removed in vacuo and the crude product is either purified by flash chromatography (DCM/MeOH or EtOAc/heptane) or used without further purification.

2-Bromo-5-(2-fluoro-phenyl)-thiazole-4-carboxylic acid methyl ester
prepared by reaction of 2-amino-5-(2-fluoro-phenyl)-thiazole-4-carboxylic acid methyl ester with CuBr$_2$ and isoamyl nitrite. LC-MS: $t_R$=0.96 min; [M+H]$^+$=316.1.

2-Bromo-5-(3-fluoro-phenyl)-thiazole-4-carboxylic acid methyl ester
prepared by reaction of 2-amino-5-(3-fluoro-phenyl)-thiazole-4-carboxylic acid methyl ester with CuBr$_2$ and isoamyl nitrite. LC-MS: $t_R$=1.08 min; [M+H]$^+$=316.0.

2-Bromo-5-(4-fluoro-phenyl)-thiazole-4-carboxylic acid methyl ester
prepared by reaction of 2-amino-5-(4-fluoro-phenyl)-thiazole-4-carboxylic acid methyl ester with CuBr$_2$ and isoamyl nitrite. LC-MS: $t_R$=0.97 min; [M+H]$^+$=316.1.

2-Bromo-5-(3-methoxy-phenyl)-thiazole-4-carboxylic acid methyl ester
prepared by reaction of 2-amino-5-(3-methoxy-phenyl)-thiazole-4-carboxylic acid methyl ester with CuBr$_2$ and isoamyl nitrite. LC-MS: $t_R$=0.97 min; [M+H]$^+$=328.2.

2-Bromo-5-(3-chloro-phenyl)-thiazole-4-carboxylic acid methyl ester
prepared by reaction of 2-amino-5-(3-chloro-phenyl)-thiazole-4-carboxylic acid methyl ester with CuBr$_2$ and isoamyl nitrite. LC-MS: $t_R$=1.00 min; [M+H]$^+$=332.2.

2-Bromo-5-(3-trifluoromethyl-phenyl)-thiazole-4-carboxylic acid methyl ester
prepared by reaction of 2-amino-5-(3-trifluoromethyl-phenyl)-thiazole-4-carboxylic acid methyl ester with CuBr$_2$ and isoamyl nitrite. LC-MS: $t_R$=1.03 min; [M+H]$^+$=366.2.

2-Bromo-5-phenyl-thiazole-4-carboxylic acid methyl ester
prepared by reaction of 2-amino-5-phenyl-thiazole-4-carboxylic acid methyl ester with CuBr$_2$ and isoamyl nitrite. LC-MS: $t_R$=1.07 min; [M+H]$^+$=297.9.

A.1.6 Synthesis of thiazole-4-carboxylic acid methyl ester derivatives lacking a substituent in 2-position (general procedure)

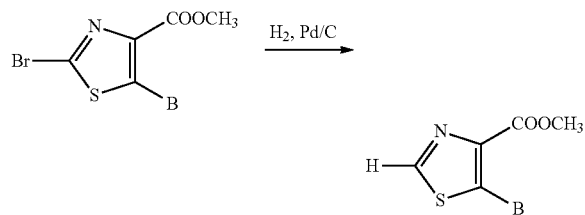

A solution/suspension of the respective 2-bromo-thiazole-4-carboxylic acid methyl ester (3.17 mmol) in EtOH (20 mL) is added to a suspension of Pd/C (600 mg, 10%) in EtOH (20 mL) and stirred under a hydrogen atmosphere (1 bar) for 18 h. After filtration through celite and removal of the solvents the desired product is obtained which is used without further purification.

5-(2-Fluoro-phenyl)-thiazole-4-carboxylic acid methyl ester
prepared by hydrogenation of 2-bromo-5-(2-fluoro-phenyl)-thiazole-4-carboxylic acid methyl ester. LC-MS: $t_R$=0.91 min; [M+H]$^+$=238.0.

5-(4-Fluoro-phenyl)-thiazole-4-carboxylic acid methyl ester
prepared by hydrogenation of 2-bromo-5-(4-fluoro-phenyl)-thiazole-4-carboxylic acid methyl ester. LC-MS: $t_R$=0.92 min; [M+H]$^+$=238.1.

5-(3-Methoxy-phenyl)-thiazole-4-carboxylic acid methyl ester
prepared by hydrogenation of 2-bromo-5-(3-methoxy-phenyl)-thiazole-4-carboxylic acid methyl ester. LC-MS: $t_R$=0.92 min; [M+H]$^+$=250.1.

5-(3-Chloro-phenyl)-thiazole-4-carboxylic acid methyl ester
prepared by hydrogenation of 2-bromo-5-(3-chloro-phenyl)-thiazole-4-carboxylic acid methyl ester. LC-MS: $t_R$=0.91 min; [M+H]$^+$=253.9.

5-(3-Trifluoromethyl-phenyl)-thiazole-4-carboxylic acid methyl ester
prepared by hydrogenation of 2-bromo-5-(3-trifluoromethyl-phenyl)-thiazole-4-carboxylic acid methyl ester. LC-MS: $t_R$=0.99 min; [M+H]$^+$=288.0.

A.1.7 Synthesis of thiazole-4-carboxylic acid derivatives (general procedure)

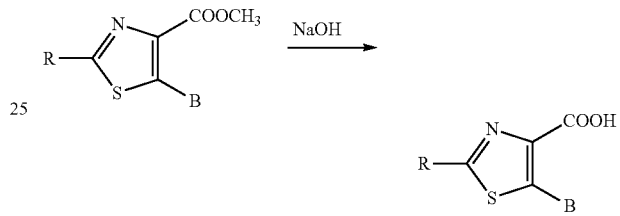

A solution of the respective thiazole-4-carboxylic acid ester (96.2 mmol) in a mixture of THF (150 mL) and either MeOH or isopropanol (50 mL) is treated with an aq. NaOH solution (1.0 M, 192 mL). After stirring for 3 h a white suspension is formed and the organic volatiles are removed in vacuo. The remaining mixture is diluted with water (100 mL), cooled in an ice-bath and made acidic (pH=3-4) by addition of aq. HCl solution (1.0 M). The suspension is filtered and the residue is washed with cold water. After drying the desired acid is obtained as a white solid.

2-methyl-5-m-tolyl-thiazole-4-carboxylic acid
prepared by saponification of 2-methyl-5-m-tolyl-thiazole-4-carboxylic acid methyl ester. LC-MS: $t_R$=0.83 min; [M+H]$^+$=234.0.

2-methyl-5-p-tolyl-thiazole-4-carboxylic acid
prepared by saponification of 2-methyl-5-p-tolyl-thiazole-4-carboxylic acid methyl ester. LC-MS: $t_R$=0.83 min; [M+H]$^+$=234.0.

5-(3-fluoro-phenyl)-2-methyl-thiazole-4-carboxylic acid
prepared by saponification of 5-(3-fluoro-phenyl)-2-methyl-thiazole-4-carboxylic acid methyl ester. LC-MS: $t_R$=0.82 min; [M+H]$^+$=238.1.

5-(4-fluoro-phenyl)-2-methyl-thiazole-4-carboxylic acid
prepared by saponification of 5-(4-fluoro-phenyl)-2-methyl-thiazole-4-carboxylic acid methyl ester. $^1$H-NMR (DMSO-d$_6$): δ=2.67 (s, 3H); 7.27 (m, 2H); 7.53 (m, 2H); 12.89 (bs, 1H).

5-(3-chloro-phenyl)-2-methyl-thiazole-4-carboxylic acid
prepared by saponification of 5-(3-chloro-phenyl)-2-methyl-thiazole-4-carboxylic acid methyl ester. LC-MS: $t_R$=0.84 min; [M+H]$^+$=254.0.

5-(3,4-dimethyl-phenyl)-2-methyl-thiazole-4-carboxylic acid
prepared by saponification of 5-(3,4-dimethyl-phenyl)-2-methyl-thiazole-4-carboxylic acid methyl ester. LC-MS: $t_R$=0.86 min; [M+H]$^+$=248.3.

2-amino-5-(3-fluoro-phenyl)-thiazole-4-carboxylic acid prepared by saponification of 2-amino-5-(3-fluoro-phenyl)-thiazole-4-carboxylic acid methyl ester. LC-MS: $t_R$=0.62 min; [M+H]$^+$=239.1.

2-Methyl-5-phenyl-thiazole-4-carboxylic acid
prepared by saponification of 2-methyl-5-phenyl-thiazole-4-carboxylic acid methyl ester. LC-MS: $t_R$=0.77 min; [M+H]$^+$=220.3.

5-(2,3-Dichloro-phenyl)-2-methyl-thiazole-4-carboxylic acid
prepared by saponification of 5-(2,3-dichloro-phenyl)-2-methyl-thiazole-4-carboxylic acid methyl ester. LC-MS: $t_R$=0.86 min; [M+H]$^+$=288.2.

5-(3-Fluoro-2-methyl-phenyl)-2-methyl-thiazole-4-carboxylic acid
prepared by saponification of 5-(3-fluoro-2-methyl-phenyl)-2-methyl-thiazole-4-carboxylic acid methyl ester. LC-MS: $t_R$=0.83 min; [M+H]$^+$=252.2.

5-(3-Bromo-4-fluoro-phenyl)-2-methyl-thiazole-4-carboxylic acid
prepared by saponification of 5-(3-bromo-4-fluoro-phenyl)-2-methyl-thiazole-4-carboxylic acid methyl ester. LC-MS: $t_R$=0.86 min; [M+H]$^+$=316.2.

5-(3,4-Dichloro-phenyl)-2-methyl-thiazole-4-carboxylic acid
prepared by saponification of 5-(3,4-dichloro-phenyl)-2-methyl-thiazole-4-carboxylic acid methyl ester. LC-MS: $t_R$=0.88 min; [M+H]$^+$=288.2.

5-(3,4-Difluoro-phenyl)-2-methyl-thiazole-4-carboxylic acid
prepared by saponification of 5-(3,4-difluoro-phenyl)-2-methyl-thiazole-4-carboxylic acid methyl ester. LC-MS: $t_R$=0.82 min; [M+H]$^+$=256.3.

5-(3-Fluoro-4-methyl-phenyl)-2-methyl-thiazole-4-carboxylic acid
prepared by saponification of 5-(3-fluoro-4-methyl-phenyl)-2-methyl-thiazole-4-carboxylic acid methyl ester. LC-MS: $t_R$=0.89 min; [M+H]$^+$=252.0.

5-(3,5-Dimethyl-phenyl)-2-methyl-thiazole-4-carboxylic acid
prepared by saponification of 5-(3,5-dimethyl-phenyl)-2-methyl-thiazole-4-carboxylic acid methyl ester. LC-MS: $t_R$=0.86 min; [M+H]$^+$=248.3.

5-(3-Trifluoromethyl-phenyl)-2-methyl-thiazole-4-carboxylic acid
prepared by saponification of 5-(3-trifluoromethyl-phenyl)-2-methyl-thiazole-4-carboxylic acid methyl ester. LC-MS: $t_R$=0.91 min; [M+H]$^+$=288.03.

5-(2-Fluoro-phenyl)-thiazole-4-carboxylic acid
prepared by saponification of 5-(2-fluoro-phenyl)-thiazole-4-carboxylic acid methyl ester. LC-MS: $t_R$=0.80 min; [M+H]$^+$=224.1.

5-(3-Methoxy-phenyl)-thiazole-4-carboxylic acid
prepared by saponification of 5-(3-methoxy-phenyl)-thiazole-4-carboxylic acid methyl ester. LC-MS: $t_R$=0.81 min; [M+H]$^+$=236.1.

5-(3-Chloro-phenyl)-thiazole-4-carboxylic acid
prepared by saponification of 5-(3-chloro-phenyl)-thiazole-4-carboxylic acid methyl ester. LC-MS: $t_R$=0.85 min; [M+H]$^+$=240.0.

5-(3-Trifluoromethyl-phenyl)-thiazole-4-carboxylic acid
prepared by saponification of 5-(3-trifluoromethyl-phenyl)-thiazole-4-carboxylic acid methyl ester. LC-MS: $t_R$=0.89 min; [M+H]$^+$=274.0.

5-(4-Fluoro-phenyl)-thiazole-4-carboxylic acid
prepared by saponification of 5-(4-fluoro-phenyl)-thiazole-4-carboxylic acid methyl ester. LC-MS: $t_R$=0.80 min; [M+H]$^+$=224.1.

2-Cyclopropyl-5-phenyl-thiazole-4-carboxylic acid
prepared by saponification of 2-cyclopropyl-5-phenyl-thiazole-4-carboxylic acid methyl ester. LC-MS: $t_R$=0.91 min; [M+H]$^+$=246.4.

2-Cyclopropyl-5-p-tolyl-thiazole-4-carboxylic acid
prepared by saponification of 2-cyclopropyl-5-p-tolyl-thiazole-4-carboxylic acid methyl ester. LC-MS: $t_R$=0.91 min; [M+H]$^+$=260.03.

2-Cyclopropyl-5-(2-fluoro-phenyl)-thiazole-4-carboxylic acid
prepared by saponification of 2-cyclopropyl-5-(2-fluoro-phenyl)-thiazole-4-carboxylic acid methyl ester. LC-MS: $t_R$=0.91 min; [M+H]$^+$=264.27.

2-Cyclopropyl-5-m-tolyl-thiazole-4-carboxylic acid
prepared by saponification of 2-cyclopropyl-5-m-tolyl-thiazole-4-carboxylic acid methyl ester. LC-MS: $t_R$=0.90 min; [M+H]$^+$=260.23.

2-Cyclopropyl-5-(3-fluoro-4-methyl-phenyl)-thiazole-4-carboxylic acid
prepared by saponification of 2-cyclopropyl-5-(3-fluoro-4-methyl-phenyl)-thiazole-4-carboxylic acid methyl ester. LC-MS: $t_R$=0.97 min; [M+H]$^+$=278.06.

2-Cyclopropyl-5-(3-fluoro-phenyl)-thiazole-4-carboxylic acid
prepared by saponification of 2-cyclopropyl-5-(3-fluoro-phenyl)-thiazole-4-carboxylic acid methyl ester. LC-MS: $t_R$=0.92 min; [M+H]$^+$=264.01.

A.1.8.1 Synthesis of 2-dimethylamino-thiazole-4-carboxylic acid derivatives (general procedure)

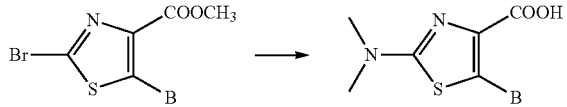

An aq. solution of dimethylamine (40%, 13 mL) is added to a solution of the respective 2-bromo-thiazole-4-carboxylic acid methyl ester derivative (6.71 mmol) in MeCN (38 mL). After 2 h an additional portion of an aq. dimethylamine solution (40%, 13 mL) is added. After stirring at rt for 2 d THF (13.6 mL), MeOH (6.8 mL) and aq. NaOH solution (1.0 M, 13.4 mL) are added successively and the mixture is stirred for 16 h. The solvents are removed in vacuo and the residue is diluted with water (30 mL). The suspension is made acidic (pH 3) by addition of aq. citric acid (10%) and extracted three times with EtOAc. The combined organic layers are washed twice with brine, dried over MgSO$_4$ and concentrated in vacuo to give the desired acid which is used without further purification.

2-Dimethylamino-5-(3-fluoro-phenyl)-thiazole-4-carboxylic acid
prepared by reaction of 2-bromo-5-(3-fluoro-phenyl)-thiazole-4-carboxylic acid methyl ester with dimethylamine. LC-MS: $t_R$=0.87 min; [M+H]$^+$=267.0.

2-Dimethylamino-5-phenyl-thiazole-4-carboxylic acid
prepared by reaction of 2-bromo-5-phenyl-thiazole-4-carboxylic acid methyl ester with dimethylamine. LC-MS: $t_R$=0.81 min; [M+H]$^+$=249.1.

2-Dimethylamino-5-(3,4-dimethyl-phenyl)-thiazole-4-carboxylic acid
prepared by reaction of 2-bromo-5-(3,4-dimethyl-phenyl)-thiazole-4-carboxylic acid methyl ester with dimethylamine. LC-MS: $t_R$=0.89 min; [M+H]$^+$=277.3.

5-(3-Chloro-phenyl)-2-dimethylamino-thiazole-4-carboxylic acid prepared by reaction of 2-bromo-5-(3-chloro-phenyl)-thiazole-4-carboxylic acid methyl ester with dimethylamine. LC-MS: $t_R$=0.90 min; [M+H]$^+$=283.21.

2-Dimethylamino-5-(2-fluoro-phenyl)-thiazole-4-carboxylic acid prepared by reaction of 2-bromo-5-(2-fluoro-phenyl)-thiazole-4-carboxylic acid methyl ester with dimethylamine. LC-MS: $t_R$=0.84 min; [M+H]$^+$=267.42.

2-Dimethylamino-5-(4-fluoro-phenyl)-thiazole-4-carboxylic acid prepared by reaction of 2-bromo-5-(4-fluoro-phenyl)-thiazole-4-carboxylic acid methyl ester with dimethylamine. LC-MS: $t_R$=0.83 min; [M+H]$^+$=267.27.

2-Dimethylamino-5-(3-methoxy-phenyl)-thiazole-4-carboxylic acid prepared by reaction of 2-bromo-5-(3-methoxy-phenyl)-thiazole-4-carboxylic acid methyl ester with dimethylamine. LC-MS: $t_R$=0.83 min; [M+H]$^+$=279.25.

According to the procedure described above, the following 2-amino-5-aryl-thiazole-4-carboxylic acid derivatives were prepared:

5-(3-Chloro-phenyl)-2-diethylamino-thiazole-4-carboxylic acid prepared by reaction of 2-bromo-5-(3-chloro-phenyl)-thiazole-4-carboxylic acid methyl ester with diethylamine. LC-MS: $t_R$=0.92 min; [M+H]$^+$=311.21.

5-(3-Chloro-phenyl)-2-ethylmethylamino-thiazole-4-carboxylic acid prepared by reaction of 2-bromo-5-(3-chloro-phenyl)-thiazole-4-carboxylic acid methyl ester with ethylmethylamine. LC-MS: $t_R$=0.90 min; [M+H]$^+$=297.22.

A.1.8.2. Synthesis of 2-alkoxy-thiazole-4-carboxylic acid derivatives (general procedure)

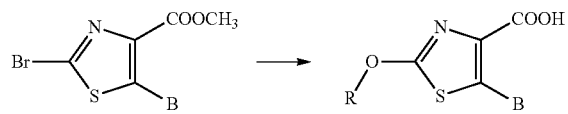

The alcohol (3 mmol) is slowly added to a suspension of sodium hydride (3 mmol) in THF (4 ml) and stirring is continued for 15 min at rt followed by the addition of a solution of the respective 2-bromo-thiazole-4-carboxylic acid methyl ester derivative (1.5 mmol) in THF/DMF (6 ml/0.7 ml). After stirring at rt for 2 d THF (13.6 mL), MeOH (6.8 mL) and aq. NaOH solution (1.0 M, 13.4 mL) are added successively and the mixture is stirred for 16 h. The solvents are removed in vacuo and the residue is diluted with water (30 mL). The suspension is made acidic (pH 3) by addition of aq. citric acid (10%) and extracted three times with EtOAc. The combined organic layers are washed twice with brine, dried over MgSO$_4$ and concentrated in vacuo to give the desired acid which is used without further purification.

5-(3-Chloro-phenyl)-2-methoxy-thiazole-4-carboxylic acid LC-MS: $t_R$=0.93 min; [M+H]$^+$=271.24.

5-(3-Chloro-phenyl)-2-(2-methoxy-ethoxy)-thiazole-4-carboxylic acid

LC-MS: $t_R$=0.95 min; [M+H]$^+$=314.00.

5-(3-Chloro-phenyl)-2-ethoxy-thiazole-4-carboxylic acid

LC-MS: $t_R$=0.93 min; [M+H]$^+$=284.01.

A.1.9 Synthesis of 2-methyl-oxazole-4-carboxylic acid derivatives

A.1.9.1 Synthesis of 2-acetylamino-3-oxo-propionic acid methyl ester derivatives (general procedure)

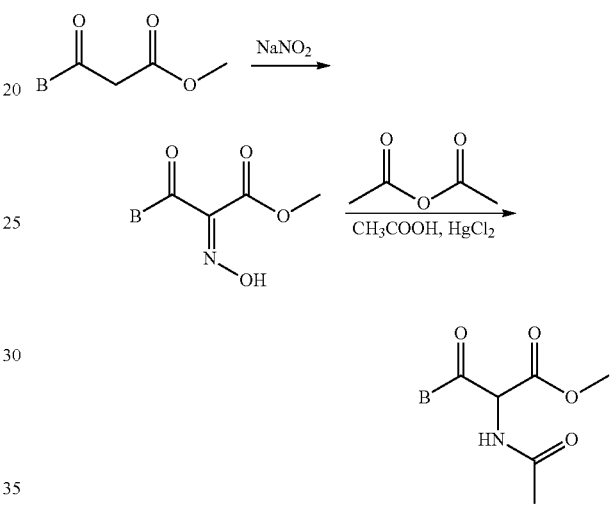

A solution of the respective 3-oxo-propionic acid methyl ester derivative (4.8 mmol, 1.0 eq.) in glacial acetic acid (1.9 mL) was cooled to 10° C. and at this temperature was added a solution of NaNO$_2$ (5.6 mmol, 1.16 eq.) in water (0.68 mL). After the addition was complete (15 min), the solution was allowed to warm to rt and stirred for 2 h. Then the solution was poured into water (10 mL) and after a few minutes crystals begun to appear. This suspension was cooled in an ice-bath and crystals were collected by filtration. The cake was washed several times with cold water and the water was removed by the azeotrope of toluene-water in vacuo to give 2-hydroxy-imino-3-oxo-propionic acid methyl ester derivatives which were dissolved in a mixture of acetic anhydride (1.4 mL) and glacial acetic acid (1.8 mL). To this solution was added sodium acetate (0.296 mmol, 0.06 eq.) and HgCl$_2$ (0.01 mmol, 0.002 eq.). The mixture was refluxed for 1 h, then cooled to rt and filtered. The solid was rinsed with ether, the organic filtrate was recovered, washed 3 times with water and one time with 1M aq. K$_2$CO$_3$. The organic layer was dried over MgSO4, filtered and concentrated. The crude products were purified by flash chromatography to afford the corresponding 2-acetylamino-3-oxo-propionic acid methyl ester derivatives.

2-Acetylamino-3-oxo-3-(3-trifluoromethoxy-phenyl)-propionic acid methyl ester prepared according to general procedure A.1.9.1 from 3-oxo-3-(3-trifluoromethoxy-phenyl)-propionic acid methyl ester.

A.1.9.2 Synthesis of 2-methyl-oxazole-4-carboxylic acid derivatives (general procedure)

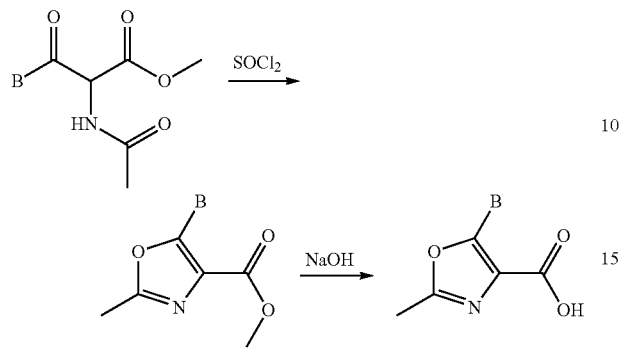

A solution of the respective 2-acetylamino-3-oxo-propionic acid methyl ester derivative (0.63 mmol, 1.0 eq.) in CHCl₃ (0.4 mL) was cooled to 0° C. in an ice/NaCl bath. SOCl₂ (0.88 mmol, 1.4 eq.) was added to the stirred solution and the temperature was maintained at 0° C. for 30 minutes. Then the solution was stirred and refluxed for one hour. Another 0.25 eq. of SOCl₂ was added and the reaction mixture was refluxed for another hour. The excess SOCl₂ was quenched with 1M aq. K₂CO₃. The aq. layer was extracted twice with ether. The combined organic phases were washed once with water and dried over MgSO₄, filtered and concentrated yielding the corresponding 2-methyl-oxazole-4-carboxylic acid methyl ester derivative. The respective 2-methyl-oxazole-4-carboxylic acid methyl ester derivative was dissolved in a mixture of EtOH (0.7 ml) and 2N aq. NaOH (0.7 mL, 2.5 eq.). The mixture was stirred at rt for 2 hours. The reaction mixture was washed once with ether and this organic layer was discarded. The aq. layer was then acidified with conc. HCl and extracted twice with ether. Both organic layers were combined, dried over MgSO₄ and concentrated in vacuo to afford the corresponding 2-methyl-oxazole-4-carboxylic acid derivatives.

2-Methyl-5-(3-trifluoromethoxy-phenyl)-oxazole-4-carboxylic acid prepared according to general procedure A.1.9.2 from 2-acetylamino-3-oxo-3-(3-trifluoromethoxy-phenyl)-propionic acid methyl ester acid methyl ester. LC-MS: $t_R$=0.95 min; [M−H]⁺=287.86.

A.1.10 Synthesis of 3-aryl-thiophene-2-carboxylic acid derivatives

A.1.10.1
3-(3-Methoxy-phenyl)-thiophene-2-carboxylic acid

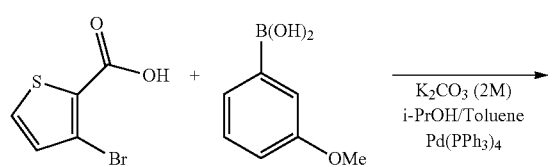

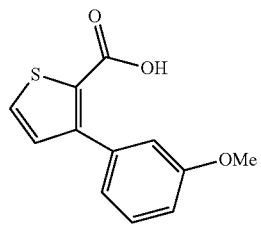

3-Bromothiophene-2-carboxylic acid (600 mg; 2.9 mmol) was dissolved in isopropanol (7 ml)/toluene (7 ml), followed by the addition of K₂CO₃ solution (aq; 2M; 9 ml) and 3-methoxybenzeneboronic acid (440 mg; 2.9 mmol). The reaction mixture was deoxygenized with N₂ (g) for 3 minutes followed by the addition of tetrakis-(triphenylphosine)-palladium and subsequently heated to 80° C. for 14 h. The mixture was cooled to rt, ether was added and the organic layer was extracted with 2M NaOH-solution. The aq. layer was acidified by the addition of 2M HCl. The product precipitated and was filtered off and dried at high vacuum to give 470 mg of 3-(3-methoxy-phenyl)-thiophene-2-carboxylic acid; LC-MS: $t_R$=0.94 min; [M−H]⁺=235.27.

A.1.10.2
3-(3,4-Dimethoxy-phenyl)-thiophene-2-carboxylic acid

According to the procedure described above 400 mg of 3-(3,4-dimethoxy-phenyl)-thiophene-2-carboxylic acid {LC-MS: $t_R$=0.88 min; [M−H]⁺=265.24.} was obtained from 3-Bromothiophene-2-carboxylic acid (600 mg; 2.9 mmol) and 3,4-dimethoxyboronic acid (527 mg; 2.9 mmol).

A.1.10.3
3-Benzo[1,3]dioxol-5-yl-thiophene-2-carboxylic acid

According to the procedure described above 430 mg of 3-Benzo[1,3]dioxol-5-yl-thiophene-2-carboxylic acid {LC-MS: $t_R$=0.93 min; [M−H]⁺=290.22.} was obtained from 3-Bromothiophene-2-carboxylic acid (600 mg; 2.9 mmol) and 3,4-(methylenedioxy)phenylboronic acid (480 mg; 2.9 mmol).

A.1.10.4
3-(4-Methoxy-phenyl)-thiophene-2-carboxylic acid

According to the procedure described above 424 mg of 3-(4-Methoxy-phenyl)-thiophene-2-carboxylic acid {LC-MS: $t_R$=0.94 min; [M−H]⁺=276.22.} was obtained from 3-Bromothiophene-2-carboxylic acid (600 mg; 2.9 mmol) and 4-methoxyphenylboronic acid (440 mg; 2.9 mmol).

A.1.11. Synthesis of 3-aryl-pyrazine-2-carboxylic acids

A.1.11.1 3-p-Tolyl-pyrazine-2-carboxylic acid

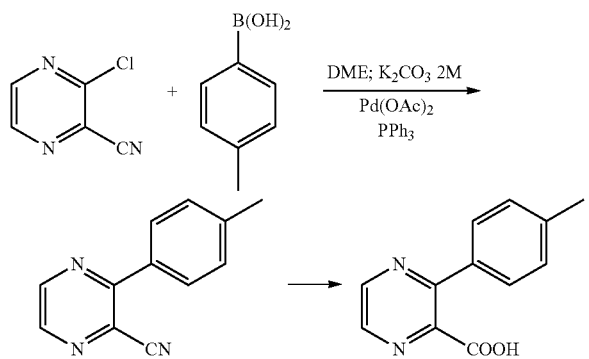

3-Chloropyrazine-2-carbonitrile (3.0 g; 21.5 mmol) was dissolved in dimethoxyethane (65 ml) and 4-tolylboronic acid (3.2 g; 23.65 mmol) was added, followed by the addition of $K_2CO_3$ (8.2 g; 59 mmol) and water (30 ml). The reaction mixture was deoxygenized with $N_2$ (g) for 3 minutes followed by the addition of triphenylphosphine (842 mg; 3.2 mmol) and palladium(II)acetate (237 mg; 1.06 mmol). The reaction mixture was heated to 90° C. for 14 h, cooled to rt, diluted with EtOAc, filtered over a plug of celite and dried with magnesiumsulfate. The organic solvent was evaporated under reduced pressure to give 5.3 g of 3-p-tolyl-pyrazine-2-carbonitrile. The intermediate nitrile was dissolved in MeOH (110 ml) followed by the addition of 4M aq NaOH (180 ml). The resulting mixture was heated to 85° C. for 14 h, cooled to rt and the MeOH was evaporated under reduced pressure. The residual aq. phase was acidified to pH=2 by the addition of conc. HCl and the precipitated product was filtered off, dissolved in DCM/EtOAc and dried over magnesium sulfate, filtered and concentrated under reduced pressure to give 2.30 g of 3-p-tolyl-pyrazine-2-carboxylic acid. LC-MS: $t_R$=0.40 min; [M–H]$^+$=213.14.

A.1.11.2 3-(3,4-Dimethyl-phenyl)-pyrazine-2-carboxylic acid

According to the procedure described above 3.8 g of 3-(3,4-Dimethyl-phenyl)-pyrazine-2-carboxylic acid was prepared. LC-MS: $t_R$=0.50 min; [M–H]$^+$=227.07.

A.1.11.3 3-(1H-Indol-6-yl)-pyrazine-2-carboxylic acid

According to the procedure described above 540 mg of 3-(1H-Indol-6-yl)-pyrazine-2-carboxylic acid was prepared. LC-MS: $t_R$=0.72 min; [M–H]$^+$=240.25.

A.2 Synthesis of benzo[1,4]oxazine-carboxylic acid derivatives

A.2.1 Synthesis of 2-amino-3-hydroxy-benzoic acid methyl ester

A solution of (trimethylsilyl)diazomethane in hexane (2.0 M, 10.9 mmol) is added dropwise (10 min) to a mixture of 3-hydroxyanthranilic acid (9.93 mmol) in MeOH (10.5 mL) and toluene (42 mL). The mixture is stirred for 16 h, concentrated in vacuo, diluted with ether and EtOAc and washed several times with water. The organic layer is dried over $MgSO_4$ and concentrated under reduced pressure. The residue is purified by flash chromatography (gradient: heptane to heptane/EtOAc 7/3) to give the desired ester as a brown solid. LC-MS: $t_R$=0.70 min; [M+H]$^+$=168.0.

A.2.2 Synthesis of 3-oxo-3,4-dihydro-2H-benzo[1,4]oxazine-5-carboxylic acid methyl ester At rt chloro-acetyl chloride (8.06 mmol) is added dropwise to a solution of 2-amino-3-hydroxy-benzoic acid methyl ester (7.33 mmol) in DMF (50 mL). After 20 min $K_2CO_3$ (34.9 mmol) is added portionwise, the mixture is stirred for 16 h at rt and the solvents are removed in vacuo. Water and DCM are added, the layers are separated and the organic layer is washed with brine and dried over $Na_2SO_4$. The solvents are removed in vacuo to give a crude product which is purified by flash chromatography (gradient: heptane to heptane/EtOAc 6/4). LC-MS: $t_R$=0.82 min; [M+$CH_3CN$+H]$^+$=249.0.

A.2.3 Synthesis of 3,4-dihydro-2H-benzo[1,4]oxazine-5-carboxylic acid methyl ester Boron trifluoride diethyl etherate (7.10 mmol) is added dropwise to a mixture of 3-oxo-3,4-dihydro-2H-benzo[1,4]oxazine-5-carboxylic acid methyl ester (3.38 mmol) in THF (10 mL) to keep the temperature below 5° C. After 20 min $NaBH_4$ (7.10 mmol) is added and the mixture is stirred at 5° C. for 90 min. EtOAc (6.0 mL) and hydrochloric acid (1.0 M, 6.0 mL) are added dropwise. The mixture is made basic by addition of aq. $Na_2CO_3$ solution, the layers are separated and the aq. layer is extracted with EtOAc. The combined organic layers are dried over $MgSO_4$ and concentrated in vacuo to give a crude product which is purified by flash chromatography (gradient: heptane to heptane/EtOAc 3/7). LC-MS: $t_R$=0.90 min; [M+$CH_3CN$+H]$^+$=235.3.

A.2.4 Synthesis of benzo[1,4]oxazine-carboxylic acid derivatives by ester hydrolysis (general procedure)

A solution of NaOH (4.00 mmol) in a mixture of MeOH (3.0 mL) and water (6.8 mL) is added to the respective ester derivative (2.00 mmol). The mixture is stirred at 55° C. for 16 h, partially concentrated in vacuo to remove MeOH and made acidic by addition of hydrochloric acid (1.0M). The respective carboxylic acid precipitates and is collected by filtration. 3,4-dihydro-2H-benzo[1,4]oxazine-5-carboxylic acid prepared by saponification of 3,4-dihydro-2H-benzo[1,4]oxazine-5-carboxylic acid methyl ester. LC-MS: $t_R$=0.76 min; [M+H]$^+$=180.2.

A.3 Synthesis of 2,3,6,7-Tetrahydro-benzo[1,2-b; 4,5-b']difuran-4-carboxylic acid 4-Formyl-2,3,6,7-tetrahydro-benzo[1,2-b; 4,5-b']difuran (0.25 mmol; Lit.: A. P. Monte, D. Marona-Lewicka, M. A. Parker, D. B. Wainscott, D. L. Nelson, D. E. Nichols *J. Med. Chem.*, 1996, 39, 2953-2961) is added to a stirred suspension of silver(I) oxide (0.375 mmol) in an aq. NaOH solution (5%, 0.20 mL). The mixture is stirred for 5 h, filtered and washed with water (2.0 mL). The filtrate is cooled to 0° C. and made acidic by dropwise addition of hydrochloric acid (25%). The obtained suspension is filtered off and washed with ice-cold water and heptane. The residue is dried in vacuo to give the desired acid as a grey powder which is used without further purification. LC-MS (basic): $t_R$=0.20 min; [M−H]⁻=205.2.

A.4 Synthesis of benzothiazole-7-carboxylic acid

A.4.1 Synthesis of 3-thioureido-benzoic acid methyl ester

At −10° C. sulfuric acid (0.46 mL) is added dropwise to a solution of methyl 3-aminobenzoate (17.2 mmol) in chlorobenzene (19 mL). After 15 min potassium thiocyanate (18.2 mmol) is added portionwise over 30 min. The mixture is treated with 18-crown-6 (0.18 mmol), heated to 100° C. for 16 h and allowed to cool to rt. After 4 h the obtained precipitate is filtered off and washed successively with chlorobenzene (33 mL) and hexane (three times 130 mL). The residue is diluted with water (390 mL) and the suspension is stirred for 30 min. After filtration the residue is washed twice with water (130 ml, each), concentrated in vacuo and dried additionally by azeotropic removal of water with toluene. The obtained product is used without further purification. LC-MS: $t_R$=0.66 min; [M+H]⁺=211.0.

A.4.2 Synthesis of 2-amino-benzothiazole-7-carboxylic acid methyl ester

At 0° C. a solution of bromine (13.4 mmol) in acetic acid (9.4 mL) is added dropwise to a vigorously stirred solution of 3-thioureido-benzoic acid methyl ester (12.5 ml) in acetic acid (37 mL). The mixture is allowed to reach rt, stirred at 70° C. for 4 h and cooled to rt. Ether is added and the precipitate is filtered off. The residue is stirred vigorously in a sat aq. NaHCO₃ solution, filtered off and washed with water. The obtained solid is dried in vacuo to give the desired product which is used without further purification. LC-MS: $t_R$=0.62 min; [M+H]⁺=209.0.

A.4.3 Synthesis of benzothiazole-7-carboxylic acid methyl ester

Isoamyl nitrite (22.0 mmol) is added to a solution of 2-amino-benzothiazole-7-carboxylic acid methyl ester (10.1 mmol) in THF (29 mL). The mixture is heated to reflux for 4 h, the solvents are removed in vacuo and the residue is purified by flash chromatography (gradient: heptane to EtOAc/heptane 4/6) to give the desired product. LC-MS: $t_R$=0.85 min; [M+H]⁺=194.0.

A.4.4 Synthesis of benzothiazole-7-carboxylic acid

At 0° C. an aq. NaOH solution (50%, 6.0 mL) is added to a solution of benzothiazole-7-carboxylic acid methyl ester in a mixture of MeOH (39 mL), THF (11.7 mL) and water (3.0 mL). The mixture is stirred for 4 h and concentrated in vacuo. At 0° C. water (60 mL) is added and the mixture is made acidic (pH 5) by addition of conc. hydrochloric acid. After 30 min the precipitate is filtered off, washed with water and dried in vacuo to give the desired product. LC-MS: $t_R$=0.77 min; [M+CH₃CN+H]⁺=221.1.

A.5 Synthesis of 6-methyl-pyrrolo[2,1-b]thiazole-7-carboxylic acid

A.5.1 Synthesis of 6-bromo-pyrrolo[2,1-b]thiazole-7-carboxylic acid ethyl ester N-Bromosuccinimide (0.56 mmol) is added to a solution of pyrrolo[2,1-b]thiazole-7-carboxylic acid ethyl ester (0.56 mmol) in DCM (6.0 mL). After 30 min water (5.0 mL) is added, the layers are separated and the aq. layer is extracted with DCM (5.0 mL). The combined organic layers are dried over Na₂SO₄ and the solvents are removed in vacuo to give the desired product which is used without further purification. LC-MS: $t_R$=1.02 min; [M+H]⁺=273.9.

A.5.2 Synthesis of 6-methyl-pyrrolo[2,1-b]thiazole-7-carboxylic acid ethyl ester Under nitrogen atmosphere a solution of dimethylzinc in toluene (1.2 M, 19.1 mL) is added to a mixture of 6-bromo-pyrrolo[2,1-b]thiazole-7-carboxylic acid ethyl ester (11.4 mmol) and [1,1′-Bis(diphenylphosphino)ferrocene]dichloropalladium(II) (0.23 mmol, complex with CH₂Cl₂) in dioxane (35 mL). The mixture is heated to reflux for 2 h, stirred at rt for 12 h and diluted by addition of MeOH (2.3 mL) and TBME. The mixture is washed with hydrochloric acid (1.0 M) and water, dried over MgSO₄, concentrated in vacuo and purified by flash chromatography (gradient: heptane to heptane/EtOAc 8/2) to give the desired product. LC-MS: $t_R$=0.91 min; [M+H]⁺=210.0.

A.5.3 Synthesis of 6-methyl-pyrrolo[2,1-b]thiazole-7-carboxylic acid

A mixture of 6-methyl-pyrrolo[2,1-b]thiazole-7-carboxylic acid ethyl ester (7.29 mmol) and NaOH (10.9 mmol) in EtOH (11.8 mL) and water (11.8 mL) is heated to 75° C. for 3 d. The mixture is concentrated in vacuo and made acidic by addition of hydrochloric acid (1.0 M). The obtained precipitate is filtered off and dried in vacuo to give the desired product. LC-MS: $t_R$=0.73 min; [M+H]⁺=182.0.

A.6 Synthesis of 2-Methyl-benzooxazole-4-carboxylic acid

A.6.1 Synthesis of 2-Methyl-benzooxazole-4-carboxylic acid ethyl ester

A mixture of 2-amino-3-hydroxy-benzoic acid ethyl ester (5.52 mmol; J. Reisch, G. M. K. B. Gunaherath *Monatshefte für Chemie,* 1988, 119, 1169-1178), acetyl chloride (6.07 mmol), NEt₃ (6.07 mmo) and pyridinium p-toluenesulfonate (1.47 mmol) in xylene (60 mL) is heated at reflux for 16 h, cooled to rt, diluted with EtOAc and washed with water. The organic layer is dried over MgSO₄ and concentrated in vacuo to give a crude product which is purified by flash chromatography (gradient: heptane to heptane/EtOAc 6/4). LC-MS: $t_R$=0.81 min; [M+H]⁺=206.0.

A.6.2 Synthesis of 2-Methyl-benzooxazole-4-carboxylic acid

At 0° C. an aq. KOH solution (1.0M, 2.40 mL) is added to a solution of 2-methyl-benzooxazole-4-carboxylic acid ethyl ester (0.98 mmol) in MeOH (5.0 mL) and stirred for 30 min. The mixture is allowed to reach rt, stirred for additional 60 min and made acidic by addition of aq. hydrochloric acid (2.0 M). After removal of MeOH under reduced pressure the obtained precipitate is filtered off to give the desired product which is dried in vacuo. ¹H-NMR (DMSO-d₆): δ=2.64 (s, 3H); 7.41 (t, J=8.0 Hz, 1H); 7.83 (d, J=7.8 Hz, 1H); 7.88 (d, J=8.0 Hz, 1H); 12.8 (bs, 1H).

B PREPARATION OF SCAFFOLDS

B.1 Synthesis of (1R,3S,4S)-3-Aminomethyl-2-aza-bicyclo[2.2.1]heptane-2-carboxylic acid tert-butyl ester

B.1.1 Synthesis of (1R,3S,4S)-2-Aza-bicyclo[2.2.1]heptane-2,3-dicarboxylic acid 2-tert-butyl ester 3-methyl ester A solution of (1S,3S,4R)-2-((R)-1-Phenyl-ethyl)-2-aza-bicyclo[2.2.1]hept-5-ene-3-carboxylic acid methyl ester (61.0 mmol; N. Hashimoto, H. Yasuda, M. Hayashi, Y. Tanabe *Org. Proc. Res. Dev.* 2005, 9, 105-109) in EtOH (100 mL) is treated with di-tert-butyl dicarbonate (62.2 mmol, 1.02 eq) and Pd/C (10%, 2.0 g). The mixture is stirred under a hydrogen atmosphere (7 bar) for 3 d. After filtration through celite and removal of the solvents in vacuo the desired product is obtained which is used without further purification.
$^1$H-NMR (CDCl$_3$, 2 rotamers): δ=1.25-1.31 (m, 1H); 1.41 & 1.48 (2 s, 9H); 1.48-1.81 (m, 4H); 1.92-1.97 (m, 1H); 2.68 (bs, 1H); 3.74 (s, 3H); 3.75 & 3.86 (2 bs, 1H); 4.24 & 4.38 (2 bs, 1H).

B.1.2 Synthesis of (1R,3S,4S)-3-Hydroxymethyl-2-aza-bicyclo[2.2.1]heptane-2-carboxylic acid tert-butyl ester At −78° C. a solution of DIBAL in toluene (1.7M, 137 mmol) is added dropwise to a solution of (1R,3S,4S)-2-aza-bicyclo[2.2.1]heptane-2,3-dicarboxylic acid 2-tert-butyl ester 3-methyl ester (61.0 mmol) in THF (180 mL). After 80 min the solution is allowed to reach rt, stirred for additional 2 h and poured into a mixture of aq. NaOH solution (1.0M, 200 mL) and ice. EtOAc (150 mL) is added, the layers are separated and the aq. layer is extracted three times with EtOAc (150 mL each). The combined organic layers are washed with aq. NaOH solution (1.0M) and brine, dried over Na$_2$SO$_4$ and concentrated in vacuo to give a crude product which is used without further purification. LC-MS (basic): $t_R$=0.78 min; [M+H]$^+$=228.3.

B.1.3 Synthesis of (1R,3S,4S)-3-Formyl-2-aza-bicyclo[2.2.1]heptane-2-carboxylic acid tert-butyl ester To a cold (−60° C.) solution of oxalyl chloride (60.8 mmol) in dry DCM (130 mL) is added dropwise DMSO (111 mmol) within 5 min. After 15 min a solution of (1R,3S,4S)-3-hydroxymethyl-2-aza-bicyclo[2.2.1]heptane-2-carboxylic acid tert-butyl ester (50.7 mmol) in dry DCM (40 mL) is added dropwise within 15 min. Stirring is continued for 45 min at −55° C., then DIPEA (253 mmol; dried over 3 A molecular sieve) is added during 5 min. The reaction mixture is allowed to reach rt and diluted with water (250 mL). The layers are separated and the organic layer is washed twice with aq. citric acid (5%, 200 mL each) and twice with brine. The combined organic layers are dried over MgSO$_4$ and concentrated in vacuo to give the desired product which is used without further purification. $^1$H-NMR (CDCl$_3$, 2 rotamers): δ=1.31-1.37 (m, 1H); 1.44 & 1.50 (2 s, 9H); 1.58-1.84 (m, 5H); 2.78 & 2.81 (2 bs, 1H); 3.60 & 3.74 (2 bs, 1H); 4.26 & 4.41 (2 bs, 1H); 9.55 & 9.60 (2 bs, 1H).

B.1.4 Synthesis of (1R,3S,4S)-3-(Benzylamino-methyl)-2-aza-bicyclo[2.2.1]heptane-2-carboxylic acid tert-butyl ester Benzylamine (49.7 mmol) is added to a solution of (1R,3S,4S)-3-formyl-2-aza-bicyclo[2.2.1]heptane-2-carboxylic acid tert-butyl ester (49.7 mmol) in DCM (200 mL). The mixture is treated with sodium triacetoxyborohydride (69.6 mmol), stirred for additional 20 min, poured into water (200 mL) and stirred vigorously for 10 min. The layers are separated and the aq. layer is extracted twice with DCM (2×100 mL). The combined organic layers are washed with sat. NaHCO$_3$ solution (100 mL), water (100 mL) and brine (150 mL), dried over MgSO$_4$ and treated with activated charcoal (5 g). The mixture is filtered through celite and the filtrate is concentrated in vacuo to give the desired benzylamine which is used without further purification. LC-MS (basic): $t_R$=1.00 min; [M+H]$^+$=317.3.

B.1.5 Synthesis of (1R,3S,4S)-3-Aminomethyl-2-aza-bicyclo[2.2.1]heptane-2-carboxylic acid tert-butyl ester A solution of (1R,3S,4S)-3-(benzylamino-methyl)-2-aza-bicyclo[2.2.1]heptane-2-carboxylic acid tert-butyl ester (39.8 mmol) in EtOH (120 mL) is treated with Pd/C (10%, 4.0 g) and stirred under a hydrogen atmosphere (7 bar) for 1 d. An additional amount of Pd/C (1.0 g) is added and the mixture is stirred for further 6 h under a hydrogen atmosphere (7 bar). After filtration through celite and removal of the solvents in vacuo the desired amine is obtained which is used without further purification. LC-MS (basic): $t_R$=0.85 min; [M+H]$^+$=227.3.

B.2 Synthesis of (1R,3S,4S)-3-Acylaminomethyl-2-aza-bicyclo[2.2.1]heptane derivatives

B.2.1 Synthesis of (1R,3S,4S)-3-Acylaminomethyl-2-aza-bicyclo[2.2.1]heptane-2-carboxylic acid tert-butyl ester derivatives (general procedure)

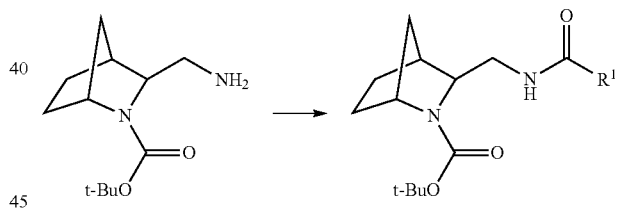

TBTU (0.73 mmol, 1.10 eq) is added to a solution of the respective carboxylic acid (0.70 mmol, 1.05 eq) and DIPEA (1.66 mmol, 2.5 eq) in DCM (1.0 mL) and DMF (0.25 mL). After 10 min a solution of (1R,3S,4S)-3-aminomethyl-2-aza-bicyclo[2.2.1]heptane-2-carboxylic acid tert-butyl ester (0.66 mmol, 1.0 eq) in DCM (1.0 mL) is added and the mixture is stirred for 2 h and washed twice with water (1.0 mL). The organic layer is dried over MgSO$_4$, the solvents are removed in vacuo and the residue is purified by prep. HPLC to give the respective amide.

(1R,3S,4S)-3-{[(Benzofuran-4-carbonyl)-amino]-methyl}-2-aza-bicyclo[2.2.1]heptane-2-carboxylic acid tert-butyl ester prepared by reaction of (1R,3S,4S)-3-aminomethyl-2-aza-bicyclo[2.2.1]heptane-2-carboxylic acid tert-butyl ester with benzofuran-4-carboxylic acid (M. A. Eissenstat et al. *J. Med. Chem.* 1995, 38, 3094-3105). LC-MS (basic): $t_R$=0.97 min; [M+H]$^+$=371.1.

(1R,3S,4S)-3-{[(Quinoline-8-carbonyl)-amino]-methyl}-2-aza-bicyclo[2.2.1]heptane-2-carboxylic acid tert-butyl ester prepared by reaction of (1R,3S,4S)-3-aminomethyl-2-aza-bicyclo[2.2.1]heptane-2-carboxylic acid tert-butyl ester with quinoline-8-carboxylic acid. LC-MS (basic): $t_R$=0.95 min; $[M+H]^+$=382.2.

(1R,3S,4S)-3-{[(2,3-Dihydro-benzo[1,4]dioxine-5-carbonyl)-amino]-methyl}-2-aza-bicyclo[2.2.1]heptane-2-carboxylic acid tert-butyl ester prepared by reaction of (1R,3S,4S)-3-aminomethyl-2-aza-bicyclo[2.2.1]heptane-2-carboxylic acid tert-butyl ester with 2,3-dihydro-benzo[1,4]dioxine-5-carboxylic acid. LC-MS (basic): $t_R$=0.91 min; $[M+H]^+$=389.1.

(1R,3S,4S)-3-{[(6-Methyl-imidazo[2,1-b]thiazole-5-carbonyl)-amino]-methyl}-2-aza-bicyclo[2.2.1]heptane-2-carboxylic acid tert-butyl ester prepared by reaction of (1R,3S,4S)-3-aminomethyl-2-aza-bicyclo[2.2.1]heptane-2-carboxylic acid tert-butyl ester with 6-methyl-imidazo[2,1-b]thiazole-5-carboxylic acid. LC-MS (basic): $t_R$=0.88 min; $[M+H]^+$=391.1.

(1R,3S,4S)-3-{[(2-Ethyl-5-methyl-2H-pyrazole-3-carbonyl)-amino]-methyl}-2-aza-bicyclo[2.2.1]heptane-2-carboxylic acid tert-butyl ester prepared by reaction of (1R,3S,4S)-3-aminomethyl-2-aza-bicyclo[2.2.1]heptane-2-carboxylic acid tert-butyl ester with 2-ethyl-5-methyl-2H-pyrazole-3-carboxylic acid. LC-MS (basic): $t_R$=0.92 min; $[M+H]^+$=363.0.

B.2.2 Synthesis of (1R,3S,4S)-3-Acylaminomethyl-2-aza-bicyclo[2.2.1]heptane derivatives (general procedure)

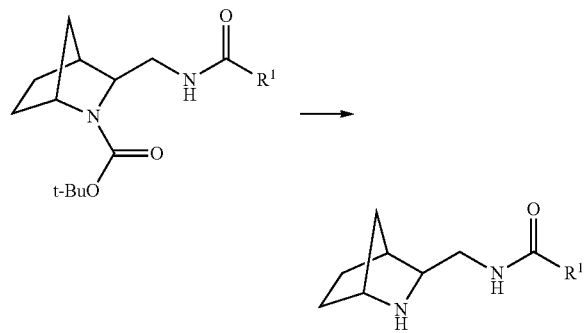

A solution of HCl in dioxane (4.0 M, 2.0 mL) is added to a solution of the respective Boc-protected 2-aza-bicyclo[2.2.1]heptane derivative (0.40 mmol) in dioxane (1.0 mL). After LC-MS indicated complete conversion (2 h) the mixture is concentrated in vacuo. The residue is repeatedly dissolved in a mixture of MeOH and EtOAc and concentrated in vacuo to give the respective deprotected product as a hydrochloride salt which is used without further purification.

Benzofuran-4-carboxylic acid [(1R,3S,4S)-1-(2-aza-bicyclo[2.2.1]hept-3-yl)methyl]-amide prepared by deprotection of (1R,3S,4S)-3-{[(Benzofuran-4-carbonyl)-amino]-methyl}-2-aza-bicyclo[2.2.1]heptane-2-carboxylic acid tert-butyl ester. LC-MS (basic): $t_R$=0.83 min; $[M+H]^+$=271.2.

Quinoline-8-carboxylic acid [(1R,3S,4S)-1-(2-aza-bicyclo[2.2.1]hept-3-yl)methyl]-amide prepared by deprotection of (1R,3S,4S)-3-{[(Quinoline-8-carbonyl)-amino]-methyl}-2-aza-bicyclo[2.2.1]heptane-2-carboxylic acid tert-butyl ester. LC-MS (basic): $t_R$=0.93 min; $[M+H]^+$=282.2.

2,3-Dihydro-benzo[1,4]dioxine-5-carboxylic acid [(1R,3S,4S)-1-(2-aza-bicyclo[2.2.1]hept-3-yl)methyl]-amide prepared by deprotection of (1R,3S,4S)-3-{[(2,3-Dihydro-benzo[1,4]dioxine-5-carbonyl)-amino]-methyl}-2-aza-bicyclo[2.2.1]heptane-2-carboxylic acid tert-butyl ester. LC-MS (basic): $t_R$=0.81 min; $[M+H]^+$=289.2.

6-Methyl-imidazo[2,1-b]thiazole-5-carboxylic acid [(1R,3S,4S)-1-(2-aza-bicyclo[2.2.1]hept-3-yl)methyl]-amide prepared by deprotection of (1R,3S,4S)-3-{[(6-Methyl-imidazo[2,1-b]thiazole-5-carbonyl)-amino]-methyl}-2-aza-bicyclo[2.2.1]heptane-2-carboxylic acid tert-butyl ester. LC-MS (basic): $t_R$=0.69 min; $[M+H]^+$=291.1.

2-Ethyl-5-methyl-2H-pyrazole-3-carboxylic acid [(1R,3S,4S)-1-(2-aza-bicyclo[2.2.1]hept-3-yl)methyl]-amide prepared by deprotection of (1R,3S,4S)-3-{[(2-Ethyl-5-methyl-2H-pyrazole-3-carbonyl)-amino]-methyl}-2-aza-bicyclo[2.2.1]heptane-2-carboxylic acid tert-butyl ester. LC-MS (basic): $t_R$=0.69 min; $[M+H]^+$=263.3.

B.3 Synthesis of 2-substituted (1R,3S,4S)-3-Aminomethyl-2-aza-bicyclo[2.2.1]heptane derivatives B.3.1 Synthesis of (1R,3S,4S)-3-[(2,2,2-Trifluoroacetylamino)-methyl]-2-aza-bicyclo[2.2.1]heptane-2-carboxylic acid tert-butyl ester Ethyl trifluoroacetate (12.2 mmol, 1.30 eq) is added to a solution of (1R,3S,4S)-3-aminomethyl-2-aza-bicyclo[2.2.1]heptane-2-carboxylic acid tert-butyl ester (9.42 mmol, 1.00 eq) and DIPEA (14.1 mmol, 1.50 eq) in THF (25 mL). After 50 min the mixture is concentrated in vacuo, diluted with TBME (100 mL) and washed twice with aq. citric acid (5%) and water respectively. The organic layer is dried over $MgSO_4$ and concentrated in vacuo to give a crude product which is used without further purification. LC-MS (basic): $t_R$=0.95 min; $[M+H]^+$=323.2.

B.3.2 Synthesis of N-[(1R,3S,4S)-1-(2-Aza-bicyclo[2.2.1]hept-3-yl)methyl]-2,2,2-trifluoro-acetamide (hydrochloride salt)

A solution of HCl in dioxane (4 M, 40 mL) is added to a solution of (1R,3S,4S)-3-[(2,2,2-trifluoro-acetylamino)-methyl]-2-aza-bicyclo[2.2.1]heptane-2-carboxylic acid tert-butyl ester (12.0 mmol) in dioxane (15 mL). After 3 h the solvents are removed in vacuo to give the desired product as a brownish solid which is used without further purification in the next step. LC-MS (basic): $t_R$=0.69 min; $[M+H]^+$=223.2.

B.3.3 Synthesis of 2,2,2-Trifluoro-N-[(1R,3S,4S)-2-(5-phenyl-thiazole-4-carbonyl)-2-aza-bicyclo[2.2.1]hept-3-ylmethyl]-acetamide derivatives (general procedure)

TBTU (1.70 mmol, 1.1 eq) is added to a solution of the respective 5-phenyl-thiazole-4-carboxylic acid derivative (1.62 mmol, 1.05 eq) and DIPEA (2.33 mmol, 1.5 eq) in DMF (5.0 mL). The mixture is stirred for 10 min and treated with a solution of N-[(1R,3S,4S)-1-(2-Aza-bicyclo[2.2.1]hept-3-yl)methyl]-2,2,2-trifluoro-acetamide (1.55 mmol, 1.0 eq) and DIPEA (3.87 mmol, 2.5 eq) in DMF (5.0 mL). After 90 min the mixture is diluted with TBME (50 mL) and washed three times with an aq. NaOH solution (0.5 M, 50 mL each). The combined aq. layers are extracted twice with TBME (30 mL each). The organic layers are combined, washed with water (3×30 mL) and brine (30 mL), dried over MgSO₄ and concentrated in vacuo to give a crude product which is used without further purification.

2,2,2-Trifluoro-N-[(1R,3S,4S)-2-(2-methyl-5-m-tolyl-thiazole-4-carbonyl)-2-aza-bicyclo[2.2.1]hept-3-ylmethyl]-acetamide prepared by reaction of N-[(1R,3S,4S)-1-(2-Aza-bicyclo[2.2.1]hept-3-yl)methyl]-2,2,2-trifluoro-acetamide with 2-methyl-5-m-tolyl-thiazole-4-carboxylic acid. LC-MS (basic): $t_R$=0.94 min; [M+H]⁺=438.0.

N-{(1R,3S,4S)-2-[5-(3-Chloro-phenyl)-2-methyl-thiazole-4-carbonyl]-2-aza-bicyclo[2.2.1]hept-3-ylmethyl}-2,2,2-trifluoro-acetamide prepared by reaction of N-[(1R,3S,4S)-1-(2-Aza-bicyclo[2.2.1]hept-3-yl)methyl]-2,2,2-trifluoro-acetamide with 5-(3-Chloro-phenyl)-2-methyl-thiazole-4-carboxylic acid. LC-MS (basic): $t_R$=0.95 min; [M+H]⁺=457.7.

B.3.4 Synthesis of N-{(1R,3S,4S)-2-[2-Amino-5-(3-fluoro-phenyl)-thiazole-4-carbonyl]-2-aza-bicyclo[2.2.1]hept-3-ylmethyl}-2,2,2-trifluoro-acetamide TBTU (1.70 mmol, 1.10 eq) is added to a solution of 2-amino-5-(3-fluoro-phenyl)-thiazole-4-carboxylic acid (1.62 mmol, 1.05 eq), N-[(1R,3S,4S)-1-(2-Aza-bicyclo[2.2.1]hept-3-yl)methyl]-2,2,2-trifluoro-acetamide (1.55 mmol, 1.0 eq) and DIPEA (5.41 mmol, 3.5 eq) in DMF (10 mL). After 90 min the mixture is diluted with TBME (50 mL) and washed three times with an aq. NaOH solution (0.5 M, 50 mL each). The combined aq. layers are extracted twice with TBME (30 mL each). The organic layers are combined, washed with water (3×30 mL) and brine (30 mL), dried over MgSO₄ and concentrated in vacuo to give a crude product which is used without further purification. LC-MS (basic): $t_R$=0.82 min; [M+H]⁺=442.9.

B.3.5 Synthesis of N-{(1R,3S,4S)-2-[2-Dimethylamino-5-phenyl-thiazole-4-carbonyl]-2-aza-bicyclo[2.2.1]hept-3-ylmethyl}-2,2,2-trifluoro-acetamide derivatives (general procedure)

TBTU (2.13 mmol) and DIPEA (4.83 mmol) are added to a solution of the respective 5-phenyl-thiazole-4-carboxylic acid derivative (2.32 mmol) in MeCN (5.0 mL). The mixture is stirred for 15 min and treated with a solution of N-[(1R,3S,4S)-1-(2-Aza-bicyclo[2.2.1]hept-3-yl)methyl]-2,2,2-trifluoro-acetamide (1.93 mmol) and DIPEA (4.83 mmol) in MeCN (5.0 mL). After 14 h the mixture is diluted with EtOAc and washed three times with brine. The combined aq. layers are extracted with EtOAc. The organic layers are combined, dried over MgSO₄ and concentrated in vacuo to give the respective crude product which is used without further purification.

N-{(1R,3S,4S)-2-[2-Dimethylamino-5-phenyl-thiazole-4-carbonyl]-2-aza-bicyclo[2.2.1]hept-3-ylmethyl}-2,2,2-trifluoro-acetamide prepared by reaction of N-[(1R,3S,4S)-1-(2-Aza-bicyclo[2.2.1]hept-3-yl)methyl]-2,2,2-trifluoro-acetamide with 2-dimethylamino-5-phenyl-thiazole-4-carboxylic acid. LC-MS: $t_R$=1.10 min; [M+H]⁺=453.1.

N-{(1R,3S,4S)-2-[2-Dimethylamino-5-(3-fluoro-phenyl)-thiazole-4-carbonyl]-2-aza-bicyclo[2.2.1]hept-3-ylmethyl}-2,2,2-trifluoro-acetamide prepared by reaction of N-[(1R,3S,4S)-1-(2-Aza-bicyclo[2.2.1]hept-3-yl)methyl]-2,2,2-trifluoro-acetamide with 2-dimethylamino-5-(3-fluoro-phenyl)-thiazole-4-carboxylic acid. LC-MS: $t_R$=1.12 min; [M+H]⁺=471.1.

B.3.6 Synthesis of ((1R,3S,4S)-3-Aminomethyl-2-aza-bicyclo[2.2.1]hept-2-yl)-[5-phenyl-thiazol-4-yl]methanone derivatives (general procedure)

A solution of the respective 2,2,2-trifluoro-N-[(1R,3S,4S)-2-(5-phenyl-thiazole-4-carbonyl)-2-aza-bicyclo[2.2.1]hept-3-ylmethyl]-acetamide derivative (1.49 mmol) in MeOH (5.0 mL) is treated with a sat. aq. K₂CO₃ solution (0.4 mL) and stirred at 60° C. for 6 h. After stirring at rt for additional 14 h the mixture is concentrated in vacuo and the residue is made acidic by addition of aq. citric acid (5%). The aq. layer is washed three times with TBME, made basic by addition of aq. NaOH solution and extracted four times with DCM. The combined DCM-layers are dried over Na₂SO₄ and concentrated in vacuo to give the desired product which is used without further purification.

((1R,3S,4S)-3-Aminomethyl-2-aza-bicyclo[2.2.1]hept-2-yl)-(2-methyl-5-m-tolyl-thiazol-4-yl)-methanone prepared by deprotection of 2,2,2-Trifluoro-N-[(1R,3S,4S)-2-(2-methyl-5-m-tolyl-thiazole-4-carbonyl)-2-aza-bicyclo[2.2.1]hept-3-ylmethyl]-acetamide. LC-MS (basic): $t_R$=0.77 min; [M+H]⁺=342.1.

((1R,3S,4S)-3-Aminomethyl-2-aza-bicyclo[2.2.1]hept-2-yl)-[5-(3-chloro-phenyl)-2-methyl-thiazol-4-yl]-methanone prepared by deprotection of N-{(1R,3S,4S)-2-[5-(3-Chloro-phenyl)-2-methyl-thiazole-4-carbonyl]-2-aza-bicyclo[2.2.1]hept-3-ylmethyl}-2,2,2-trifluoro-acetamide. LC-MS (basic): $t_R$=0.79 min; [M+H]⁺=361.7.

B.3.7 Synthesis of [2-Amino-5-(3-fluoro-phenyl)-thiazol-4-yl]-((1R,3S,4S)-3-aminomethyl-2-aza-bicyclo[2.2.1]hept-2-yl)-methanone A solution of N-{(1R,3S,4S)-2-[2-Amino-5-(3-fluoro-phenyl)-thiazole-4-carbonyl]-2-aza-bicyclo[2.2.1]hept-3-ylmethyl}-2,2,2-trifluoro-acetamide (0.98 mmol) in MeOH (3.2 mL) is treated with a sat. aq. K₂CO₃ solution (0.3 mL) and stirred at 60° C. for 6 h. After stirring at rt for additional 14 h the mixture is concentrated in vacuo and the residue is made basic by addition of aq. NaOH solution. A 1:1 mixture of TBME and EtOAc is added and the mixture is stirred vigorously for 1 h. The layers are separated and the aq. layer is extracted with a 1:1 mixture of TBME and EtOAc. The combined organic layers are dried over Na₂SO₄ and concentrated in vacuo to give the desired product which is used without further purification. LC-MS (basic): $t_R$=0.68 min; [M+H]⁺=347.1.

B.3.8 Synthesis of ((1R,3S,4S)-3-Aminomethyl-2-aza-bicyclo[2.2.1]hept-2-yl)-[2-dimethylamino-5-phenyl-thiazol-4-yl]-methanone derivatives (general procedure)

A solution of the respective 2,2,2-trifluoro-N-[(1R,3S,4S)-2-(2-dimethylamino-5-phenyl-thiazole-4-carbonyl)-2-azabicyclo[2.2.1]hept-3-ylmethyl]-acetamide derivative (2.49 mmol) in isopropanol (30 mL) is treated with an aq. NaOH solution (1.0 M, 8.0 mL) and stirred for 3 h. Water and EtOAc are added, the layers are separated and the aq. layer is extracted with EtOAc. The combined organic layers are washed with water, dried over MgSO$_4$ and concentrated in vacuo to give the desired product which is used without further purification.

((1R,3S,4S)-3-Aminomethyl-2-aza-bicyclo[2.2.1]hept-2-yl)-(2-dimethylamino-5-phenyl-thiazol-4-yl)-methanone prepared by deprotection of N-{(1R,3S,4S)-2-[2-Dimethylamino-5-phenyl-thiazole-4-carbonyl]-2-aza-bicyclo[2.2.1]hept-3-ylmethyl}-2,2,2-trifluoro-acetamide. LC-MS: $t_R$=0.80 min; [M+H]$^+$=357.1.

((1R,3S,4S)-3-Aminomethyl-2-aza-bicyclo[2.2.1]hept-2-yl)-[2-dimethylamino-5-(3-fluoro-phenyl)-thiazol-4-yl]-methanone prepared by deprotection of N-{(1R,3S,4S)-2-[2-Dimethylamino-5-(3-fluoro-phenyl)-thiazole-4-carbonyl]-2-aza-bicyclo[2.2.1]hept-3-ylmethyl}-2,2,2-trifluoro-acetamide. LC-MS: $t_R$=0.81 min; [M+H]$^+$=375.1.

B.4 Synthesis of [(1R,3S,4S)-1-(2-Aza-bicyclo[2.2.1]hept-3-yl)methyl]-(5-bromo-pyrimidin-2-yl)-amine

B.4.1 Synthesis of (1R,3S,4S)-3-[(5-Bromo-pyrimidin-2-ylamino)-methyl]-2-aza-bicyclo[2.2.1]heptane-2-carboxylic acid tert-butyl ester 5-Bromo-2-chloro-pyrimidine (8.62 mmol) is added to a solution of (1R,3S,4S)-3-aminomethyl-2-aza-bicyclo[2.2.1]heptane-2-carboxylic acid tert-butyl ester (6.63 mmol) in o-xylene (25 mL). K$_2$CO$_3$ (20.0 mmol) and DIPEA (19.9 mmol) are added successively and the mixture is heated to 138° C. for 16 h. The mixture is cooled to rt and filtered. The residue is washed with DCM and the combined filtrates are concentrated in vacuo to give the desired product which is used without further purification. LC-MS: $t_R$=1.09 min; [M+H]$^+$=383.3.

B.4.2 Synthesis of [(1R,3S,4S)-1-(2-Aza-bicyclo[2.2.1]hept-3-yl)methyl]-(5-bromo-pyrimidin-2-yl)-amine A solution of HCl in dioxane (4.0 M, 30 mL) is added to a solution of (1R,3S,4S)-3-[(5-bromo-pyrimidin-2-ylamino)-ethyl]-2-aza-bicyclo[2.2.1]heptane-2-carboxylic acid tert-butyl ester (6.63 mmol) in dioxane (30 mL). After 4 h the solvents are removed in vacuo to give a crude product which is used without further purification. LC-MS: $t_R$=0.64 min; [M+H]$^+$=283.0.

C. PREPARATION OF COMPOUNDS OF FORMULA (I)

C.1 Synthesis of carboxylic amide derivatives (general procedure)

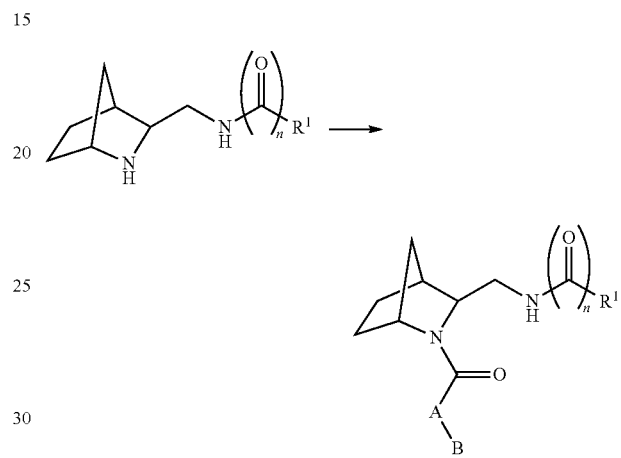

To a solution of the respective carboxylic acid (0.030 mmol, 1.2 eq) in DMF (0.50 mL) is added successively DIPEA (0.025 mmol, 1.0 eq) and a solution of TBTU (0.030 mmol, 1.2 eq) in DMF (0.50 mL). The obtained mixture is treated with a solution of the respective 2-aza-bicyclo[2.2.1]heptane derivative (0.025 mmol, 1.0 eq, hydrochloride salt) and DIPEA (0.050 mmol, 2.0 eq) in DMF (0.50 mL). The mixture is shaken over night and purified by prep. HPLC to give the respective amide derivative.

Starting from Quinoline-8-carboxylic acid [(1R,3S,4S)-1-(2-aza-bicyclo[2.2.1]hept-3-yl)methyl]-amide:

| | | | LC-MS | |
|---|---|---|---|---|
| Example | Name | eluent | $t_R$ [min] | [M + H]$^+$ |
| 1 | Quinoline-8-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.96 | 517.0 |
| 2 | Quinoline-8-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.80 0.83 | 502.1 |
| 3 | Quinoline-8-carboxylic acid [(1R,3S,4S)-2-(2-methyl-5-m-tolyl-thiazole-4-carbonyl)-2-aza-bicyclo[2.2.1]hept-3-ylmethyl]-amide | basic | 0.89 0.95 | 497.1 |

Starting from 2,3-Dihydro-benzo[1,4]dioxine-5-carboxylic acid [(1R,3S,4S)-1-(2-aza-bicyclo[2.2.1]hept-3-yl)methyl]-amide:

| | | | LC-MS | |
|---|---|---|---|---|
| Example | Name | eluent | t$_R$ [min] | [M + H]$^+$ |
| 4 | 2,3-Dihydro-benzo[1,4]dioxine-5-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.87 0.93 | 523.9 |
| 5 | 2,3-Dihydro-benzo[1,4]dioxine-5-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.77 0.80 | 509.0 |
| 6 | 2,3-Dihydro-benzo[1,4]dioxine-5-carboxylic acid [(1R,3S,4S)-2-(2-methyl-5-m-tolyl-thiazole-4-carbonyl)-2-aza-bicyclo[2.2.1]hept-3-ylmethyl]-amide | basic | 0.85 0.92 | 504.1 |

Starting from Benzofuran-4-carboxylic acid [(1R,3S,4S)-1-(2-aza-bicyclo[2.2.1]hept-3-yl)methyl]-amide:

| | | | LC-MS | |
|---|---|---|---|---|
| Example | Name | eluent | t$_R$ [min] | [M + H]$^+$ |
| 7 | Benzofuran-4-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.96 | 506.0 |
| 8 | Benzofuran-4-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.79 0.83 | 490.7 |
| 9 | Benzofuran-4-carboxylic acid [(1R,3S,4S)-2-(2-methyl-5-m-tolyl-thiazole-4-carbonyl)-2-aza-bicyclo[2.2.1]hept-3-ylmethyl]-amide | basic | 0.95 | 486.1 |
| 10 | Benzofuran-4-carboxylic acid [(1R,3S,4S)-2-(3'-chloro-biphenyl-2-carbonyl)-2-aza-bicyclo[2.2.1]hept-3-ylmethyl]-amide | basic | 0.98 | 485.0 |
| 11 | Benzofuran-4-carboxylic acid [(1R,3S,4S)-2-(2-methyl-4-phenyl-pyrimidine-5-carbonyl)-2-aza-bicyclo[2.2.1]hept-3-ylmethyl]-amide | basic | 0.79 0.83 | 467.1 |

Starting from 6-Methyl-imidazo[2,1-b]thiazole-5-carboxylic acid [(1R,3S,4S)-1-(2-aza-bicyclo[2.2.1]hept-3-yl)methyl]-amide:

| | | | LC-MS | |
|---|---|---|---|---|
| Example | Name | eluent | t$_R$ [min] | [M + H]$^+$ |
| 12 | 6-Methyl-imidazo[2,1-b]thiazole-5-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.88 | 525.9 |
| 13 | 6-Methyl-imidazo[2,1-b]thiazole-5-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.71 0.75 | 511.0 |
| 14 | 6-Methyl-imidazo[2,1-b]thiazole-5-carboxylic acid [(1R,3S,4S)-2-(2-methyl-5-m-tolyl-thiazole-4-carbonyl)-2-aza-bicyclo[2.2.1]hept-3-ylmethyl]-amide | basic | 0.86 | 506.0 |
| 15 | 6-Methyl-imidazo[2,1-b]thiazole-5-carboxylic acid [(1R,3S,4S)-2-(biphenyl-2-carbonyl)-2-aza-bicyclo[2.2.1]hept-3-ylmethyl]-amide | basic | 0.87 | 471.1 |
| 16 | 6-Methyl-imidazo[2,1-b]thiazole-5-carboxylic acid [(1R,3S,4S)-2-(3'-chloro-biphenyl-2- | basic | 0.90 | 504.9 |

-continued

| Example | Name | eluent | t_R [min] | [M + H]+ |
|---|---|---|---|---|
| | carbonyl)-2-aza-bicyclo[2.2.1]hept-3-ylmethyl]-amide | | | |
| 17 | 6-Methyl-imidazo[2,1-b]thiazole-5-carboxylic acid [(1R,3S,4S)-2-(2-methyl-4-phenyl-pyrimidine-5-carbonyl)-2-aza-bicyclo[2.2.1]hept-3-ylmethyl]-amide | basic | 0.69 0.74 | 487.0 |
| 18 | 6-Methyl-imidazo[2,1-b]thiazole-5-carboxylic acid {(1R,3S,4S)-2-[5-(3-fluoro-phenyl)-2-methyl-thiazole-4-carbonyl]-2-aza-bicyclo[2.2.1]hept-3-ylmethyl}-amide | acidic | 0.86 0.91 | 509.9 |
| 19 | 6-Methyl-imidazo[2,1-b]thiazole-5-carboxylic acid {(1R,3S,4S)-2-[5-(4-fluoro-phenyl)-2-methyl-thiazole-4-carbonyl]-2-aza-bicyclo[2.2.1]hept-3-ylmethyl}-amide | acidic | 0.85 0.90 | 509.9 |
| 20 | 6-Methyl-imidazo[2,1-b]thiazole-5-carboxylic acid [(1R,3S,4S)-2-(2-methyl-5-p-tolyl-thiazole-4-carbonyl)-2-aza-bicyclo[2.2.1]hept-3-ylmethyl]-amide | acidic | 0.87 0.92 | 506.0 |
| 21 | 6-Methyl-imidazo[2,1-b]thiazole-5-carboxylic acid {(1R,3S,4S)-2-[5-(3,5-dimethyl-phenyl)-2-methyl-thiazole-4-carbonyl]-2-aza-bicyclo[2.2.1]hept-3-ylmethyl}-amide | acidic | 0.90 0.96 | 520.0 |
| 22 | 6-Methyl-imidazo[2,1-b]thiazole-5-carboxylic acid {(1R,3S,4S)-2-[5-(2,3-dichloro-phenyl)-2-methyl-thiazole-4-carbonyl]-2-aza-bicyclo[2.2.1]hept-3-ylmethyl}-amide | acidic | 0.97 | 559.8 |
| 23 | 6-Methyl-imidazo[2,1-b]thiazole-5-carboxylic acid {(1R,3S,4S)-2-[5-(3-bromo-4-fluoro-phenyl)-2-methyl-thiazole-4-carbonyl]-2-aza-bicyclo[2.2.1]hept-3-ylmethyl}-amide | acidic | 0.91 0.95 | 587.7 |
| 24 | 6-Methyl-imidazo[2,1-b]thiazole-5-carboxylic acid {(1R,3S,4S)-2-[5-(3,4-difluoro-phenyl)-2-methyl-thiazole-4-carbonyl]-2-aza-bicyclo[2.2.1]hept-3-ylmethyl}-amide | acidic | 0.88 0.92 | 527.9 |
| 25 | 6-Methyl-imidazo[2,1-b]thiazole-5-carboxylic acid {(1R,3S,4S)-2-[5-(3-fluoro-2-methyl-phenyl)-2-methyl-thiazole-4-carbonyl]-2-aza-bicyclo[2.2.1]hept-3-ylmethyl}-amide | acidic | 0.93 | 523.9 |
| 26 | 6-Methyl-imidazo[2,1-b]thiazole-5-carboxylic acid {(1R,3S,4S)-2-[5-(3,4-dichloro-phenyl)-2-methyl-thiazole-4-carbonyl]-2-aza-bicyclo[2.2.1]hept-3-ylmethyl}-amide | acidic | 0.94 0.98 | 559.8 |
| 27 | 6-Methyl-imidazo[2,1-b]thiazole-5-carboxylic acid {(1R,3S,4S)-2-[5-(3,4-dimethyl-phenyl)-2-methyl-thiazole-4-carbonyl]-2-aza-bicyclo[2.2.1]hept-3-ylmethyl}-amide | acidic | 0.90 0.96 | 520.0 |
| 28 | 6-Methyl-imidazo[2,1-b]thiazole-5-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 0.85 0.92 | 521.0 |
| 29 | 6-Methyl-imidazo[2,1-b]thiazole-5-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 0.88 0.95 | 538.9 |
| 30 | 6-Methyl-imidazo[2,1-b]thiazole-5-carboxylic acid [(1R,3S,4S)-2-(2-methyl-5-phenyl-thiazole-4-carbonyl)-2-aza-bicyclo[2.2.1]hept-3-ylmethyl]-amide | acidic | 0.84 0.89 | 492.0 |
| 31 | 6-Methyl-imidazo[2,1-b]thiazole-5-carboxylic acid [(1R,3S,4S)-2-(2-cyclopropyl-5-phenyl-thiazole-4-carbonyl)-2-aza-bicyclo[2.2.1]hept-3-ylmethyl]-amide | acidic | 0.89 0.96 | 518.0 |
| 32 | 6-Methyl-imidazo[2,1-b]thiazole-5-carboxylic acid {(1R,3S,4S)-2-[5-(3-chloro-phenyl)-thiazole-4-carbonyl]-2-aza-bicyclo[2.2.1]hept-3-ylmethyl}-amide | acidic | 0.87 0.90 | 512.4 |
| 33 | 6-Methyl-imidazo[2,1-b]thiazole-5-carboxylic acid {(1R,3S,4S)-2-[5-(3-trifluoromethyl-phenyl)-thiazole-4-carbonyl]-2-aza-bicyclo[2.2.1]hept-3-ylmethyl}-amide | acidic | 0.90 0.93 | 545.9 |
| 34 | 6-Methyl-imidazo[2,1-b]thiazole-5-carboxylic acid {(1R,3S,4S)-2-[5-(3-methoxy-phenyl)-thiazole-4-carbonyl]-2-aza-bicyclo[2.2.1]hept-3-ylmethyl}-amide | acidic | 0.83 0.88 | 507.9 |
| 35 | 6-Methyl-imidazo[2,1-b]thiazole-5-carboxylic acid {(1R,3S,4S)-2-[5-(4-fluoro-phenyl)- | acidic | 0.83 0.87 | 495.9 |

| Example | Name | LC-MS eluent | t_R [min] | [M + H]+ |
|---|---|---|---|---|
| | thiazole-4-carbonyl]-2-aza-bicyclo[2.2.1]hept-3-ylmethyl}-amide | | | |
| 36 | 6-Methyl-imidazo[2,1-b]thiazole-5-carboxylic acid {(1R,3S,4S)-2-[5-(2-fluoro-phenyl)-thiazole-4-carbonyl]-2-aza-bicyclo[2.2.1]hept-3-ylmethyl}-amide | acidic | 0.87 | 495.9 |
| 37 | 6-Methyl-imidazo[2,1-b]thiazole-5-carboxylic acid {(1R,3S,4S)-2-[5-(3-fluoro-4-methyl-phenyl)-2-methyl-thiazole-4-carbonyl]-2-aza-bicyclo[2.2.1]hept-3-ylmethyl}-amide | acidic | 0.89 0.94 | 523.9 |

Starting from 2-Ethyl-5-methyl-2H-pyrazole-3-carboxylic acid [(1R,3S,4S)-1-(2-aza-bicyclo[2.2.1]hept-3-yl)methyl]-amide:

| Example | Name | LC-MS eluent | t_R [min] | [M + H]+ |
|---|---|---|---|---|
| 38 | 2-Ethyl-5-methyl-2H-pyrazole-3-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.92 | 498.1 |
| 39 | 2-Ethyl-5-methyl-2H-pyrazole-3-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.78 | 483.0 |
| 40 | 2-Ethyl-5-methyl-2H-pyrazole-3-carboxylic acid [(1R,3S,4S)-2-(biphenyl-2-carbonyl)-2-aza-bicyclo[2.2.1]hept-3-ylmethyl]-amide | basic | 0.82 0.91 | 443.1 |
| 41 | 2-Ethyl-5-methyl-2H-pyrazole-3-carboxylic acid [(1R,3S,4S)-2-(3'-chloro-biphenyl-2-carbonyl)-2-aza-bicyclo[2.2.1]hept-3-ylmethyl]-amide | basic | 0.94 | 477.1 |

Starting from [(1R,3S,4S)-1-(2-Aza-bicyclo[2.2.1]hept-3-yl)methyl]-(5-bromo-pyrimidin-2-yl)-amine:

| Example | Name | LC-MS eluent | t_R [min] | [M + H]+ |
|---|---|---|---|---|
| 42 | {(1R,3S,4S)-3-[(5-Bromo-pyrimidin-2-ylamino)-methyl]-2-aza-bicyclo[2.2.1]hept-2-yl}-(2-methyl-5-m-tolyl-thiazol-4-yl)-methanone | acidic | 1.03 1.10 | 497.9 |
| 43 | [5-(3-Bromo-4-fluoro-phenyl)-2-methyl-thiazol-4-yl]-{(1R,3S,4S)-3-[(5-bromo-pyrimidin-2-ylamino)-methyl]-2-aza-bicyclo[2.2.1]hept-2-yl}-methanone | acidic | 1.07 1.12 | 580.7 |
| 44 | {(1R,3S,4S)-3-[(5-Bromo-pyrimidin-2-ylamino)-methyl]-2-aza-bicyclo[2.2.1]hept-2-yl}-[5-(3,4-dimethyl-phenyl)-2-methyl-thiazol-4-yl]-methanone | acidic | 1.06 1.13 | 511.5 |
| 45 | {(1R,3S,4S)-3-[(5-Bromo-pyrimidin-2-ylamino)-methyl]-2-aza-bicyclo[2.2.1]hept-2-yl}-[2-dimethylamino-5-(3-fluoro-phenyl)-thiazol-4-yl]-methanone | acidic | 1.03 1.11 | 530.8 |
| 46 | {(1R,3S,4S)-3-[(5-Bromo-pyrimidin-2-ylamino)-methyl]-2-aza-bicyclo[2.2.1]hept-2-yl}-(2-methyl-5-phenyl-thiazol-4-yl)-methanone | acidic | 1.00 1.06 | 483.8 |
| 47 | {(1R,3S,4S)-3-[(5-Bromo-pyrimidin-2-ylamino)-methyl]-2-aza-bicyclo[2.2.1]hept-2-yl}-(2-cyclopropyl-5-phenyl-thiazol-4-yl)-methanone | acidic | 1.05 1.12 | 509.9 |
| 48 | {(1R,3S,4S)-3-[(5-Bromo-pyrimidin-2-ylamino)-methyl]-2-aza-bicyclo[2.2.1]hept-2- | acidic | 1.04 1.08 | 503.8 |

| | | LC-MS | | |
|---|---|---|---|---|
| Example | Name | eluent | $t_R$ [min] | $[M + H]^+$ |
| | yl}-[5-(3-chloro-phenyl)-thiazol-4-yl]-methanone | | | |
| 49 | {(1R,3S,4S)-3-[(5-Bromo-pyrimidin-2-ylamino)-methyl]-2-aza-bicyclo[2.2.1]hept-2-yl}-[5-(3-fluoro-4-methyl-phenyl)-2-methyl-thiazol-4-yl]-methanone | acidic | 1.06 1.11 | 515.8 |

C.2 Synthesis of carboxylic amide derivatives (general procedure II)

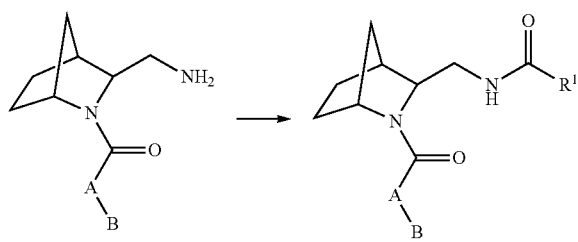

To a solution of the respective carboxylic acid (0.030 mmol, 1.2 eq) in DMF (0.50 mL) is added successively DIPEA (0.025 mmol, 1.0 eq) and a solution of TBTU (0.030 mmol, 1.2 eq) in DMF (0.50 mL). The obtained mixture is treated with a solution of the respective 2-aza-bicyclo[2.2.1]heptane derivative (0.025 mmol, 1.0 eq) and DIPEA (0.050 mmol, 2.0 eq) in DMF (0.50 mL). The mixture is shaken over night and purified by prep. HPLC to give the respective amide derivative.

Starting from ((1R,3S,4S)-3-Aminomethyl-2-aza-bicyclo[2.2.1]hept-2-yl)-(2-methyl-5-m-tolyl-thiazol-4-yl)-methanone:

| | | LC-MS | | |
|---|---|---|---|---|
| Example | Name | eluent | $t_R$ [min] | $[M + H]^+$ |
| 50 | 2,3-Dihydro-thieno[3,4-b][1,4]dioxine-5-carboxylic acid [(1R,3S,4S)-2-(2-methyl-5-m-tolyl-thiazole-4-carbonyl)-2-aza-bicyclo[2.2.1]hept-3-ylmethyl]-amide | basic | 0.84 0.90 | 509.9 |
| 51 | 2-Bromo-thiazole-4-carboxylic acid [(1R,3S,4S)-2-(2-methyl-5-m-tolyl-thiazole-4-carbonyl)-2-aza-bicyclo[2.2.1]hept-3-ylmethyl]-amide | basic | 0.94 | 530.8 |
| 52 | 2,3,6,7-Tetrahydro-benzo[1,2-b;4,5-b']difuran-4-carboxylic acid [(1R,3S,4S)-2-(2-methyl-5-m-tolyl-thiazole-4-carbonyl)-2-aza-bicyclo[2.2.1]hept-3-ylmethyl]-amide | basic | 0.96 | 530.0 |

Starting from ((1R,3S,4S)-3-Aminomethyl-2-aza-bicyclo[2.2.1]hept-2-yl)-[5-(3-chloro-phenyl)-2-methyl-thiazol-4-yl]-methanone:

| | | LC-MS | | |
|---|---|---|---|---|
| Example | Name | eluent | $t_R$ [min] | $[M + H]^+$ |
| 53 | 2,3-Dihydro-thieno[3,4-b][1,4]dioxine-5-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.91 | 529.9 |
| 54 | 2-Bromo-thiazole-4-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.95 | 550.6 |
| 55 | 6-Methoxy-pyridine-2-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.97 | 496.9 |

-continued

| Example | Name | LC-MS eluent | $t_R$ [min] | $[M+H]^+$ |
|---|---|---|---|---|
| 56 | 2,3,6,7-Tetrahydro-benzo[1,2-b;4,5-b']difuran-4-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide | basic | 0.98 | 549.9 |

Starting from [2-Amino-5-(3-fluoro-phenyl)-thiazol-4-yl]-((1R,3S,4S)-3-aminomethyl-2-aza-bicyclo[2.2.1]hept-2-yl)-methanone:

| Example | Name | LC-MS eluent | $t_R$ [min] | $[M+H]^+$ |
|---|---|---|---|---|
| 57 | 2,3-Dihydro-thieno[3,4-b][1,4]dioxine-5-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.76 0.80 | 514.9 |
| 58 | 2-Bromo-thiazole-4-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.82 | 535.7 |
| 59 | 6-Methoxy-pyridine-2-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.80 0.83 | 481.9 |
| 60 | 3,4-Dihydro-2H-benzo[1,4]oxazine-5-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.81 0.85 | 507.9 |
| 61 | 2,3,6,7-Tetrahydro-benzo[1,2-b;4,5-b']difuran-4-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide | basic | 0.82 0.84 | 535.0 |

C.3 Synthesis of carboxylic amide derivatives (general procedure III)

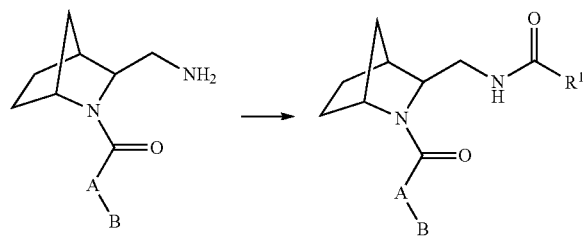

To a solution of the respective carboxylic acid (0.13 mmol, 1.0 eq) in MeCN (1.0 mL) is added TBTU (0.15 mmol, 1.1 eq). DIPEA (0.33 mmol) is added and the mixture is stirred for 15 min. The obtained mixture is treated with a solution of the respective 2-aza-bicyclo[2.2.1]heptane derivative (0.13 mmol, 1.0 eq) and DIPEA (0.33 mmol) in MeCN (1.0 mL). The mixture is shaken over night and purified by prep. HPLC to give the respective amide derivative.

Starting from ((1R,3S,4S)-3-Aminomethyl-2-aza-bicyclo[2.2.1]hept-2-yl)-(2-dimethylamino-5-phenyl-thiazol-4-yl)-methanone:

| Example | Name | LC-MS eluent | $t_R$ [min] | $[M+H]^+$ |
|---|---|---|---|---|
| 62 | 1-Methyl-1H-benzoimidazole-2-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 1.00 1.09 | 515.7 |
| 63 | 1-Methyl-1H-indazole-3-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 0.98 1.09 | 515.7 |

-continued

| Example | Name | LC-MS eluent | $t_R$ [min] | $[M + H]^+$ |
|---|---|---|---|---|
| 64 | Imidazo[1,2-a]pyridine-3-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 0.78 0.87 | 501.1 |
| 65 | 3-Methyl-1H-indene-2-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 1.06 1.17 | 513.3 |
| 66 | 2-Methyl-benzooxazole-4-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 1.00 1.10 | 516.6 |
| 67 | Benzothiazole-7-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 0.90 1.05 | 518.5 |
| 68 | 6-Methyl-pyrrolo[2,1-b]thiazole-7-carboxylic acid [(1R,3S,4S)-2-(2-dimethylamino-5-phenyl-thiazole-4-carbonyl)-2-aza-bicyclo[2.2.1]hept-3-ylmethyl]-amide | acidic | 0.91 1.05 | 520.4 |

Starting from 41R,3S,4S)-3-Aminomethyl-2-aza-bicyclo[2.2.1]hept-2-yl)-[2-dimethylamino-5-(3-fluoro-phenyl)-thiazol-4-yl]-methanone:

| Example | Name | LC-MS eluent | $t_R$ [min] | $[M + H]^+$ |
|---|---|---|---|---|
| 69 | 1-Methyl-1H-benzoimidazole-2-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 1.04 1.12 | 533.5 |
| 70 | 1H-Indazole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 0.96 1.06 | 519.4 |
| 71 | Benzothiazole-7-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 0.94 1.08 | 536.4 |
| 72 | 1-Methyl-1H-indazole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 1.03 1.12 | 533.5 |
| 73 | 1,2-Dimethyl-1H-indole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 1.02 1.13 | 546.5 |
| 74 | 1H-Indole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 0.93 1.05 | 518.4 |
| 75 | Benzo[d]isoxazole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 1.03 1.14 | 520.6 |
| 76 | 3-Methyl-1H-indene-2-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 1.10 1.19 | 531.5 |
| 77 | 5-Fluoro-1-methyl-1H-indole-2-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 1.10 1.20 | 550.6 |
| 78 | 1,2-Dimethyl-1H-benzoimidazole-5-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide | acidic | 0.76 0.87 | 547.6 |
| 79 | 2-Methyl-benzooxazole-4-carboxylic acid {(1R,3S,4S)-2-[2-dimethylamino-5-(3-fluoro- | acidic | 1.04 1.13 | 534.4 |

| | | LC-MS | |
|---|---|---|---|
| Example Name | eluent | $t_R$ [min] | [M + H]+ |
| phenyl)-thiazole-4-carbonyl]-2-aza-bicyclo[2.2.1]hept-3-ylmethyl}-amide | | | |

The following examples were prepared according to the methods described above by selecting the most appropriate methodology and pathway and combining the respective building blocks (LC-MS-data were recorded under acidic conditions):

Example 80

Benzothiazole-7-carboxylic acid {(R,S,S)-2-[5-(3-chloro-phenyl)-2-methoxy-thiazole-4-carbonyl]-2-aza-bicyclo[2.2.1]hept-3-ylmethyl}-amide; LC-MS: $t_R$=1.14 min; [M+H]+=539.03.

Example 81

Benzothiazole-7-carboxylic acid {(R,S,S)-2-[5-(3-chloro-phenyl)-2-ethoxy-thiazole-4-carbonyl]-2-aza-bicyclo[2.2.1]hept-3-ylmethyl}-amide; LC-MS: $t_R$=1.18 min; [M+H]+=553.27.

Example 82

Benzothiazole-7-carboxylic acid {(R,S,S)-2-[5-(3-chloro-phenyl)-2-(2-methoxy-ethoxy)-thiazole-4-carbonyl]-2-aza-bicyclo[2.2.1]hept-3-ylmethyl}-amide; LC-MS: $t_R$=1.13 min; [M+H]+=583.00.

Example 83

Benzothiazole-7-carboxylic acid {(R,S,S)-[2-(2-cyclopropyl-5-phenyl-thiazole-4-carbonyl)-2-aza-bicyclo[2.2.1]hept-3-ylmethyl]}-amide; LC-MS: $t_R$=1.11 min; [M+H]+=515.37.

Example 84

Benzothiazole-7-carboxylic acid {(R,R,S)-2-[2-cyclopropyl-5-(3-fluoro-phenyl)-thiazole-4-carbonyl]-2-aza-bicyclo[2.2.1]hept-3-ylmethyl}-amide; LC-MS: $t_R$=1.12 min; [M+H]+=533.5.

Example 85

Benzothiazole-7-carboxylic acid {(R,R,S)-2-[2-methyl-5-(3-trifluoromethyl-phenyl)-thiazole-4-carbonyl]-2-aza-bicyclo[2.2.1]hept-3-ylmethyl}-amide; LC-MS: $t_R$=1.11 min; [M+H]+=557.43.

Example 86

Benzothiazole-7-carboxylic acid {(R,R,S)-2-[2-dimethylamino-5-(3,4-dimethyl-phenyl)-thiazole-4-carbonyl]-2-aza-bicyclo[2.2.1]hept-3-ylmethyl}-amide; LC-MS: $t_R$=1.12 min; [M+H]+=546.46.

Example 87

Benzothiazole-7-carboxylic acid {(R,R,S)-2-[5-(3-chloro-phenyl)-2-dimethylamino-thiazole-4-carbonyl]-2-aza-bicyclo[2.2.1]hept-3-ylmethyl}-amide; LC-MS: $t_R$=1.13 min; [M+H]+=552.05.

Example 88

Benzothiazole-7-carboxylic acid {(R,R,S)-2-[5-(3-chloro-phenyl)-2-(ethyl-methyl-amino)-thiazole-4-carbonyl]-2-aza-bicyclo[2.2.1]hept-3-ylmethyl}-amide; LC-MS: $t_R$=1.19 min; [M+H]+=566.27.

Example 89

Benzothiazole-7-carboxylic acid {(1R,3S,4S)-2-[5-(3-chloro-phenyl)-2-diethylamino-thiazole-4-carbonyl]-2-aza-bicyclo[2.2.1]hept-3-ylmethyl}-amide; LC-MS: $t_R$=1.25 min; [M+H]+=580.22.

Example 90

Benzothiazole-7-carboxylic acid [(1R,3S,4S)-2-(3-p-tolyl-pyrazine-2-carbonyl)-2-aza-bicyclo[2.2.1]hept-3-ylmethyl]-amide; LC-MS: $t_R$=0.97 min; [M+H]+=484.51.

Example 91

Benzothiazole-7-carboxylic acid {(1R,3S,4S)-2-[3-(4-methoxy-phenyl)-thiophene-2-carbonyl]-2-aza-bicyclo[2.2.1]hept-3-ylmethyl}-amide; LC-MS: $t_R$=1.06 min; [M+H]+=504.41.

Example 92

Benzothiazole-7-carboxylic acid {(1R,3S,4S)-2-[3-(3-methoxy-phenyl)-thiophene-2-carbonyl]-2-aza-bicyclo[2.2.1]hept-3-ylmethyl}-amide; LC-MS: $t_R$=1.06 min; [M+H]+=504.48.

Example 93

Benzothiazole-7-carboxylic acid {(1R,3S,4S)-2-[3-(3,4-dimethoxy-phenyl)-thiophene-2-carbonyl]-2-aza-bicyclo[2.2.1]hept-3-ylmethyl}-amide; LC-MS: $t_R$=1.00 min; [M+H]+=534.55.

Example 94

Benzothiazole-7-carboxylic acid [(1R,3S,4S)-2-(3-benzo[1,3]dioxol-5-yl-thiophene-2-carbonyl)-2-aza-bicyclo[2.2.1]hept-3-ylmethyl]-amide; LC-MS: $t_R$=1.04 min; [M+H]+=518.35.

Example 95

Benzothiazole-7-carboxylic acid {(1R,3S,4S)-2-[2-dimethylamino-5-(2-fluoro-phenyl)-thiazole-4-carbonyl]-2-aza-bicyclo[2.2.1]hept-3-ylmethyl}-amide; LC-MS: $t_R$=1.07 min; [M+H]$^+$=536.55.

Example 96

Benzothiazole-7-carboxylic acid {(1R,3S,4S)-2-[2-dimethylamino-5-(4-fluoro-phenyl)-thiazole-4-carbonyl]-2-aza-bicyclo[2.2.1]hept-3-ylmethyl}-amide; LC-MS: $t_R$=1.07 min; [M+H]$^+$=536.47.

Example 97

Benzothiazole-7-carboxylic acid {(1R,3S,4S)-2-[2-dimethylamino-5-(3-methoxy-phenyl)-thiazole-4-carbonyl]-2-aza-bicyclo[2.2.1]hept-3-ylmethyl}-amide; LC-MS: $t_R$=1.06 min; [M+H]$^+$=548.33.

Example 98

Benzothiazole-7-carboxylic acid [(1R,3S,4S)-2-(2-cyclopropyl-5-p-tolyl-thiazole-4-carbonyl)-2-aza-bicyclo[2.2.1]hept-3-ylmethyl]-amide; LC-MS: $t_R$=1.18 min; [M+H]$^+$=529.34.

Example 99

Benzothiazole-7-carboxylic acid {(1R,3S,4S)-2-[2-cyclopropyl-5-(2-fluoro-phenyl)-thiazole-4-carbonyl]-2-aza-bicyclo[2.2.1]hept-3-ylmethyl}-amide; LC-MS: $t_R$=1.13 min; [M+H]$^+$=533.50.

Example 100

Benzothiazole-7-carboxylic acid [(1R,3S,4S)-2-(2-cyclopropyl-5-m-tolyl-thiazole-4-carbonyl)-2-aza-bicyclo[2.2.1]hept-3-ylmethyl]-amide; LC-MS: $t_R$=1.17 min; [M+H]$^+$=529.60.

Example 101

Benzothiazole-7-carboxylic acid {(1R,3S,4S)-2-[2-cyclopropyl-5-(3-fluoro-4-methyl-phenyl)-thiazole-4-carbonyl]-2-aza-bicyclo[2.2.1]hept-3-ylmethyl}-amide; LC-MS: $t_R$=1.19 min; [M+H]$^+$=547.57.

Example 102

Benzothiazole-7-carboxylic acid {(1R,3S,4S)-2-[5-(3-chloro-phenyl)-2-methylamino-thiazole-4-carbonyl]-2-aza-bicyclo[2.2.1]hept-3-ylmethyl}-amide; LC-MS: $t_R$=1.02 min; [M+H]$^+$=538.20.

Example 103

Benzothiazole-7-carboxylic acid {(1R,3S,4S)-2-[5-(3-chloro-phenyl)-2-ethylamino-thiazole-4-carbonyl]-2-aza-bicyclo[2.2.1]hept-3-ylmethyl}-amide; LC-MS: $t_R$=1.07 min; [M+H]$^+$=552.20.

Example 104

Benzothiazole-7-carboxylic acid {(1R,3S,4S)-2-[2-methyl-5-(3-trifluoromethoxy-phenyl)-oxazole-4-carbonyl]-2-aza-bicyclo[2.2.1]hept-3-ylmethyl}-amide; LC-MS: $t_R$=1.13 min; [M+H]$^+$=557.13.

Example 105

Benzo[d]isothiazole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide; LC-MS: $t_R$=1.12 min; [M+H]$^+$=536.20.

Example 106

5-Ethyl-3-methyl-isoxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide; LC-MS: $t_R$=1.06 min; [M+H]$^+$=511.80.

Example 107

3-Ethyl-5-methyl-isoxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide; LC-MS: $t_R$=1.05 min; [M+H]$^+$=511.86.

Example 108

Quinoxaline-5-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide; LC-MS: $t_R$=1.05 min; [M+H]$^+$=531.11.

Example 109

Benzothiazole-7-carboxylic acid {(1R,3S,4S)-2-[3-(1H-indol-6-yl)-pyrazine-2-carbonyl]-2-aza-bicyclo[2.2.1]hept-3-ylmethyl}-amide; LC-MS: $t_R$=0.95 min; [M+H]$^+$=509.17.

Example 110

Benzothiazole-7-carboxylic acid {(1S,3R,4R)-2-[5-(2-fluoro-phenyl)-2-pyrrolidin-1-yl-thiazole-4-carbonyl]-2-aza-bicyclo[2.2.1]hept-3-ylmethyl}-amide; LC-MS: $t_R$=1.12 min; [M+H]$^+$=562.69.

Example 111

Benzothiazole-7-carboxylic acid [(1S,3R,4R)-2-(2-dimethylamino-5-m-tolyl-thiazole-4-carbonyl)-2-aza-bicyclo[2.2.1]hept-3-ylmethyl]-amide; LC-MS: $t_R$=1.11 min; [M+H]$^+$=532.58.

Example 112

Benzothiazole-7-carboxylic acid {(1S,3R,4R)-2-[2-(ethyl-methyl-amino)-5-(3-methoxy-phenyl)-thiazole-4-carbonyl]-2-aza-bicyclo[2.2.1]hept-3-ylmethyl}-amide; LC-MS: $t_R$=1.12 min; [M+H]$^+$=562.24.

Example 113

Benzothiazole-7-carboxylic acid {(1S,3R,4R)-2-[5-(3-bromo-4-fluoro-phenyl)-2-dimethylamino-thiazole-4-carbonyl]-2-aza-bicyclo[2.2.1]hept-3-ylmethyl}-amide; LC-MS: $t_R$=1.15 min; [M+H]$^+$=616.13.

Example 114

Benzothiazole-7-carboxylic acid {(1S,3R,4R)-2-[5-(4-fluoro-phenyl)-2-pyrrolidin-1-yl-thiazole-4-carbonyl]-2-aza-bicyclo[2.2.1]hept-3-ylmethyl}-amide; LC-MS: $t_R$=1.11 min; [M+H]$^+$=562.49.

Example 115

Benzothiazole-7-carboxylic acid {(1S,3R,4R)-2-[2-dimethylamino-5-(4-fluoro-phenyl)-thiazole-4-carbonyl]-2-aza-bicyclo[2.2.1]hept-3-ylmethyl}-amide; LC-MS: $t_R$=1.07 min; [M+H]$^+$=536.13.

Example 116

Benzothiazole-7-carboxylic acid {(1S,3R,4R)-2-[2-diethylamino-5-(2-fluoro-phenyl)-thiazole-4-carbonyl]-2-aza-bicyclo[2.2.1]hept-3-ylmethyl}-amide; LC-MS: $t_R$=1.19 min; [M+H]$^+$=564.73.

Example 117

Benzothiazole-7-carboxylic acid {(1S,3R,4R)-2-[2-dimethylamino-5-(3-fluoro-4-methyl-phenyl)-thiazole-4-carbonyl]-2-aza-bicyclo[2.2.1]hept-3-ylmethyl}-amide; LC-MS: $t_R$=1.14 min; [M+H]$^+$=550.64.

Example 118

Benzothiazole-7-carboxylic acid {(1S,3R,4R)-2-[2-(ethyl-methyl-amino)-5-(4-fluoro-phenyl)-thiazole-4-carbonyl]-2-aza-bicyclo[2.2.1]hept-3-ylmethyl}-amide; LC-MS: $t_R$=1.13 min; [M+H]$^+$=550.63.

Example 119

Benzothiazole-7-carboxylic acid [(1S,3R,4R)-2-(2-dimethylamino-5-p-tolyl-thiazole-4-carbonyl)-2-aza-bicyclo[2.2.1]hept-3-ylmethyl]-amide; LC-MS: $t_R$=1.11 min; [M+H]$^+$=532.62.

Example 120

Benzothiazole-7-carboxylic acid {(1S,3R,4R)-2-[2-dimethylamino-5-(3-trifluoromethyl-phenyl)-thiazole-4-carbonyl]-2-aza-bicyclo[2.2.1]hept-3-ylmethyl}-amide; LC-MS: $t_R$=1.15 min; [M+H]$^+$=586.60.

Example 121

Benzothiazole-7-carboxylic acid {(1S,3R,4R)-2-[2-diethylamino-5-(4-fluoro-phenyl)-thiazole-4-carbonyl]-2-aza-bicyclo[2.2.1]hept-3-ylmethyl}-amide; LC-MS: $t_R$=1.18 min;
[M+H]$^+$=564.51.

II—Biological Assays

In Vitro Assay

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20'000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH:water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates, first in DMSO, then in HBSS containing 0.1% bovine serum albumin (BSA), $NaHCO_3$: 0.375 g/l and 20 mM HEPES.

On the day of the assay, 50 µl of staining buffer (HBSS containing 1% FCS, 20 mM HEPES, $NaHCO_3$: 0.375 g/l, 5 mM probenecid (Sigma) and 3 µM of the fluorescent calcium indicator fluo-4 AM (1 mM stock solution in DMSO, containing 10% pluronic) is added to each well.

The 384-well cell-plates are incubated for 50 min at 37° C. in 5% $CO_2$ followed by equilibration at rt for 30-120 min before measurement.

Within the Fluorescent Imaging Plate Reader (FLIPR2 or FLIPR Tetra, Molecular Devices), antagonists are added to the plate in a volume of 10 µl/well, incubated for 10 min and finally 10 µl/well of agonist is added. Fluorescence is measured for each well at 1 second intervals, and the height of each fluorescence peak is compared to the height of the fluorescence peak induced by 3 nM orexin-A with vehicle in place of antagonist. For each antagonist, the $IC_{50}$ value (the concentration of compound needed to inhibit 50% of the agonistic response) is determined. Optimized conditions may be achieved by adjustment of pipetting speed and cell splitting regime. The calculated $IC_{50}$ values of the compounds may fluctuate depending on the daily cellular assay performance. Fluctuations of this kind are known to those skilled in the art.

Antagonistic activities ($IC_{50}$ values) of all exemplified compounds are below 1000 nM with respect to the $OX_1$ and/or the $OX_2$ receptor. Antagonistic activities ($IC_{50}$ values) of 116 exemplified compounds are in the range of 6-8916 nM with an average of 730 nM with respect to the OX1 receptor (5 compounds have been measured with an $IC_{50}$ value>10000 nM). $IC_{50}$ values of 118 exemplified compounds are in the range of 10-9479 nM with an average of 469 nM with respect to the OX2 receptor (3 compounds have been measured with an $IC_{50}$ value>10000 nM). Antagonistic activities of selected compounds are displayed in Table 1.

TABLE 1

| Compound of Example | $OX_1$ $IC_{50}$ (nM) | $OX_2$ $IC_{50}$ (nM) |
| --- | --- | --- |
| 1 | 59 | 622 |
| 5 | 149 | 29 |
| 11 | 75 | 2135 |
| 31 | 138* | 55* |
| 35 | 278* | 808* |
| 40 | >10000 | 441 |
| 46 | 488* | 364* |
| 63 | 307* | 61* |
| 79 | 64*[1) | 71*[1) |
| 80 | 80* | 15* |
| 94 | 1269* | 81* |
| 97 | 12*[1) | 14*[1) |
| 104 | 305* | 37* |
| 105 | 65* | 421* |
| 109 | 707* | 19* |
| 110 | 23* | 30* |
| 118 | 117* | 32* |

$IC_{50}$ values measured with FLIPR 2 or, if marked with *, with FLIPR Tetra;
[1)] geometric mean from n = 2 values;

The invention claimed is:
1. A compound of formula (I) wherein the stereogenic centers are in Absolute (1R,3S,4S)-configuration

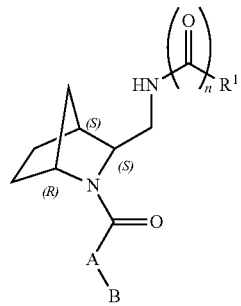

Formula (I)

wherein
A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen, $(C_{1-4})$alkoxy-$(C_{1-4})$alkoxy, and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine;
B represents an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, trifluoromethyl, trifluoromethoxy, —$NR^4R^5$, —$NHSO_2$—$(C_{1-4})$alkyl, —$N(R^4)C(O)R^5$ and halogen; or B represents a benzo [1,3]dioxolyl group;
n represents the integer 0 or 1;
$R^1$ represents heterocyclyl, wherein the heterocyclyl is unsubstituted or mono-, di-, or tri-substituted wherein the substituents are independently selected from the group consisting of $(C_{1-4})$alkyl, $(C_{1-4})$alkoxy, halogen, trifluoromethyl and —$NR^4R^5$; or
$R^1$ represents a 1H-indenyl, a 2,3-dihydro-benzofuranyl-, a benzo[1,3]dioxolyl-, a 2,3-dihydro-benzo [1,4]dioxinyl-, a 4H-benzo[1,3]dioxinyl-, a 2H-chromenyl-, a chromanyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group; wherein said groups are unsubstituted, mono- or di-substituted wherein the substituents are independently selected from the group consisting of $(C_{1-4})$alkyl, $(C_{1-4})$alkoxy and halogen;
$R^2$ represents hydrogen or $(C_{1-4})$alkyl;
$R^3$ represents hydrogen or $(C_{1-4})$alkyl;
or $R^2$ and $R^3$ together with the nitrogen to which they are attached to form a pyrrolidine ring;
$R^4$ represents hydrogen or $(C_{1-4})$alkyl; and
$R^5$ represents hydrogen or $(C_{1-4})$alkyl;
or a pharmaceutically acceptable salt of such a compound.
2. A compound of formula (I) according to claim 1, which is also a compound of Formula ($I_P$), wherein the stereogenic centers are in absolute (1R,3S,4S)-configuration

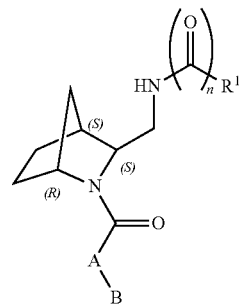

Formula ($I_P$)

wherein
A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen, and unsubstituted or independently mono- or di-substituted phenyl or pyridyl, wherein the substituents are independently selected from the group consisting of $(C_{1-4})$alkyl, $(C_{1-4})$alkoxy, trifluoromethyl, trifluoromethoxy, fluorine and chlorine;
B represents an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{1-4})$alkoxy, trifluoromethyl, —$NR^4R^5$, —$NHSO_2$—$(C_{1-4})$alkyl, —$N(R^4)C(O)R^5$ and halogen;
n represents the integer 0 or 1;
$R^1$ represents heterocyclyl, wherein the heterocyclyl is unsubstituted or mono-, di-, or tri-substituted wherein the substituents are independently selected from the group consisting of $(C_{1-4})$alkyl, $(C_{1-4})$alkoxy, halogen, trifluoromethyl and —$NR^4R^5$; or
$R^1$ represents a 1H-indenyl, a 2,3-dihydro-benzofuranyl-, a benzo[1,3]dioxolyl-, a 2,3-dihydro-benzo[1,4]dioxinyl-, a 4H-benzo[1,3]dioxinyl-, a 2H-chromenyl-, a chromanyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group; wherein said groups are unsubstituted, mono- or di-substituted wherein the substituents are independently selected from the group consisting of $(C_{1-4})$alkyl, $(C_{1-4})$alkoxy and halogen;
$R^2$ represents hydrogen or $(C_{1-4})$alkyl; and
$R^3$ represents hydrogen or $(C_{1-4})$alkyl;
$R^4$ represents hydrogen or $(C_{1-4})$alkyl; and
$R^5$ represents hydrogen or $(C_{1-4})$alkyl;
or a pharmaceutically acceptable salt of such a compound.
3. A compound according to claim 1, wherein n represents the integer 1;
or a pharmaceutically acceptable salt of such a compound.
4. A compound according to claim 1, wherein
A represents phenyl or 5- to 6-membered monocyclic heterocyclyl, wherein the phenyl or heterocyclyl is unsubstituted or mono- or di-substituted, wherein the substituents are independently selected from the group consisting of $(C_{1-4})$alkyl, $(C_{3-6})$cycloalkyl, $(C_{1-4})$alkoxy, $NR^2R^3$ and halogen;
or a pharmaceutically acceptable salt of such a compound.
5. A compound according to claim 1, wherein
B represents aryl, wherein the aryl is unsubstituted or mono-, di-, or tri-substituted, wherein the substituents are independently selected from the group consisting of (C$_{1-4}$)alkyl, (C$_{1-4}$)alkoxy, trifluoromethyl and halogen;
or a pharmaceutically acceptable salt of such a compound.

6. A compound according to claim 1, wherein
R$^1$ represents heterocyclyl, wherein the heterocyclyl is unsubstituted or independently mono-, di-, or tri-substituted, wherein the substituents are independently selected from the group consisting of (C$_{1-4}$)alkyl, (C$_{1-4}$) alkoxy and halogen; or
R$^1$ represents a 1H-indenyl, a 2,3-dihydro-benzo[1,4]dioxinyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group, wherein said groups are unsubstituted or mono- or di-substituted wherein the substituents are independently selected from the group consisting of (C$_{1-4}$)alkyl, (C$_{1-4}$)alkoxy and halogen;
or a pharmaceutically acceptable salt of such a compound.

7. A compound according to claim 1, wherein
A represents 5- to 6-membered monocyclic heterocyclyl, wherein the heterocyclyl is unsubstituted or mono-substituted wherein the substituent is selected from the group consisting of (C$_{1-4}$)alkyl, (C$_{3-6}$)cycloalkyl and NR$^2$R$^3$;
or a pharmaceutically acceptable salt of such a compound.

8. A compound according to claim 1, wherein R$^1$ represents heterocyclyl selected from isoxazolyl, thiazolyl, pyrazolyl, pyridyl, indolyl, benzofuranyl, benzothiophenyl, indazolyl, benzimidazolyl, benzoxazolyl, benzisoxazolyl, benzothiazolyl, benzoisothiazolyl, benzothiadiazolyl, quinoxalinyl, quinolinyl, isoquinolinyl, pyrrolo[2,1-b]thiazolyl, imidazo[1,2-a]pyridyl and imidazo[2,1-b]thiazolyl, wherein said heterocyclyl is unsubstituted or mono-, di-, or tri-substituted, wherein the substituents are independently selected from the group consisting of
(C$_{1-4}$)alkyl, (C$_{1-4}$)alkoxy and halogen;
or a pharmaceutically acceptable salt of such a compound.

9. A compound according to claim 1 selected from the group consisting of:
Quinoline-8-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide;
Quinoline-8-carboxylic acid [(1R,3S,4S)-2-(2-methyl-5-m-tolyl-thiazole-4-carbonyl)-2-aza -bicyclo[2.2.1]hept-3-ylmethyl]-amide; 0
2,3-Dihydro-benzo[1,4]dioxine-5-carboxylic acid {(1R,3S,4S)-2-[5-(3-chloro-phenyl)-2-methyl -thiazole-4-carbonyl]-2-aza-bicyclo[2.2.1]hept-3-ylmethyl}-amide;
2,3-Dihydro-benzo[1,4]dioxine-5-carboxylic acid {(1R,3S,4S)-2-[2-amino-5-(3-fluoro-phenyl) -thiazole-4-carbonyl]-2-aza-bicyclo[2.2.1]hept-3-ylmethyl}-amide;
Benzofuran-4-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide;
Benzofuran-4-carboxylic acid {(1R,3S,4S)-2-[2-amino-5-(3-fluoro-phenyl)-thiazole-4-carbonyl]-2-aza-bicyclo[2.2.1]kept-3-ylmethyl}-amide;
Benzofuran-4-carboxylic acid [(1R,3S,4S)-2-(2-methyl-4-phenyl-pyrimidine-5-carbonyl)-2-aza -bicyclo[2.2.1]hept-3-ylmethyl]-amide;
6-Methyl-imidazo[2,1-b]thiazole-5-carboxylic acid {(1R,3S,4S)-2-[5-(3-chloro-phenyl)-2-methyl-thiazole-4-carbonyl]-2-aza-bicyclo[2.2.1]hept-3-ylmethyl}-amide;
6-Methyl-imidazo[2,1-b]thiazole-5-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide;
6-Methyl-imidazo[2,1-b]thiazole-5-carboxylic acid [(1R,3S,4S)-2-(2-methyl-5-m-tolyl-thiazole-4-carbonyl)-2-aza-bicyclo[2.2.1]hept-3-ylmethyl]-amide;
6-Methyl-imidazo[2,1-b]thiazole-5-carboxylic acid [(1R,3S,4S)-2-(biphenyl-2-carbonyl)-2-aza -bicyclo[2.2.1]hept-3-ylmethyl]-amide;
6-Methyl-imidazo[2,1-b]thiazole-5-carboxylic acid {(1R,3S,4S)-2-[5-(3-fluoro-phenyl)-2-methyl-thiazole-4-carbonyl]-2-aza-bicyclo[2.2.1]hept-3-ylmethyl}-amide;
6-Methyl-imidazo[2,1-b]thiazole-5-carboxylic acid [(1R,3S,4S)-2-(2-methyl-5-p-tolyl-thiazole-4-carbonyl)-2-aza-bicyclo[2.2.1]hept-3-ylmethyl]-amide;
6-Methyl-imidazo[2,1-b]thiazole-5-carboxylic acid {(1R,3S,4S)-2-[5-(3-bromo-4-fluoro-phenyl)-2-methyl-thiazole-4-carbonyl]-2-aza-bicyclo[2.2.1]hept-3-ylmethyl}-amide;
6-Methyl-imidazo[2,1-b]thiazole-5-carboxylic acid {(1R,3S,4S)-2-[5-(3,4-dimethyl-phenyl)-2-methyl-thiazole-4-carbonyl]-2-aza-bicyclo[2.2.1]hept-3-ylmethyl}-amide;
6-Methyl-imidazo[2,1-b]thiazole-5-carboxylic acid [(1R,3S,4S)-2-(2-dimethylamino-5-phenyl-thiazole-4-carbonyl)-2-aza-bicyclo[2.2.1]hept-3-ylmethyl]-amide;
6-Methyl-imidazo[2,1-b]thiazole-5-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;
6-Methyl-imidazo[2,1-b]thiazole-5-carboxylic acid [(1R,3S,4S)-2-(2-methyl-5-phenyl-thiazole-4-carbonyl)-2-aza-bicyclo[2.2.1]hept-3-ylmethyl]-amide;
6-Methyl-imidazo[2,1-b]thiazole-5-carboxylic acid [(1R,3S,4S)-2-(2-cyclopropyl-5-phenyl-thiazole-4-carbonyl)-2-aza-bicyclo[2.2.1]hept-3-ylmethyl]-amide;
6-Methyl-imidazo[2,1-b]thiazole-5-carboxylic acid {(1R,3S,4S)-2-[5-(3-methoxy-phenyl)-thiazole-4-carbonyl]-2-aza-bicyclo[2.2.1]hept-3-ylmethyl}-amide;
2,3,6,7-Tetrahydro-benzo[1,2-b; 4,5-b']difuran-4-carboxylic acid {(1R,3S,4S)-2-[2-amino-5-(3-fluoro-phenyl)-thiazole-4-carbonyl]-2-aza-bicyclo[2.2.1]hept-3-ylmethyl}-amide;
1-Methyl-1H-benzoimidazole-2-carboxylic acid [(1R,3S,4S)-2-(2-dimethylamino-5-phenyl-thiazole-4-carbonyl)-2-aza-bicyclo[2.2.1]hept-3-ylmethyl]-amide;
1-Methyl-1H-indazole-3-carboxylic acid [(1R,3S,4S)-2-(2-dimethylamino-5-phenyl-thiazole-4-carbonyl)-2-aza-bicyclo[2.2.1]kept-3-ylmethyl]-amide;
2-Methyl-benzooxazole-4-carboxylic acid [(1R,3S,4S)-2-(2-dimethylamino-5-phenyl-thiazole-4-carbonyl)-2-aza-bicyclo[2.2.1]hept-3-ylmethyl]-amide;
Benzothiazole-7-carboxylic acid [(1R,3S,4S)-2-(2-dimethylamino-5-phenyl-thiazole-4-carbonyl)-2-aza-bicyclo[2.2.1]hept-3-ylmethyl]-amide;
6-Methyl-pyrrolo[2,1-b]thiazole-7-carboxylic acid [(1R,3S,4S)-2-(2-dimethylamino-5-phenyl-thiazole-4-carbonyl)-2-aza-bicyclo[2.2.1]hept-3-ylmethyl]-amide;
1-Methyl-1H-benzoimidazole-2-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;
Benzothiazole-7-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

1,2-Dimethyl-1H-indole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

5-Fluoro-1-methyl-1H-indole-2-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

2-Methyl-benzooxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

Benzothiazole-7-carboxylic acid {(R,S,S)-2-[5-(3-chloro-phenyl)-2-methoxy-thiazole-4-carbonyl]-2-aza-bicyclo[2.2.1]hept-3-ylmethyl}-amide;

Benzothiazole-7-carboxylic acid {(R,S,S)-2-[5-(3-chloro-phenyl)-2-ethoxy-thiazole-4-carbonyl]-2-aza-bicyclo[2.2.1]hept-3-ylmethyl}-amide;

Benzothiazole-7-carboxylic acid {(R,S,S)-2-[5-(3-chloro-phenyl)-2-(2-methoxy-ethoxy)-thiazole-4-carbonyl]-2-aza-bicyclo[2.2.1]hept-3-ylmethyl}-amide;

Benzothiazole-7-carboxylic acid {(R,S,S)-2-[2-(2-cyclopropyl-5-phenyl-thiazole-4-carbonyl)-2-aza-bicyclo[2.2.1]hept-3-ylmethyl]}-amide;

Benzothiazole-7-carboxylic acid {(R,R,S)-2-[2-cyclopropyl-5-(3-fluoro-phenyl)-thiazole-4-carbonyl]-2-aza-bicyclo[2.2.1]hept-3-ylmethyl}-amide;

Benzothiazole-7-carboxylic acid {(R,R,S)-2-[2-methyl-5-(3-trifluoromethyl-phenyl)-thiazole-4-carbonyl]-2-aza-bicyclo[2.2.1]hept-3-ylmethyl}-amide;

Benzothiazole-7-carboxylic acid {(R,R,S)-2-[2-dimethylamino-5-(3,4-dimethyl-phenyl)-thiazole-4-carbonyl]-2-aza-bicyclo[2.2.1]hept-3-ylmethyl}-amide;

Benzothiazole-7-carboxylic acid {(R,R,S)-2-[5-(3-chloro-phenyl)-2-dimethylamino-thiazole-4-carbonyl]-2-aza-bicyclo[2.2.1]hept-3-ylmethyl}-amide;

Benzothiazole-7-carboxylic acid {(R,R,S)-2-[5-(3-chloro-phenyl)-2-(ethyl-methyl-amino)-thiazole-4-carbonyl]-2-aza-bicyclo[2.2.1]hept-3-ylmethyl}-amide;

Benzothiazole-7-carboxylic acid {(1R,3S,4S)-2-[5-(3-chloro-phenyl)-2-diethylamino-thiazole-4-carbonyl]-2-aza-bicyclo[2.2.1]hept-3-ylmethyl}-amide;

Benzothiazole-7-carboxylic acid [(1R,3S,4S)-2-(3-p-tolyl-pyrazine-2-carbonyl)-2-aza-bicyclo[2.2.1]hept-3-ylmethyl]-amide;

Benzothiazole-7-carboxylic acid {(1R,3S,4S)-2-[3-(4-methoxy-phenyl)-thiophene-2-carbonyl]-2-aza-bicyclo[2.2.1]hept-3-ylmethyl}-amide;

Benzothiazole-7-carboxylic acid {(1R,3S,4S)-2-[3-(3-methoxy-phenyl)-thiophene-2-carbonyl]-2-aza-bicyclo[2.2.1]hept-3-ylmethyl}-amide;

Benzothiazole-7-carboxylic acid {(1R,3S,4S)-2-[3-(3,4-dimethoxy-phenyl)-thiophene-2-carbonyl]-2-aza-bicyclo[2.2.1]hept-3-ylmethyl}-amide;

Benzothiazole-7-carboxylic acid [(1R,3S,4S)-2-(3-benzo[1,3]dioxol-5-yl-thiophene-2-carbonyl)-2-aza-bicyclo[2.2.1]hept-3-ylmethyl]-amide;

Benzothiazole-7-carboxylic acid {(1R,3S,4S)-2-[2-dimethylamino-5-(2-fluoro-phenyl)-thiazole-4-carbonyl]-2-aza-bicyclo[2.2.1]hept-3-ylmethyl}-amide;

Benzothiazole-7-carboxylic acid {(1R,3S,4S)-2-[2-dimethylamino-5-(4-fluoro-phenyl)-thiazole-4-carbonyl]-2-aza-bicyclo[2.2.1]hept-3-ylmethyl}-amide;

Benzothiazole-7-carboxylic acid {(1R,3S,4S)-2-[2-dimethylamino-5-(3-methoxy-phenyl)-thiazole-4-carbonyl]-2-aza-bicyclo[2.2.1]hept-3-ylmethyl}-amide;

Benzothiazole-7-carboxylic acid [(1R,3S,4S)-2-(2-cyclopropyl-5-p-tolyl-thiazole-4-carbonyl)-2-aza-bicyclo[2.2.1]hept-3-ylmethyl]-amide;

Benzothiazole-7-carboxylic acid {(1R,3S,4S)-2-[2-cyclopropyl-5-(2-fluoro-phenyl)-thiazole-4-carbonyl]-2-aza-bicyclo[2.2.1]hept-3-ylmethyl}-amide;

Benzothiazole-7-carboxylic acid [(1R,3S,4S)-2-(2-cyclopropyl-5-m-tolyl-thiazole-4-carbonyl)-2-aza-bicyclo[2.2.1]hept-3-ylmethyl]-amide;

Benzothiazole-7-carboxylic acid {(1R,3S,4S)-2-[2-cyclopropyl-5-(3-fluoro-4-methyl-phenyl)-thiazole-4-carbonyl]-2-aza-bicyclo[2.2.1]hept-3-ylmethyl}-amide;

Benzothiazole-7-carboxylic acid {(1R,3S,4S)-2-[5-(3-chloro-phenyl)-2-methylamino-thiazole-4-carbonyl]-2-aza-bicyclo[2.2.1]hept-3-ylmethyl}-amide;

Benzothiazole-7-carboxylic acid {(1R,3S,4S)-2-[5-(3-chloro-phenyl)-2-ethylamino-thiazole-4-carbonyl]-2-aza-bicyclo[2.2.1]hept-3-ylmethyl}-amide;

Benzothiazole-7-carboxylic acid {(1R,3S,4S)-2-[2-methyl-5-(3-trifluoromethoxy-phenyl)-oxazole-4-carbonyl]-2-aza-bicyclo[2.2.1]hept-3-ylmethyl]-amide;

Benzo[d]isothiazole-3-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

5-Ethyl-3-methyl-isoxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

3-Ethyl-5-methyl-isoxazole-4-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

Quinoxaline-5-carboxylic acid {(1R,3S,4S)-2-[2-dimethylamino-5-(3-fluoro-phenyl)-thiazole-4-carbonyl]-2-aza-bicyclo[2.2.1]hept-3-ylmethyl}-amide;

Benzothiazole-7-carboxylic acid {(1R,3S,4S)-2-[3-(1H-indol-6-yl)-pyrazine-2-carbonyl]-2-aza-bicyclo[2.2.1]hept-3-ylmethyl}-amide;

Benzothiazole-7-carboxylic acid {(1S,3R,4R)-2-[5-(2-fluoro-phenyl)-2-pyrrolidin-1-yl-thiazole-4-carbonyl]-2-aza-bicyclo[2.2.1]hept-3-ylmethyl}-amide;

Benzothiazole-7-carboxylic acid [(1S,3R,4R)-2-(2-dimethylamino-5-m-tolyl-thiazole-4-carbonyl)-2-aza-bicyclo[2.2.1]hept-3-ylmethyl]-amide;

Benzothiazole-7-carboxylic acid {(1S,3R,4R)-2-[2-(ethyl-methyl-amino)-5-(3-methoxy-phenyl)-thiazole-4-carbonyl]-2-aza-bicyclo[2.2.1]hept-3-ylmethyl}-amide;

Benzothiazole-7-carboxylic acid {(1S,3R,4R)-2-[5-(3-bromo-4-fluoro-phenyl)-2-dimethylamino-thiazole-4-carbonyl]-2-aza-bicyclo[2.2.1]hept-3-ylmethyl}-amide;

Benzothiazole-7-carboxylic acid {(1S,3R,4R)-2-[5-(4-fluoro-phenyl)-2-pyrrolidin-1-yl-thiazole-4-carbonyl]-2-aza-bicyclo[2.2.1]hept-3-ylmethyl}-amide;

Benzothiazole-7-carboxylic acid {(1S,3R,4R)-2-[2-dimethylamino-5-(4-fluoro-phenyl)-thiazole-4-carbonyl]-2-aza-bicyclo[2.2.1]hept-3-ylmethyl}-amide;

Benzothiazole-7-carboxylic acid {(1S,3R,4R)-2-[2-diethylamino-5-(2-fluoro-phenyl)-thiazole-4-carbonyl]-2-aza-bicyclo[2.2.1]hept-3-ylmethyl}-amide;

Benzothiazole-7-carboxylic acid {(1S,3R,4R)-2-[2-dimethylamino-5-(3-fluoro-4-methyl-phenyl)-thiazole-4-carbonyl]-2-aza-bicyclo[2.2.1]hept-3-ylmethyl}-amide;

Benzothiazole-7-carboxylic acid {(1S,3R,4R)-2-[2-(ethyl-methyl-amino)-5-(4-fluoro-phenyl)-thiazole-4-carbonyl]-2-aza-bicyclo[2.2.1]hept-3-ylmethyl}-amide;

Benzothiazole-7-carboxylic acid [(1S,3R,4R)-2-(2-dimethylamino-5-p-tolyl-thiazole-4-carbonyl)-2-aza-bicyclo[2.2.1]hept-3-ylmethyl]-amide;

Benzothiazole-7-carboxylic acid {(1S,3R,4R)-2-[2-dimethylamino-5-(3-trifluoromethyl-phenyl)-thiazole-4-carbonyl]-2-aza-bicyclo[2.2.1]hept-3-ylmethyl}-amide; and Benzothiazole-7-carboxylic acid {(1S,3R,4R)-2-[2-diethylamino-5-(4-fluoro-phenyl)-thiazole-4-carbonyl]-2-aza-bicyclo[2.2.1]hept-3-ylmethyl}-amide;

or a pharmaceutically acceptable salt of such a compound.

10. A pharmaceutical composition containing, as active principle, a compound of formula (I) according to claim 1, or a pharmaceutically acceptable salt thereof, and at least one therapeutically inert excipient.

11. A compound according to claim 3, wherein
A represents phenyl or 5- to 6-membered monocyclic heterocyclyl, wherein the phenyl or heterocyclyl is unsubstituted or mono- or di-substituted, wherein the substituents are independently selected from the group consisting of $(C_{1-4})$alkyl, $(C_{3-6})$cycloalkyl, $(C_{1-4})$alkoxy, $NR^2R^3$ and halogen;
or a pharmaceutically acceptable salt of such a compound.

12. A compound according to claim 11, wherein
B represents aryl, wherein the aryl is unsubstituted or mono-, di-, or tri-substituted, wherein the substituents are independently selected from the group consisting of $(C_{1-4})$alkyl, $(C_{1-4})$alkoxy, trifluoromethyl and halogen;
or a pharmaceutically acceptable salt of such a compound.

13. A compound according to claim 3, wherein
$R^1$ represents heterocyclyl, wherein the heterocyclyl is unsubstituted or independently mono-, di-, or tri-substituted, wherein the substituents are independently selected from the group consisting of $(C_{1-4})$alkyl, $(C_{1-4})$alkoxy and halogen; or
$R^1$ represents a 1H-indenyl, a 2,3-dihydro-benzo[1,4]dioxinyl-, a 2,3-dihydro-thieno[3,4-b] [1,4]dioxinyl-, a 3,4-dihydro-2H-benzo[1,4]oxazinyl- or a 2,3,6,7-tetrahydro-benzo[1,2-b; 4,5-b']difuranyl-group, wherein said groups are unsubstituted or mono- or di-substituted wherein the substituents are independently selected from the group consisting of $(C_{1-4})$alkyl, $(C_{1-4})$alkoxy and halogen; or a pharmaceutically acceptable salt of such a compound.

14. A compound according to claim 11, wherein
$R^1$ represents heterocyclyl, wherein the heterocyclyl is unsubstituted or independently mono-, di-, or tri-substituted, wherein the substituents are independently selected from the group consisting of $(C_{1-4})$alkyl, $(C_{1-4})$alkoxy and halogen; or
$R^1$ represents a 1H-indenyl, a 2,3-dihydro-benzo[1,4]dioxinyl-, a 2,3-dihydro-thieno[3,4-b][1,4]dioxinyl-, a 3,4-dihydro-2H-benzo[1,4]oxazinyl- or a 2,3,6,7-tetrahydro-benzo[1,2-b; 4,5-b']difuranyl-group, wherein said groups are unsubstituted or mono- or di-substituted wherein the substituents are independently selected from the group consisting of $(C_{1-4})$alkyl, $(C_{1-4})$alkoxy and halogen; or a pharmaceutically acceptable salt of such a compound.

15. A compound according to claim 3, wherein, in case $R^1$ represents heterocyclyl, said heterocyclyl is selected from isoxazolyl, thiazolyl, pyrazolyl, pyridyl, indolyl, benzofuranyl, benzothiophenyl, indazolyl, benzimidazolyl, benzoxazolyl, benzisoxazolyl, benzothiazolyl, benzoisothiazolyl, benzothiadiazolyl, quinoxalinyl, quinolinyl, isoquinolinyl, pyrrolo[2,1-b]thiazolyl, imidazo[1,2-a]pyridyl and imidazo [2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy and halogen;
or a pharmaceutically acceptable salt of such a compound.

16. A compound according to claim 11, wherein, in case $R^1$ represents heterocyclyl, said heterocyclyl is selected from isoxazolyl, thiazolyl, pyrazolyl, pyridyl, indolyl, benzofuranyl, benzothiophenyl, indazolyl, benzimidazolyl, benzoxazolyl, benzisoxazolyl, benzothiazolyl, benzoisothiazolyl, benzothiadiazolyl, quinoxalinyl, quinolinyl, isoquinolinyl, pyrrolo[2,1-b]thiazolyl, imidazo[1,2-a]pyridyl and imidazo [2,1-b]thiazolyl, wherein said heterocyclyl is unsubstituted or mono-, di-, or tri-substituted, wherein the substituents are independently selected from the group consisting of $(C_{1-4})$alkyl, $(C_{1-4})$alkoxy and halogen;
or a pharmaceutically acceptable salt of such a compound.

17. A compound according to claim 4, wherein n represents the integer 0;
or a pharmaceutically acceptable salt of such a compound.

18. A compound according to claim 7, wherein n represents the integer 0;
or a pharmaceutically acceptable salt of such a compound.

19. A compound according to claim 1, wherein
A represents phenyl or 5- or 6-membered monocyclic heterocyclyl, wherein the phenyl or heterocyclyl is unsubstituted or independently mono- or di-substituted, wherein the substituents are independently selected from the group consisting of $(C_{1-4})$alkyl, $(C_{3-6})$cycloalkyl, $(C_{1-4})$alkoxy, and halogen;
B represents an phenyl-or a heterocyclyl-group selected from the group consisting of thienyl, thiazolyl, isothiazolyl, thiadiazolyl, pyrazolyl, pyridyl, pyrimidyl, pyridazinyl, and pyrazinyl;
wherein the phenyl or heterocyclyl is unsubstituted or independently mono-, di-, or tri-substituted, wherein the substituents are independently selected from the group consisting of $(C_{1-4})$alkyl, $(C_{1-4})$alkoxy, trifluoromethyl and halogen; wherein B is attached in ortho position to the point of attachment of the carbonyl group which links A to the 2-aza-bicyclo[2.2.1]heptane moiety;
n represents the integer 0 or 1;
$R^1$ represents heterocyclyl, wherein the heterocyclyl is unsubstituted or mono-, di-, or tri -substituted, wherein the substituents are independently selected from the group consisting of $(C_{1-4})$alkyl, $(C_{1-4})$alkoxy and halogen;
or a pharmaceutically acceptable salt of such a compound.

20. A pharmaceutical composition containing, as active principle, a compound of formula (I) according to claim 9, or a pharmaceutically acceptable salt thereof, and at least one therapeutically inert excipient.

21. A method for the treatment of a disease selected from the group consisting of insomnia, dysregulated appetite control, compulsive obesities, emeto-bulimia, anorexia nervosa, polydipsias in psychiatric disorders, and excessive fluid intake comprising administering to a subject a pharmaceutically active amount of a compound according to claim 1 or a pharmaceutically acceptable salt thereof.

22. A method for the treatment of a disease selected from the group consisting of insomnia, dysregulated appetite control, compulsive obesities, emeto-bulimia, anorexia nervosa, polydipsias in psychiatric disorders, and excessive fluid intake, comprising administering to a subject a pharmaceutically active amount of a compound according to claim 9, or a pharmaceutically acceptable salt thereof.

* * * * *

UNITED STATES PATENT AND TRADEMARK OFFICE
CERTIFICATE OF CORRECTION

PATENT NO.          : 8,236,801 B2
APPLICATION NO.     : 12/867630
DATED               : August 7, 2012
INVENTOR(S)         : Aissaoui et al.

Page 1 of 1

It is certified that error appears in the above-identified patent and that said Letters Patent is hereby corrected as shown below:

Column 83, line 47, please replace "hept-3-ylmethyl]-amide; 0" with "hept-3-ylmethyl]-amide;"

Column 83, line 60, please replace "[2.2.1]kept-3-ylmethyl]}-amide" with "[2.2.1]hept-3-ylmethyl]}-amide"

Column 84, line 51, please replace "aza-bicyclo[2.2.1]kept-3-ylmethyl]}-amide" with "aza-bicyclo[2.2.1]hept-3-ylmethyl]}-amide"

Column 86, line 22, please replace "nyl}-2-aza-bicyclo[2.2.1]hept-3-ylmethyl]-amide" with "nyl]-2-aza-bicyclo[2.2.1]hept-3-ylmethyl}-amide"

Signed and Sealed this
Twenty-seventh Day of November, 2012

David J. Kappos
*Director of the United States Patent and Trademark Office*